United States Patent
Miyata

(10) Patent No.: US 9,502,661 B2
(45) Date of Patent: Nov. 22, 2016

(54) AMINE DERIVATIVE, ORGANIC ELECTROLUMINESCENCE MATERIAL HAVING THE SAME AND ORGANIC ELECTROLUMINESCENCE DEVICE USING THE MATERIAL

(71) Applicant: SAMSUNG DISPLAY CO., LTD., Yongin, Gyeonggi-Do (KR)

(72) Inventor: Yasuo Miyata, Yongin (KR)

(73) Assignee: SAMSUNG DISPLAY CO., LTD., Yongin, Gyeonggi-Do (KR)

( * ) Notice: Subject to any disclaimer, the term of this patent is extended or adjusted under 35 U.S.C. 154(b) by 191 days.

(21) Appl. No.: 14/097,686

(22) Filed: Dec. 5, 2013

(65) Prior Publication Data

US 2014/0151667 A1  Jun. 5, 2014

(30) Foreign Application Priority Data

Dec. 5, 2012  (JP) .................. 2012-266795

(51) Int. Cl.

| | |
|---|---|
| H01L 51/00 | (2006.01) |
| C07D 401/04 | (2006.01) |
| C07D 401/10 | (2006.01) |
| C07D 403/10 | (2006.01) |
| C07D 405/04 | (2006.01) |
| C07D 405/12 | (2006.01) |
| C07D 409/04 | (2006.01) |
| C07D 409/12 | (2006.01) |
| C07D 495/04 | (2006.01) |
| C07D 209/86 | (2006.01) |
| C07D 209/88 | (2006.01) |
| H01L 51/50 | (2006.01) |

(52) U.S. Cl.
CPC ......... *H01L 51/0061* (2013.01); *C07D 209/86* (2013.01); *C07D 209/88* (2013.01); *C07D 401/04* (2013.01); *C07D 401/10* (2013.01); *C07D 403/10* (2013.01); *C07D 405/04* (2013.01); *C07D 405/12* (2013.01); *C07D 409/04* (2013.01); *C07D 409/12* (2013.01); *C07D 495/04* (2013.01); *H01L 51/006* (2013.01); *H01L 51/0059* (2013.01); *H01L 51/0072* (2013.01); *H01L 51/0081* (2013.01); *H01L 51/5056* (2013.01)

(58) Field of Classification Search
None
See application file for complete search history.

(56) References Cited

U.S. PATENT DOCUMENTS

| | | |
|---|---|---|
| 2007/0231503 A1 | 10/2007 | Hwang et al. |
| 2008/0169755 A1 | 7/2008 | Kim et al. |
| 2010/0032656 A1 | 2/2010 | Kwang et al. |
| 2012/0217492 A1 | 8/2012 | Kim et al. |

FOREIGN PATENT DOCUMENTS

| | | |
|---|---|---|
| JP | 2003313547 A | 11/2003 |
| JP | 2004-115443 A | 4/2004 |
| JP | 2005-44791 A | 2/2005 |
| JP | 2005-290000 A | 10/2005 |
| JP | 2006-273791 A | 10/2006 |
| JP | 2007-318101 A | 12/2007 |
| JP | 2008-044923 A | 2/2008 |
| JP | 2008-120786 A | 5/2008 |
| JP | 2008-133263 A | 6/2008 |
| JP | 2009-185030 A | 8/2009 |
| JP | 2010-031012 A | 2/2010 |
| JP | 2010-053131 A | 3/2010 |
| JP | 2011-187959 A | 9/2011 |
| JP | 2012-019172 A | 1/2012 |
| JP | 2013-251480 A | 12/2013 |
| WO | WO 2007/063986 A1 | 6/2007 |
| WO | WO 2008/062636 A | 5/2008 |
| WO | WO-2010/110553 A2 | 9/2010 |
| WO | WO 2012/011756 A1 | 1/2012 |
| WO | WO 2012/043996 A2 | 4/2012 |
| WO | WO-2012/091471 A2 | 5/2012 |

OTHER PUBLICATIONS

Grant & Hackh's Chemical Dictionary (5th Ed. 1987) at p. 148.*
CAPLUS printout of Foreign Patent No. KR2013021585.*
CAPLUS printout of Foreign Patent No. KR2013022232.*
CAPLUS printout of Foreign Patent No. KR1111406.*

* cited by examiner

Primary Examiner — Rebecca Anderson
Assistant Examiner — Po-Chih Chen
(74) Attorney, Agent, or Firm — Lee & Morse, P.C.

(57) ABSTRACT

An amine derivative including a fluorine substituted aryl group is represented by compound (1) of the following Formula 1.

[Formula 1]

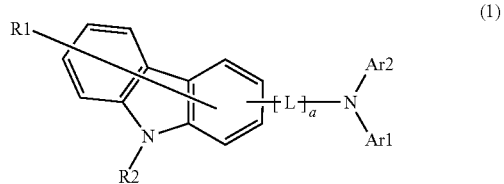

(1)

wherein, each of Ar1 and Ar2 independently represents a substituted or unsubstituted aryl group or a substituted or unsubstituted heteroaryl group, L is a substituted or unsubstituted arylene group or a substituted or unsubstituted heteroarylene group, each of R1 and R2 independently represents a hydrogen atom, a substituted or unsubstituted alkyl group, a substituted or unsubstituted alkoxy group, a substituted or unsubstituted aryl group, or a substituted or unsubstituted heteroaryl group, a is an integer satisfying $0 \leq a \leq 3$, and at least one of Ar1 and Ar2 is substituted with at least one fluorine atom.

5 Claims, 1 Drawing Sheet

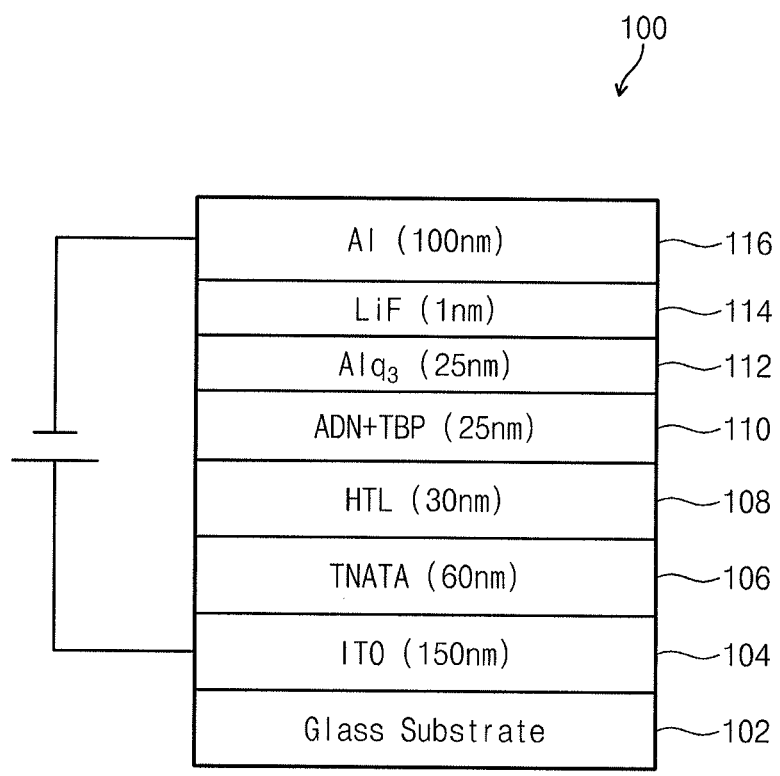

AMINE DERIVATIVE, ORGANIC ELECTROLUMINESCENCE MATERIAL HAVING THE SAME AND ORGANIC ELECTROLUMINESCENCE DEVICE USING THE MATERIAL

CROSS-REFERENCE TO RELATED APPLICATION

Japanese Patent Application No. 2012-266795, filed on Dec. 5, 2012, in the Japanese Intellectual Property Office, and entitled: "Amine Derivative, Organic Electroluminescence Material Having the Same and Organic Electroluminescence Device Using the Material," is incorporated by reference herein in its entirety.

BACKGROUND

1. Field

Embodiments relate to an amine derivative, an organic electroluminescence material having the same and an organic electroluminescence device using the material.

2. Description of the Related Art

In recent years, organic electroluminescence (EL) displays, which are one type of image displays, have been actively developed. Unlike a liquid crystal display and the like, the organic EL display is a self-luminescent display in which holes and electrons injected from a positive electrode and a negative electrode are recombined in an emission layer to thus emit a light from a light-emitting material including an organic compound of the emission layer, thereby displaying an image.

An example of a general light-emitting device may include an organic EL device that includes a positive electrode, a hole transport layer on the positive electrode, an emission layer on the hole transport layer, an electron transport layer on the emission layer, and a negative electrode on the electron transport layer. Holes injected from the positive electrode may be transported into the emission layer via the hole transport layer. Electrons are injected from the negative electrode, and then transported into the emission layer via the electron transport layer. The holes and the electrons injected into the emission layer recombine to generate excitons within the emission layer. The organic EL device emits a light by using light generated by radiation and deactivation of the excitons. The organic EL device may be provided in various forms.

SUMMARY

Embodiments are directed to an amine derivative including a fluorine substituted aryl group, represented by the following Formula 1:

[Formula 1]

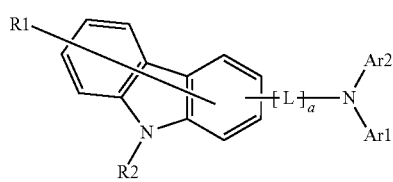

(1)

wherein, each of Ar1 and Ar2 independently represents a substituted or unsubstituted aryl group or a substituted or unsubstituted heteroaryl group, L is a substituted or unsubstituted arylene group or a substituted or unsubstituted heteroarylene group, each of R1 and R2 independently represents a hydrogen atom, a substituted or unsubstituted alkyl group, a substituted or unsubstituted alkoxy group, a substituted or unsubstituted aryl group, or a substituted or unsubstituted heteroaryl group, a is an integer satisfying $0 \leq a \leq 3$, and at least one of Ar1 and Ar2 is substituted with at least one fluorine atom.

The amine derivative may be a fluorine substituted aryl group represented by following Formula 2 or Formula 3.

[Formula 2]

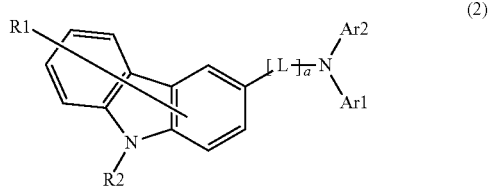

(2)

[Formula 3]

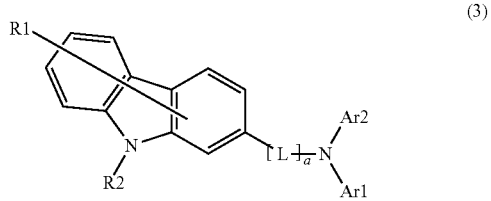

(3)

where R1, R2, L, a, Ar1 and Ar2 have the same definitions as in Formula 1.

Each of Ar1 and Ar2 independently may independently represent a substituted or unsubstituted aryl group having 6 to 20 carbon atoms, and L may be a substituted or unsubstituted arylene group having 6 to 20 carbon atoms.

Each of Ar1 and Ar2 may independently represent a substituted or unsubstituted phenyl group or biphenyl group, and L may be a substituted or unsubstituted phenylene group or biphenylylene group.

Each of R1 and R2 may independently represent a hydrogen atom, or a substituted or unsubstituted aryl group.

Each of Ar1 and Ar2 may independently represent a substituted or unsubstituted biphenyl group, L may be a substituted or unsubstituted phenylene group, R1 may be a hydrogen atom, and R2 is a substituted or unsubstituted aryl group.

An organic electroluminescence material may include the amine derivative including the fluorine substituted aryl group.

A hole transport material may include the amine derivative including the fluorine substituted aryl group described in claim 1.

An organic electroluminescence device may include at least an emission layer and a hole transport layer disposed between a negative electrode and a positive electrode. The hole transport layer may include the amine derivative including the fluorine substituted aryl group.

An amine derivative may be selected from the compounds 1 to 180 disclosed herein.

BRIEF DESCRIPTION OF THE DRAWING

Features will become apparent to those of ordinary skill in the art by describing in detail exemplary embodiments with reference to the attached drawings in which:

The accompanying drawing is included to provide a further understanding of the inventive concept, and is incorporated in and constitutes a part of this specification. The drawing illustrates exemplary embodiments of the inventive concept and, together with the description, serves to explain principles of the inventive concept. In the drawing:

FIG. 1 illustrates a schematic diagram depicting the constitution of an organic EL device.

DETAILED DESCRIPTION

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. It will also be understood that when a layer or element is referred to as being "on" another layer or substrate, it can be directly on the other layer or substrate, or intervening layers may also be present.

According to embodiments, an amine derivative including a fluorine substituted aryl group described herein below may be used as a material having electron durability, and a long life of an organic EL device may be realized by using the amine derivative including a fluorine substituted aryl group as the material of a hole transport layer in the organic EL device. Hereinafter, the amine derivative including a fluorine substituted aryl group. The amine derivative including a fluorine substituted aryl group, the organic EL material having the same and the organic EL device using the material of the inventive concept will be embodied as other various embodiments and are not interpreted as being limited to the following embodiments.

The amine derivative including a fluorine substituted aryl group concerning the inventive concept is represented by the following Formula 1.

[Formula 1]

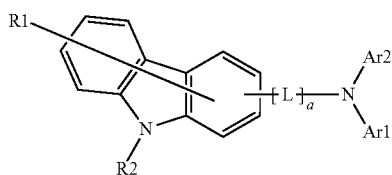

(1)

In Formula 1, each of Ar1 and Ar2 independently is a substituted or unsubstituted aryl group or a substituted or unsubstituted heteroaryl group. L is a substituted or unsubstituted arylene group or a substituted or unsubstituted heteroarylene group, each of R1 and R2 independently is a hydrogen atom, a substituted or unsubstituted alkyl group, a substituted or unsubstituted alkoxy group, a substituted or unsubstituted aryl group, or a substituted or unsubstituted heteroaryl group. "a" is an integer satisfying 0≤a≤3. In addition, in Formula 1, at least one of Ar1 and Ar2 is substituted with at least one fluorine atom. The number of the fluorine substituted into Ar1 and Ar2 may be appropriately determined according to the material of a layer adjacent to another layer including the amine derivative including a fluorine substituted aryl group, represented by Formula 1 in an organic EL device.

Each of Ar1 and Ar2 independently may be a substituted or unsubstituted aryl group having 6 to 20 carbon atoms or a substituted or unsubstituted heteroaryl group having 4 to 20 carbon atoms. The aryl group or the hetero aryl group of Ar1 and Ar2 may include, for example, a phenyl group, a naphthyl group, an anthracenyl group, a phenanthryl group, a biphenyl group, a terphenyl group, a fluorenyl group, a triphenylene group, a biphenylylene group, a pyrenyl group, a benzothiazolyl group, a thiophenyl group, a thienothiophenyl group, a benzothiophenyl group, a carbazolyl group, a pyridyl group, a pyrimidyl group, a triazyl group, a quinolinyl group, a quinoxaline group, or the like. Examples of the aryl groups of Ar1 and Ar2 may include a phenyl group and a biphenyl group. For example, Ar1 and/or Ar2 may be a biphenyl group. As described above, at least one aryl group among Ar1 and Ar2 is substituted with at least one fluorine atom.

L may be a substituted or unsubstituted arylene group having 6 to 20 carbon atoms or a substituted or unsubstituted heteroarylene group having 4 to 20 carbon atoms, and the arylene group or the heteroarylene group of L may include the same groups illustrated as the aryl group or the heteroaryl group of Ar1 and Ar2. As an example, the arylene group of L may be a phenylene group.

The substituted or unsubstituted alkyl group of R1 and R2 may be a substituted or unsubstituted alkyl group having 1 to 10 carbon atoms and may be, for example, a methyl group, an ethyl group, a propyl group, an isopropyl group, a cyclopropyl group, a butyl group, an isobutyl group, a tert-butyl group, a cyclobutyl group, a pentyl group, an isopentyl group, a neopentyl group, a cyclopentyl group, a hexyl group, a cyclohexyl group, a heptyl group, a cycloheptyl group, an octyl group, a nonyl group, a decyl group, or the like.

In addition, the substituted or unsubstituted alkoxy group of R1 and R2 may be a substituted or unsubstituted alkoxy group having 1 to 10 carbon atoms and may be, for example, a methoxy group, an ethoxy group, a n-propoxy group, an isopropoxy group, a n-butoxy group, an isobutoxy group, a tert-butoxy group, a n-pentyloxy group, a neopentyloxy group, a n-hexyloxy group, a n-heptyloxy group, a n-octyloxy group, a 2-ethylhexyloxy group, a nonyloxy group, a decyloxy group, a 3,7-dimethyloctyloxy group, or the like.

In addition, the substituted or unsubstituted aryl group or the substituted or unsubstituted heteroaryl group of R1 and R2 may be an aryl group having 6 to 20 carbon atoms or a heteroaryl group having 4 to 20 carbon atoms, and may be the same groups illustrated as the aryl group or the heteroaryl group of Ar1 and Ar2.

Substituents onto the aryl group or the heteroaryl group of Ar1 and Ar2 may include, for example, an alkyl group, an alkoxy group, an aryl group or a heteroaryl group. The alkyl group may be the examples of the alkyl group of R1 and R2, the alkoxy group may be the examples of the alkoxy group of R1 and R2, and the aryl group or the heteroaryl group may be the examples of the aryl group or the heteroaryl group of Ar1 and Ar2.

Substituents onto the arylene group or the heteroarylene group of L may include, for example, an alkyl group, an alkoxy group, an aryl group, or a heteroaryl group. The alkyl group may be the examples of the alkyl group of R1 and R2, the alkoxy group may be the examples of the alkoxy group of R1 and R2, and the aryl group or the heteroaryl group may be the examples of the aryl group or the heteroaryl group of Ar1 and Ar2.

Substituents onto the alkyl group, the aryl group, or the heteroaryl group of R1 and R2 may include, for example, an alkyl group, an alkoxy group, an aryl group or a heteroaryl group. The alkyl group may be the examples of the alkyl group of R1 and R2, the alkoxy group may be the examples of the alkoxy group of R1 and R2, the aryl group or the heteroaryl group may be the examples of the aryl group or the heteroaryl group of Ar1 and Ar2.

As examples, an the amine derivative including a fluorine substituted aryl group, represented by Formula 1 concerning the inventive concept, L or an amine portion may be substituted at position 2 or position 3 of a carbazole portion as illustrated in the following Formulas 2 and 3.

[Formula 2]

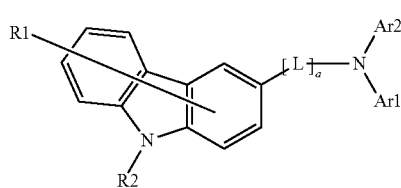

(2)

[Formula 3]

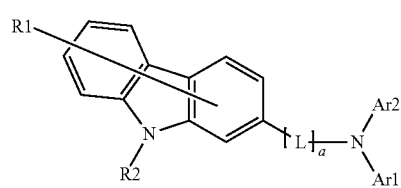

(3)

The amine derivative including a fluorine substituted aryl group according to embodiments includes the fluorine substituted aryl group, which is an electron accepting substituent into the amine derivative having a carbazole portion, which exhibits hole transport properties. Thus, the lowest unoccupied molecular orbital LUMO level of the amine derivative may be lowered, and electron durability thereof may be improved.

As described above, an organic EL device emits light through the recombination of holes and electrons injected into an emission layer. While emitting the light, the recombination of the holes and the electrons also is generated near the interface of the emission layer and a hole transport layer. In this case, electrons not participating in the combination with the holes may invade the hole transport layer and damage a hole transport material, thereby deteriorating the hole transport layer and promoting the deterioration of the organic EL device. As described above, the amine derivative including a fluorine substituted aryl group according to embodiments includes the carbazole portion having the hole transport properties and the fluorine substituted aryl group, which is the electron accepting substituent, and has high electron durability. Therefore, the deterioration of the hole transport material due to the electrons invading the hole transport layer may be restrained by using the amine derivative including a fluorine substituted aryl group as the hole transport material of the organic EL device. Also, the life of the organic EL device may be increased.

Examples of the substituents of Ar1 and Ar2 and examples of the carbazole portion including R1 and R2 in Formula 1 are illustrated in the following Table 1. The amine derivative including a fluorine substituted aryl group according to embodiments may be a compound including the substituents in one horizontal row in Table 1 into Ar1, Ar2 and the carbazole portion of Formula 1. Other substituents of Ar1 and Ar2 and the carbazole portion including R1 and R2 besides those shown in Table 1 may be used. In addition, any combination in which at least one aryl group among Ar1 and Ar2 is substituted with at least one fluorine atom may be included.

TABLE 1

| Ar1 | Ar2 | 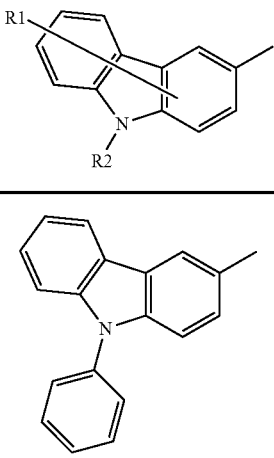 |
|---|---|---|

US 9,502,661 B2
TABLE 1-continued
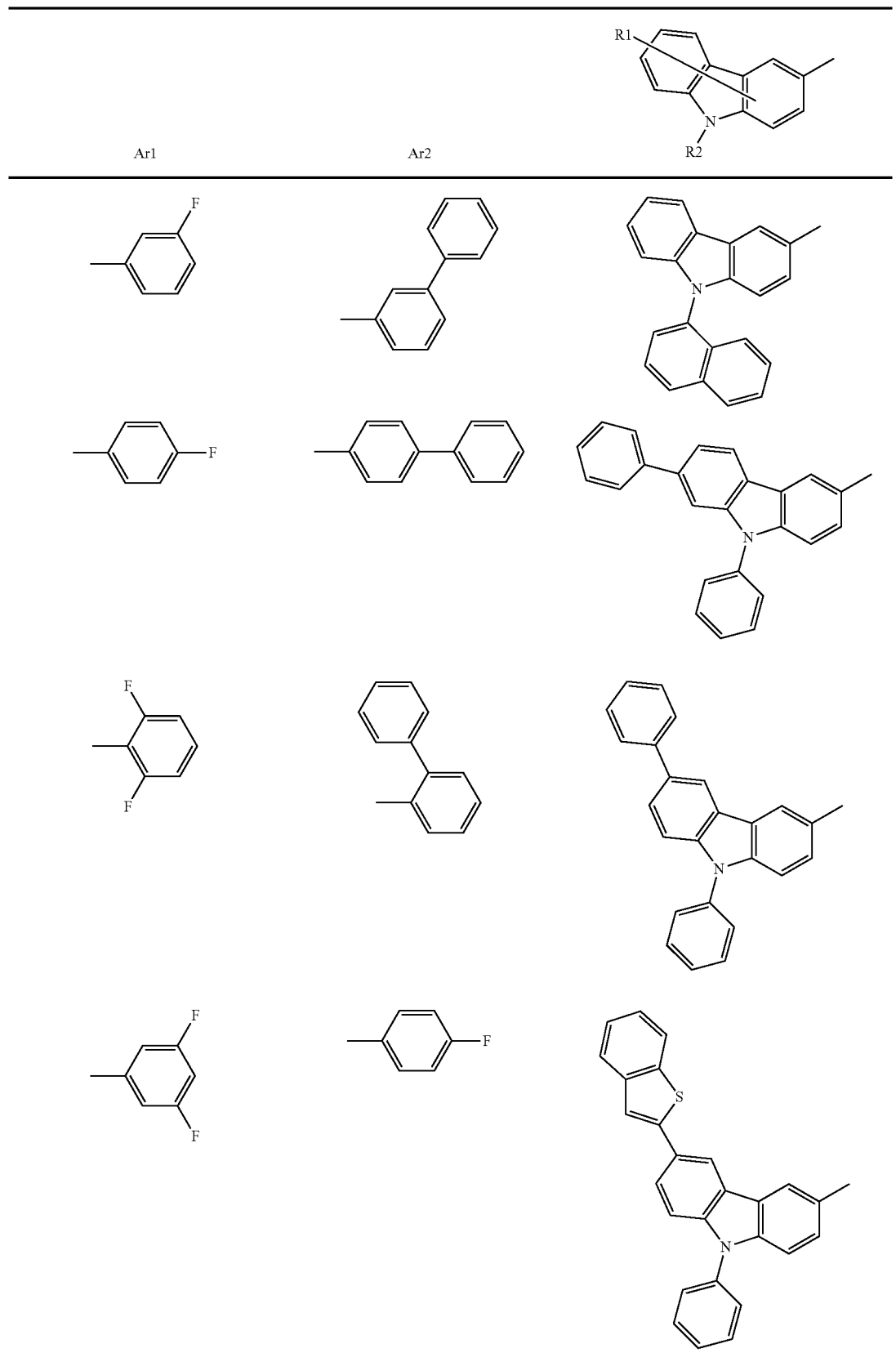

TABLE 1-continued
| Ar1 | Ar2 | 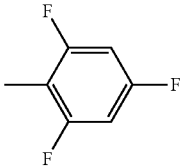 |
|---|---|---|
| 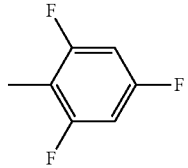 | 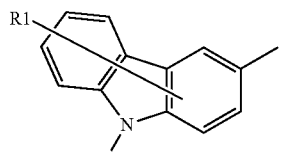 | 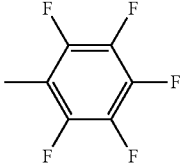 |
| 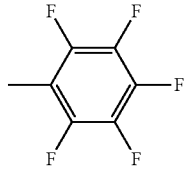 | 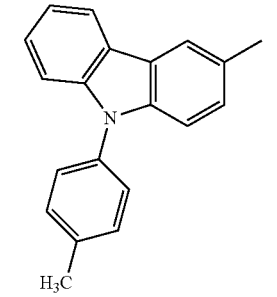 | 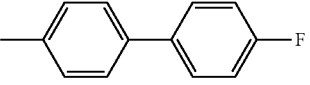 |
| 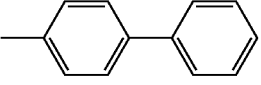 | 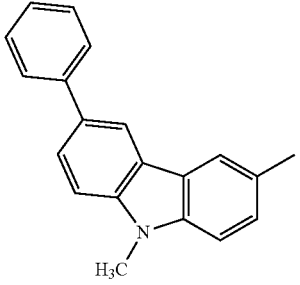 | 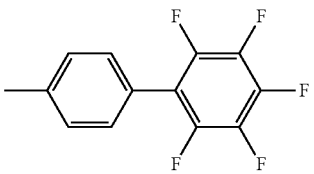 [SMILES: Cc1ccc(-c2c(F)c(F)c(F)c(F)c2F)cc1] |
| 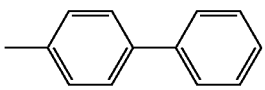 | 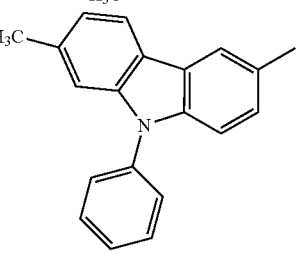 | 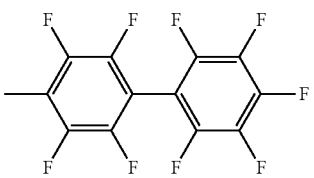 [SMILES: Cc1c(F)c(F)c(-c2c(F)c(F)c(F)c(F)c2F)c(F)c1F] |
| 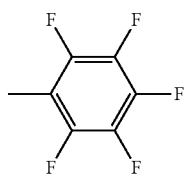 | | 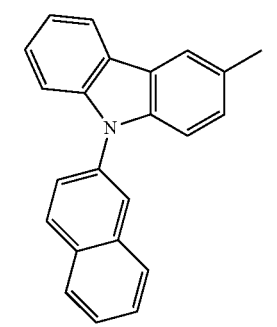 [SMILES: Cc1ccc2c(c1)c1ccccc1n2-c1ccc2ccccc2c1] |

In the carbazole portion including R1 and R2 in Formula 1, a 9-phenylcarbazolyl group, in which R1 is a hydrogen atom, and R2 is a phenyl group, may be provided, as an example. As an example, the substituting position of the fluorine in Ar1 or Ar2 in Formula 1 may be a para position with respect to a combining position of Ar1 or Ar2 with a nitrogen atom.

Particular examples of the amine derivative including a fluorine substituted aryl group according to embodiments will be illustrated herein below. However, in other implementations, the amine derivative including a fluorine substituted aryl group according to embodiments may be other compounds besides following compounds.

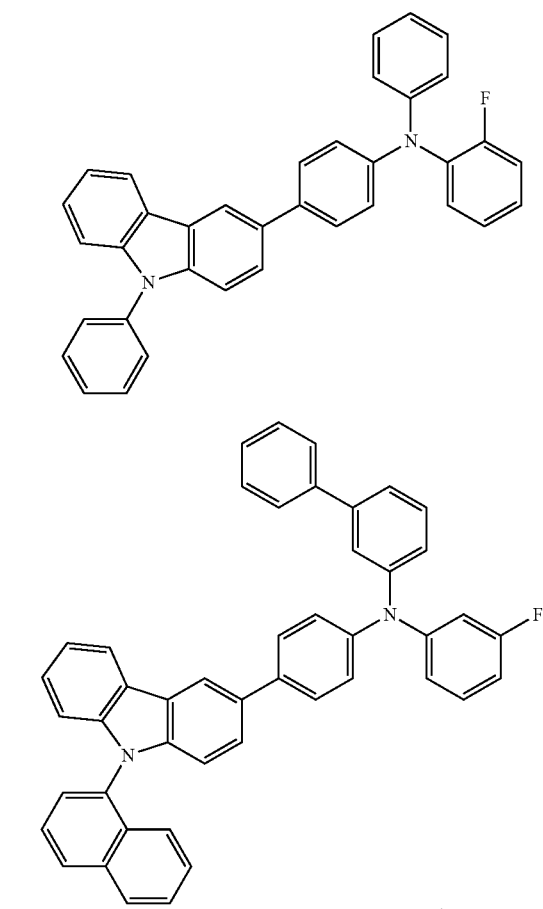

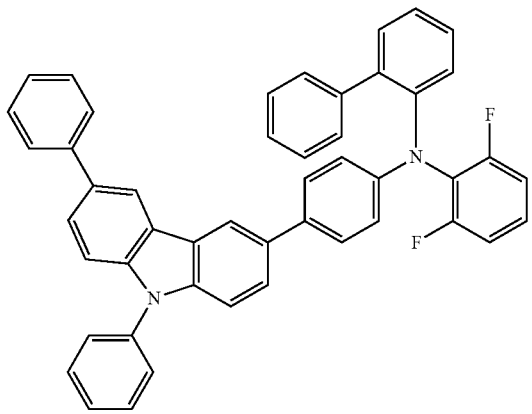

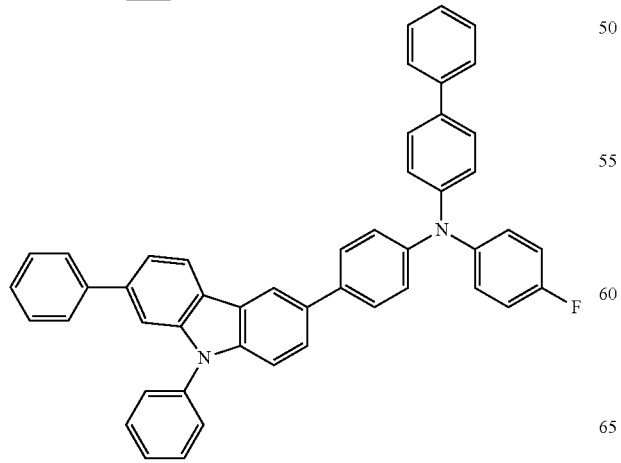

-continued

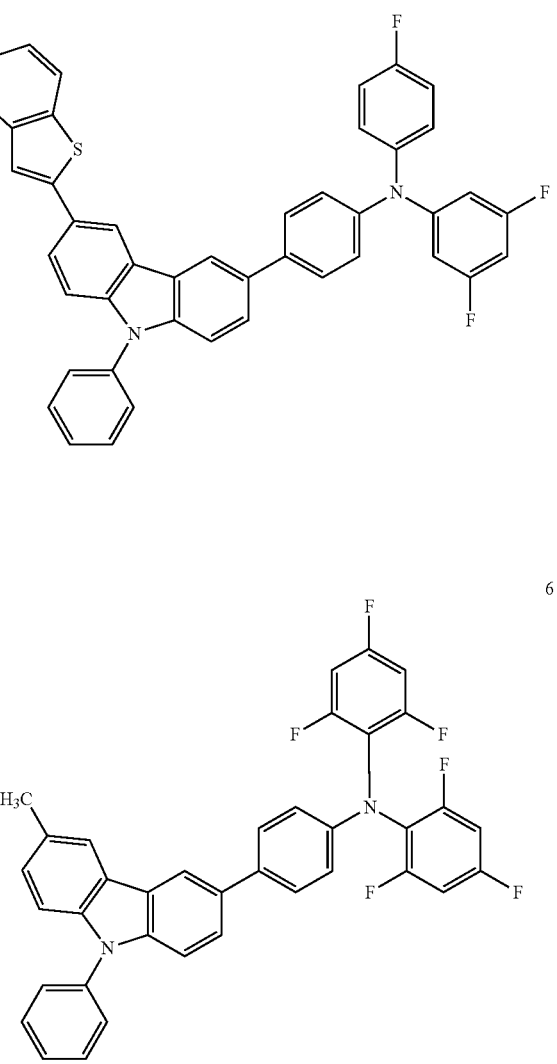

-continued

7

8

9

10

11

12

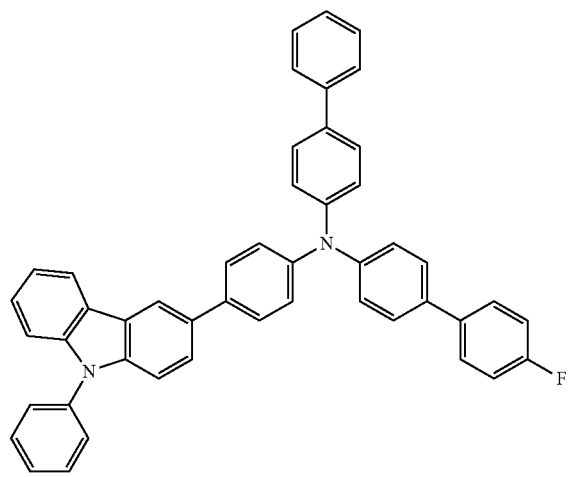
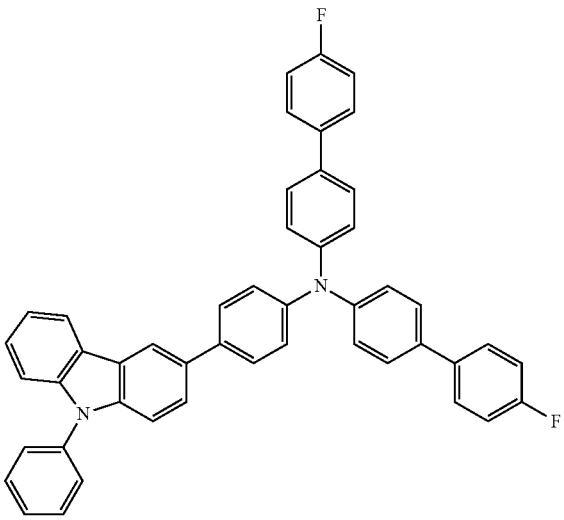
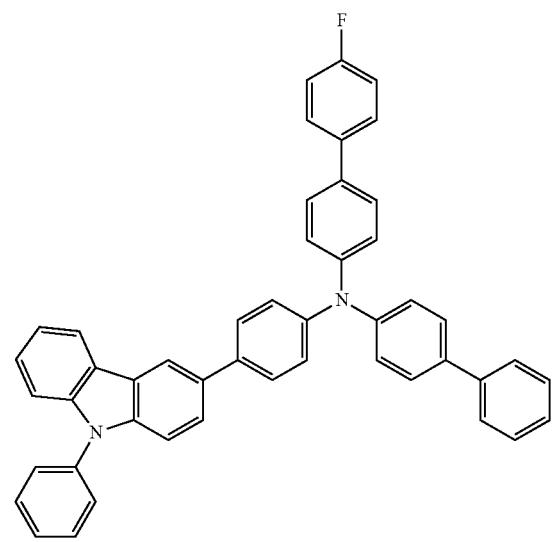
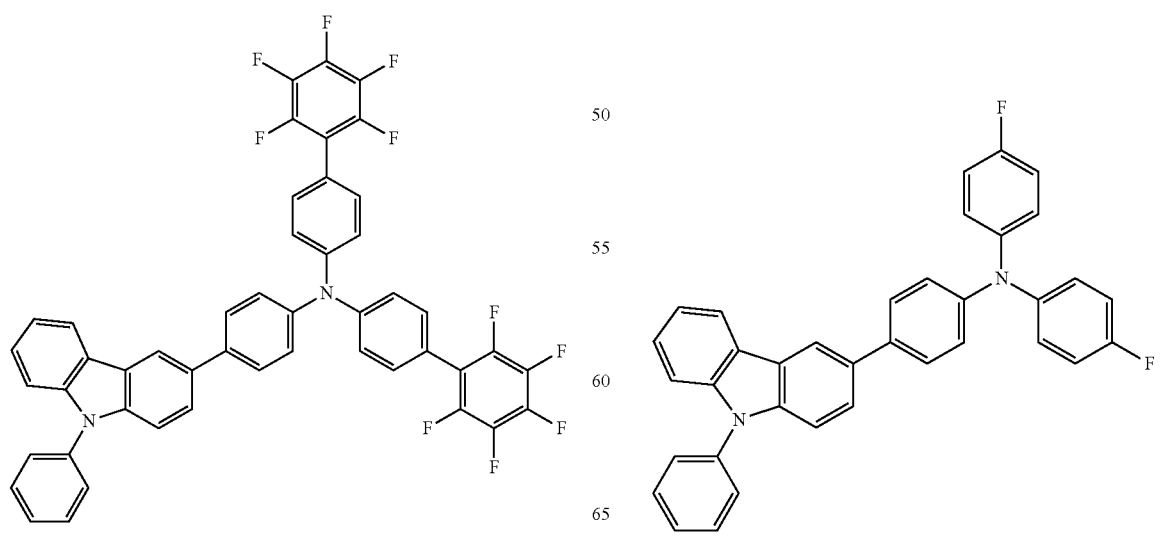

19
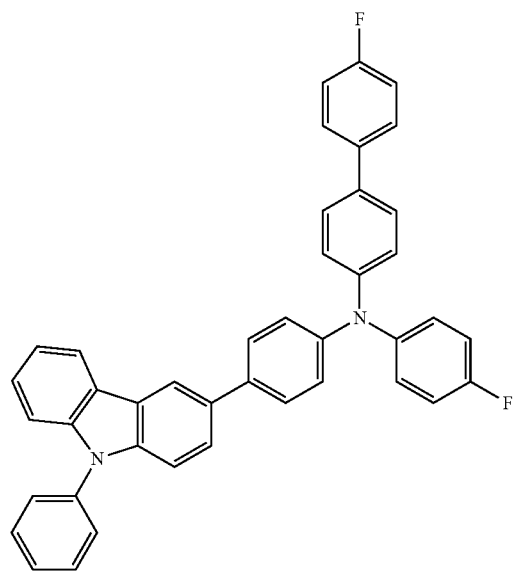
20
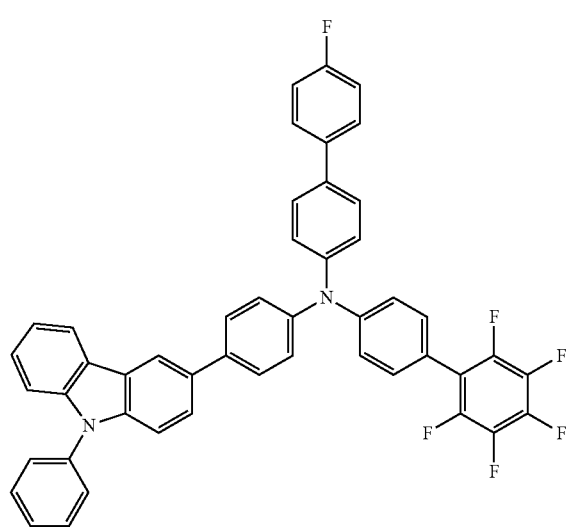
21
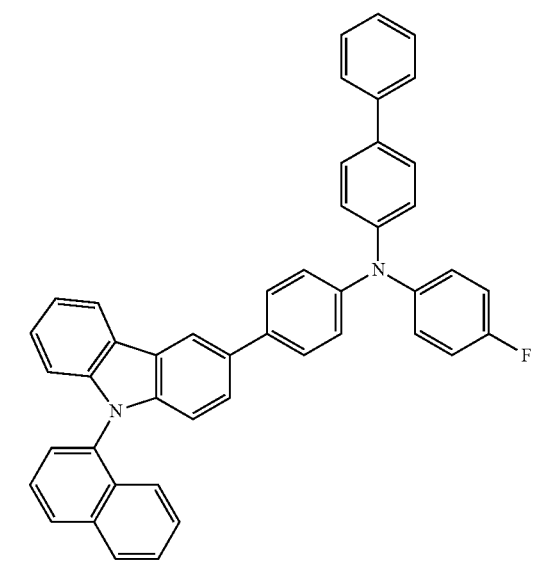
22
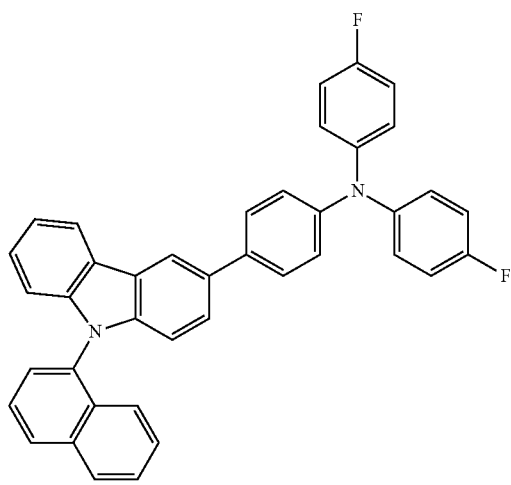
23
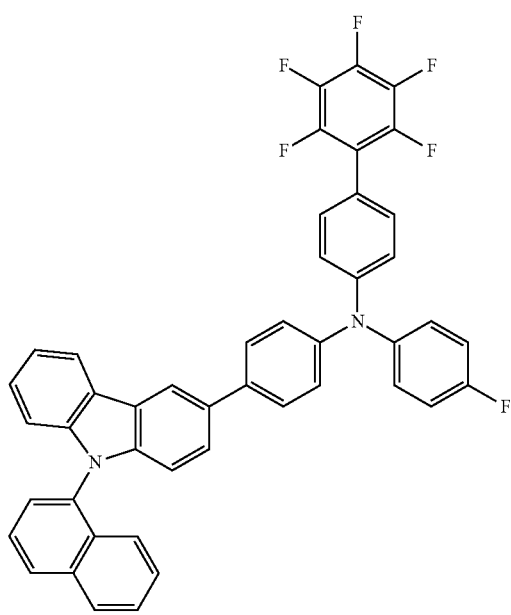
24
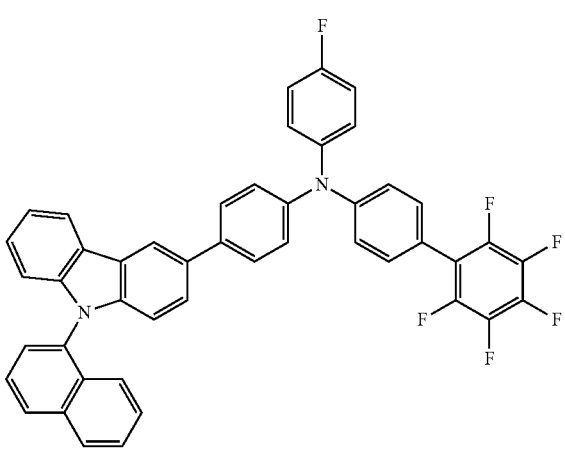

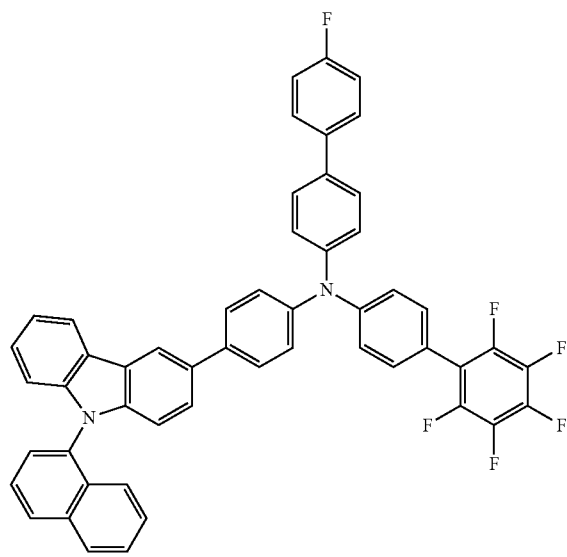
25
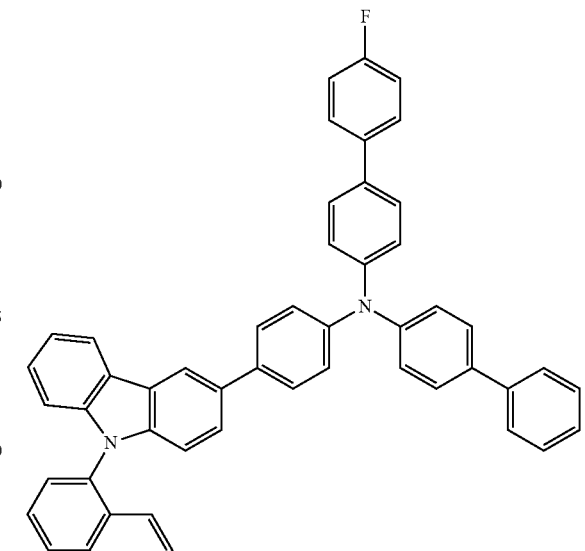
27
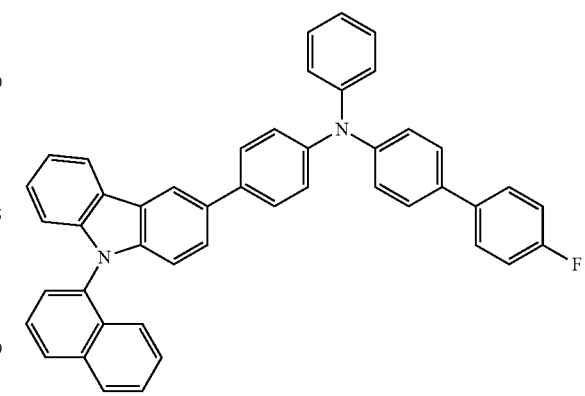
28
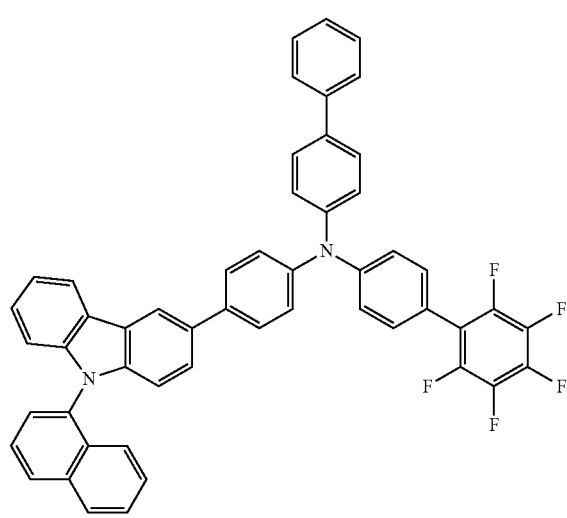
26
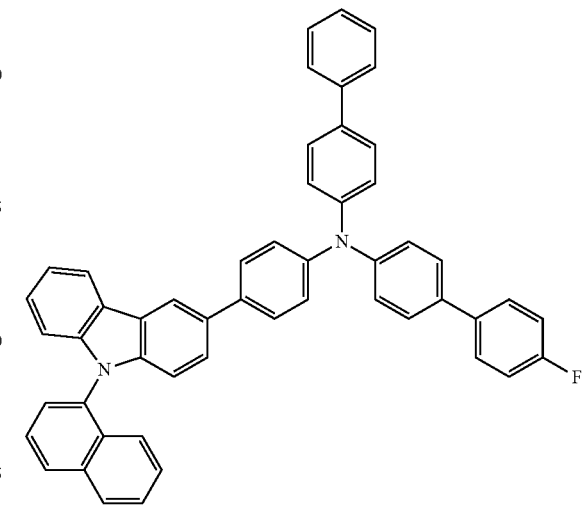
29

30
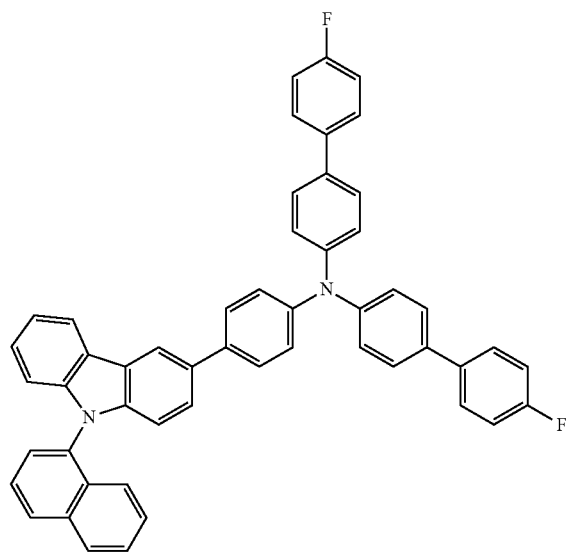
33
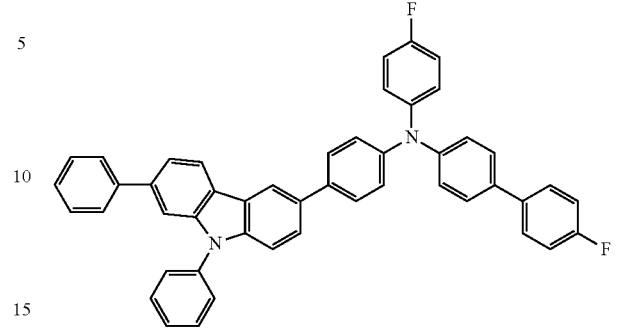
34
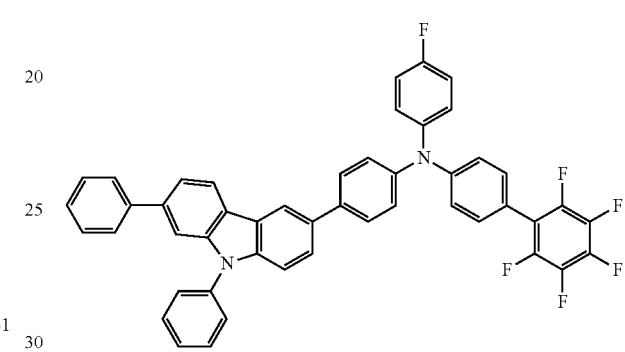
31
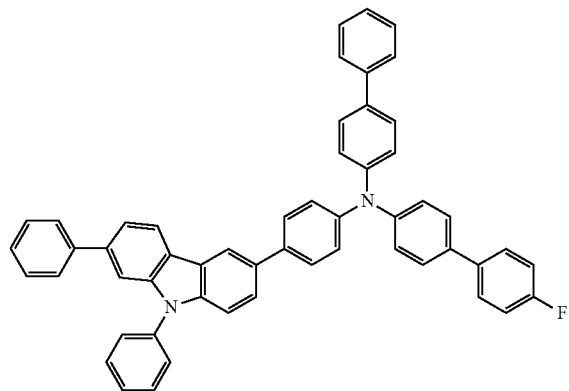
35
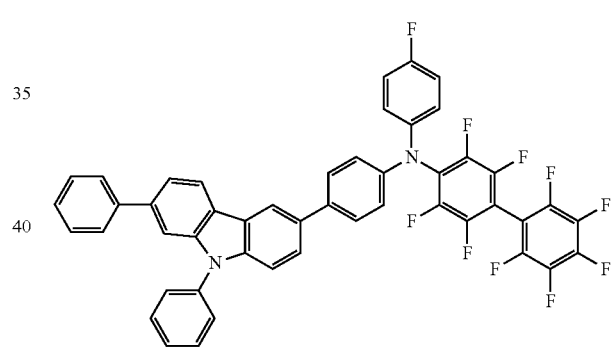
32
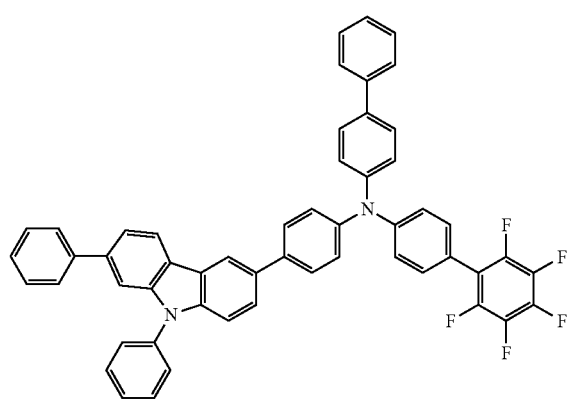
36
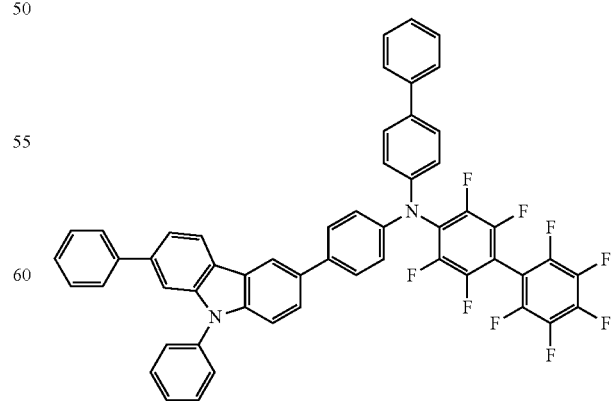

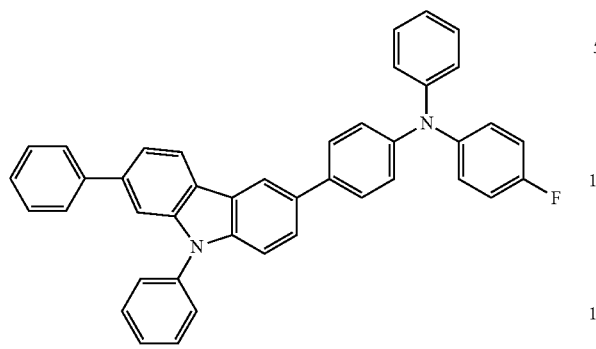
37
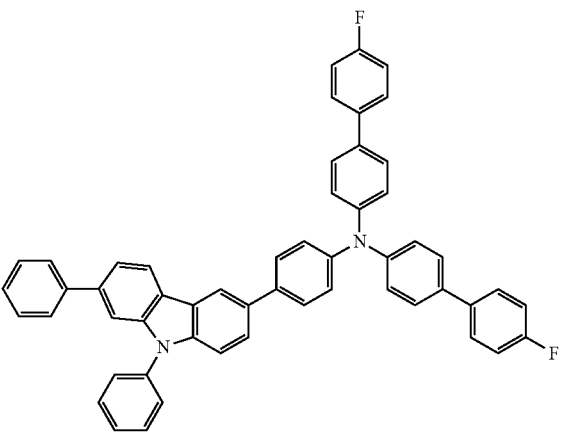
40
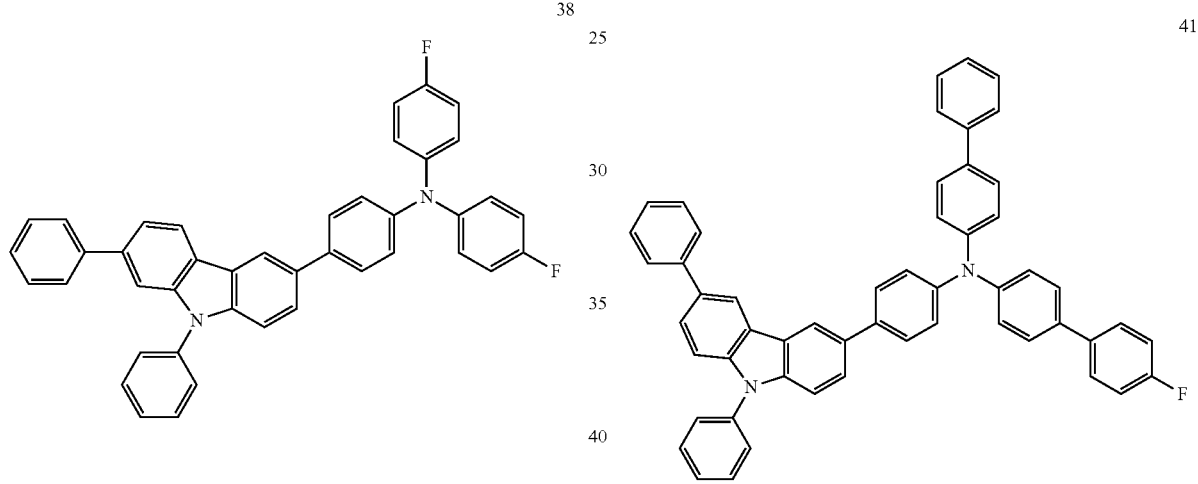
38
41
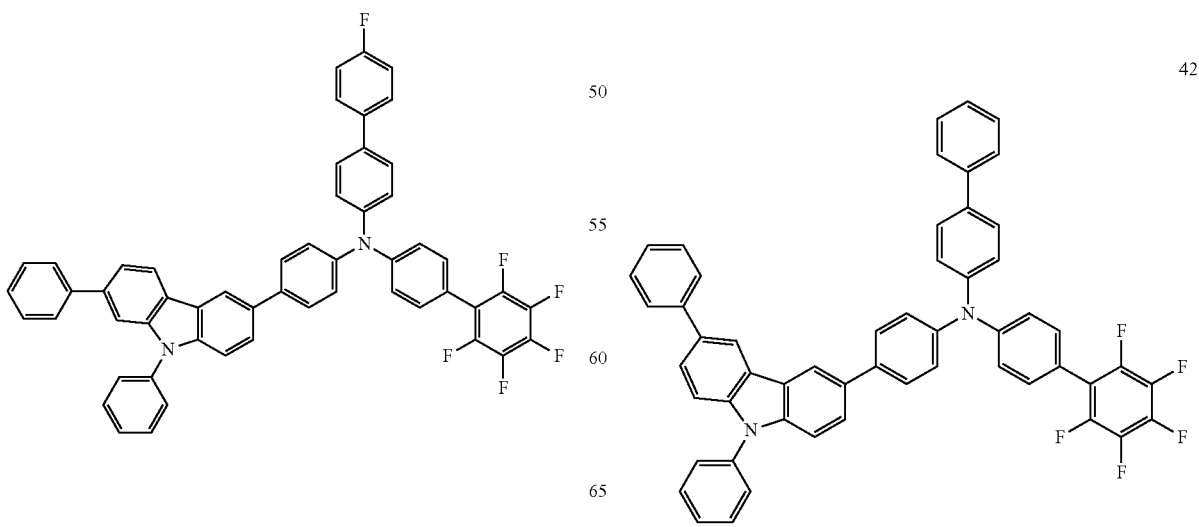
39
42

-continued
43
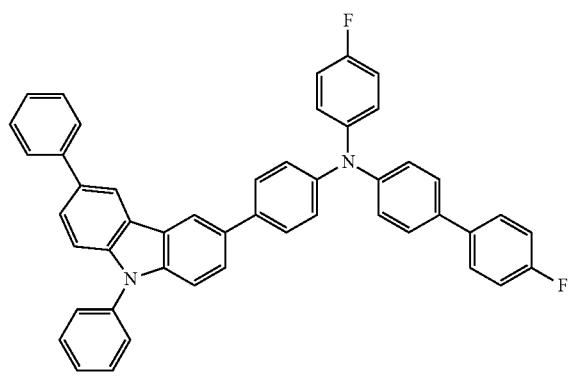
44
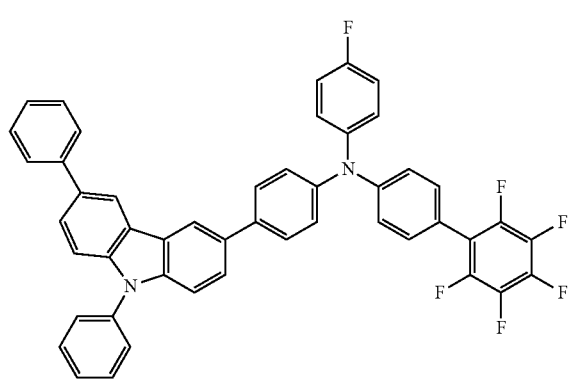
45
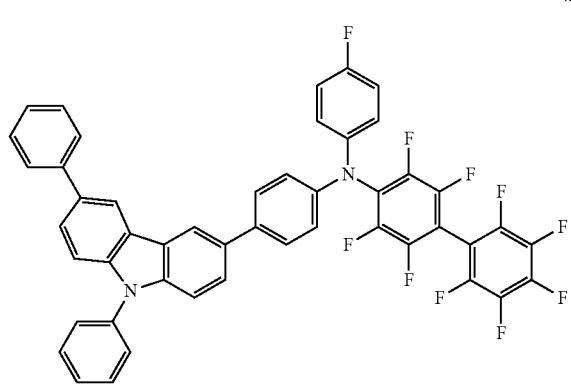
46
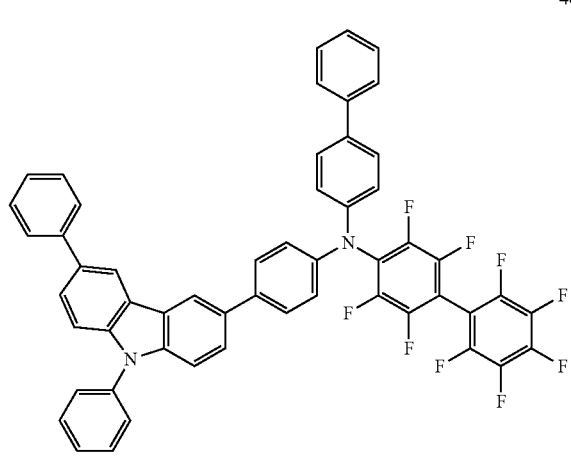
-continued
47
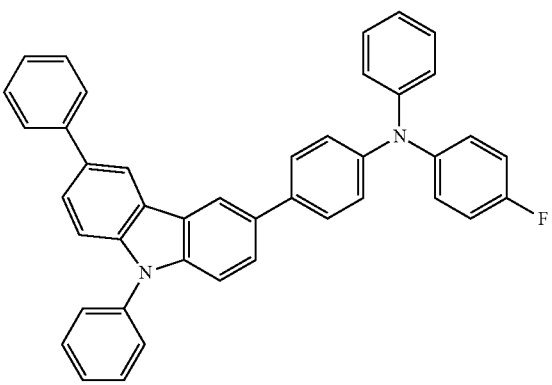
48
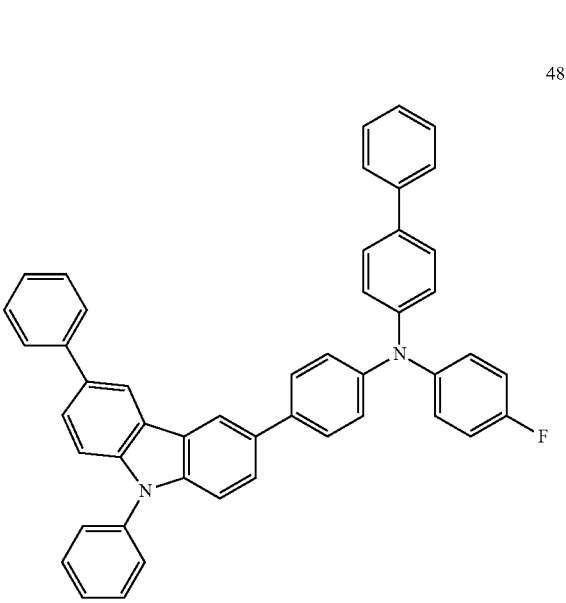
49
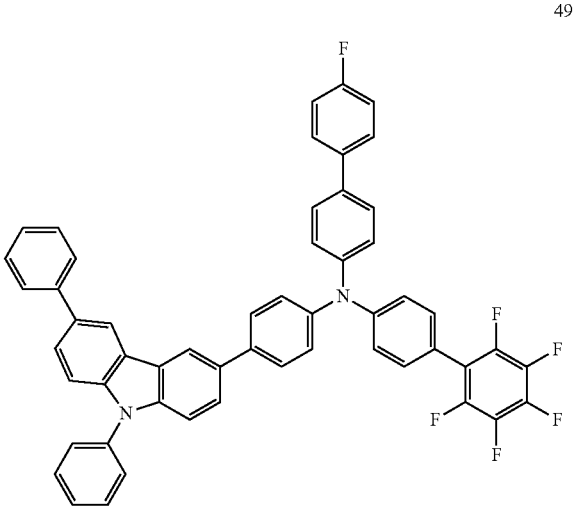

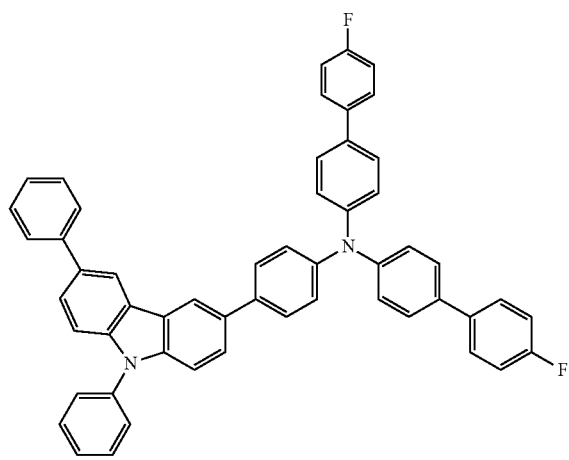
50
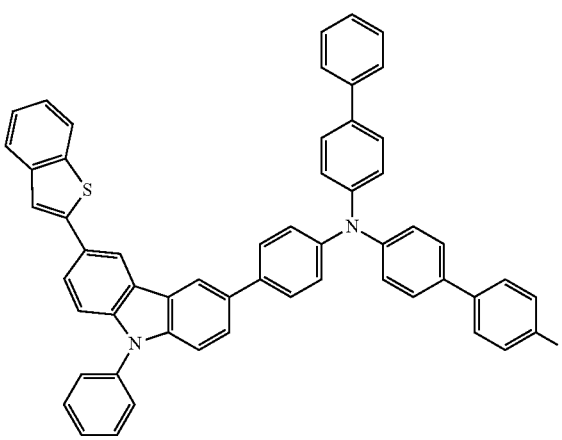
51
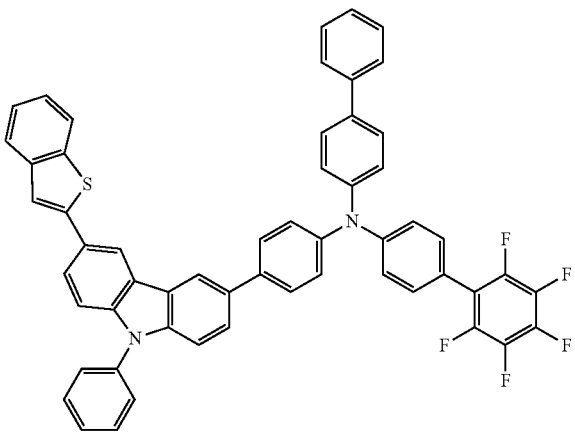
52
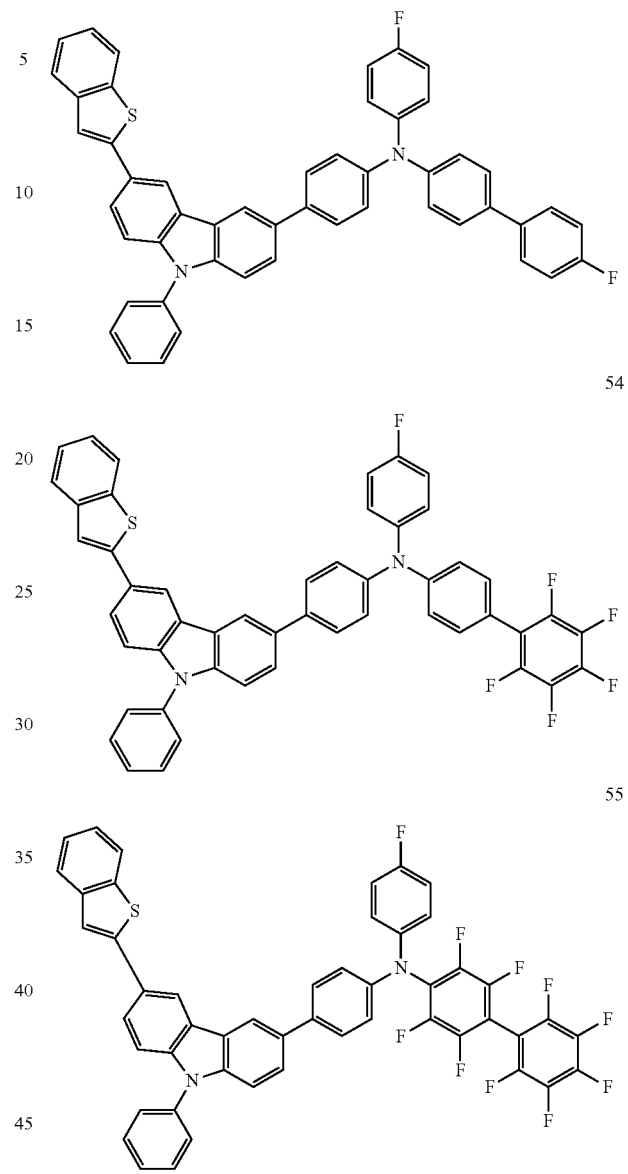
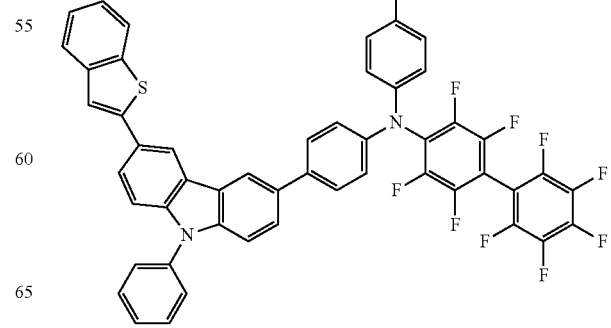

57
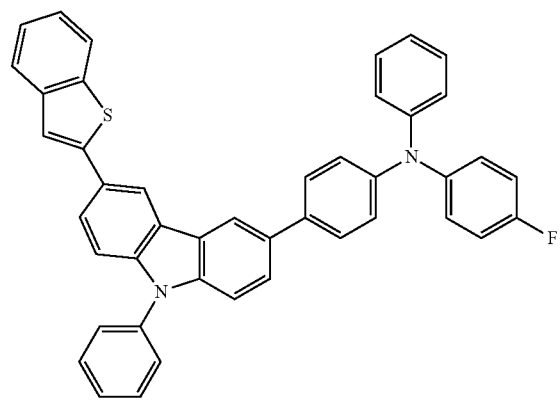
58
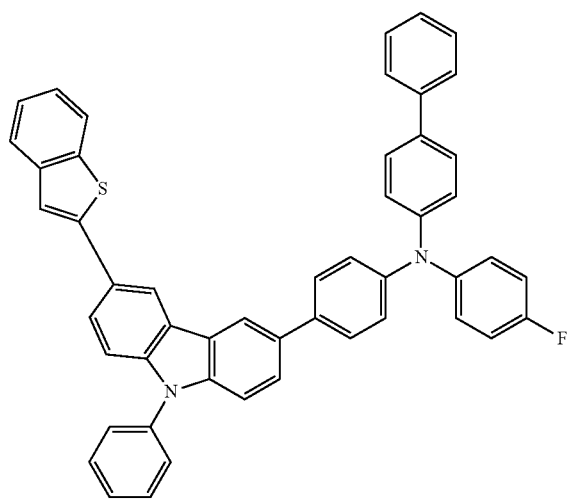
59
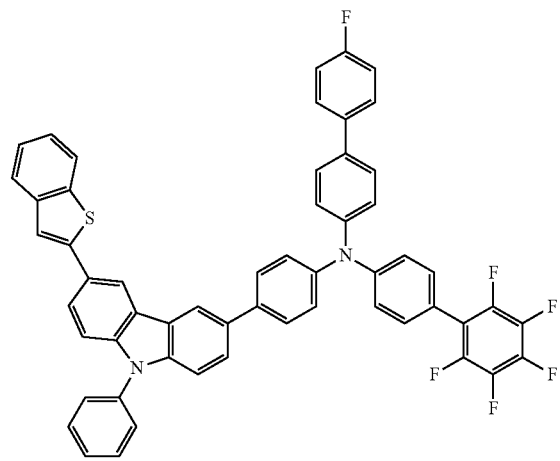
60
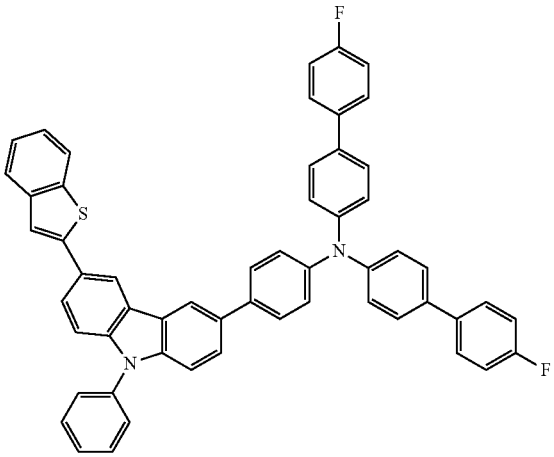
61
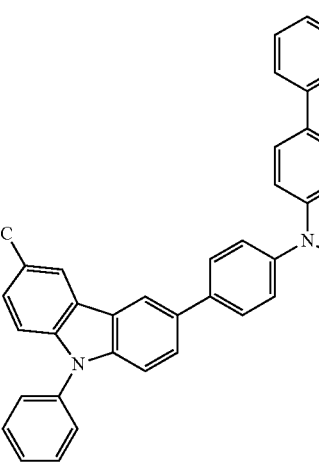
62
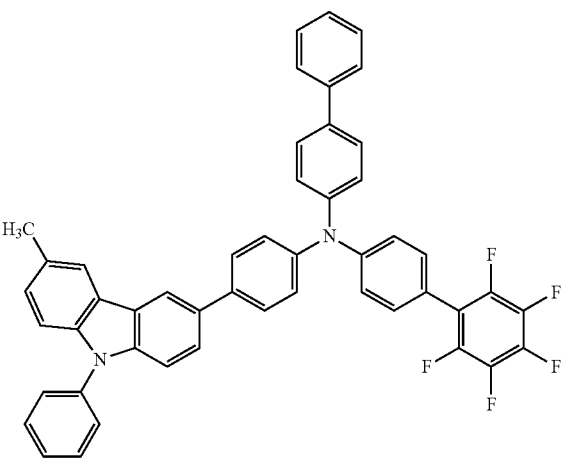

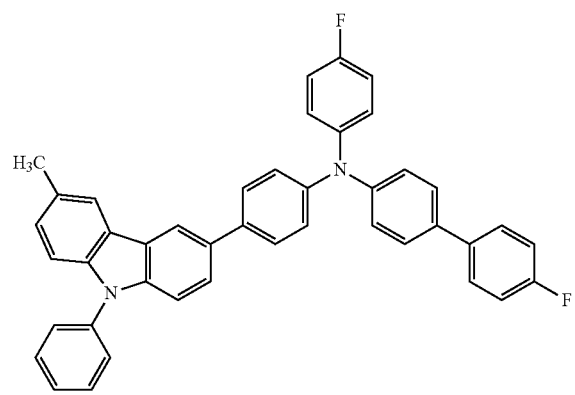
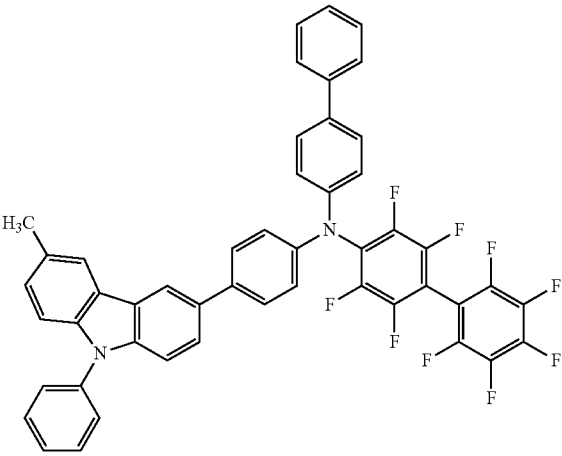
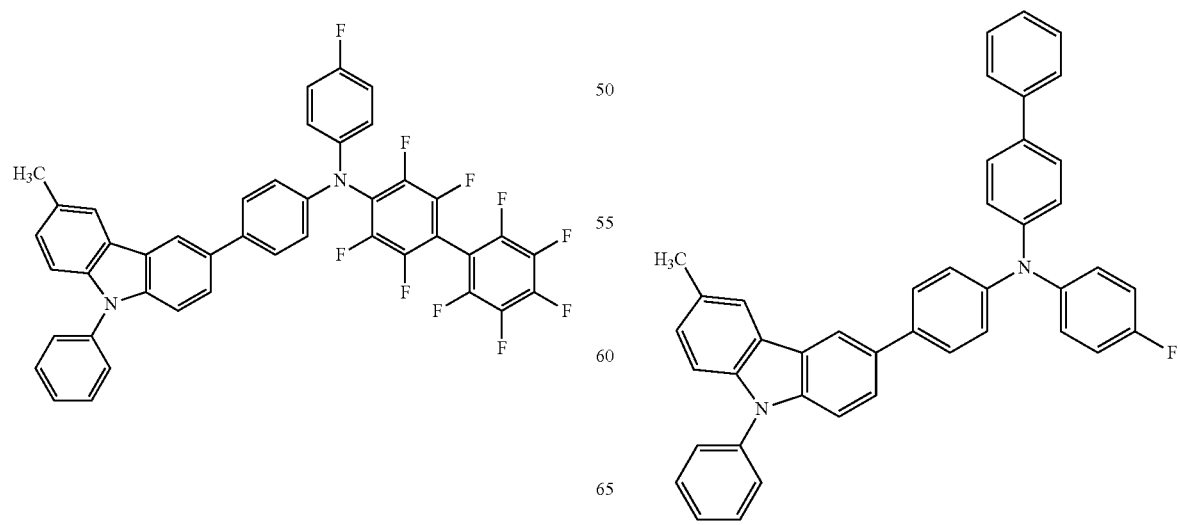

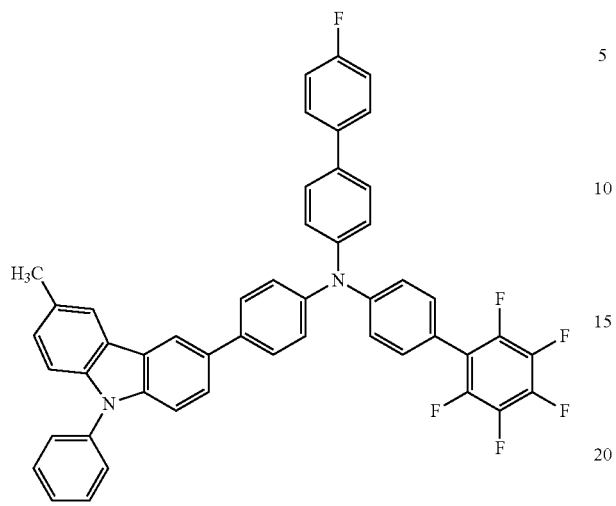
69
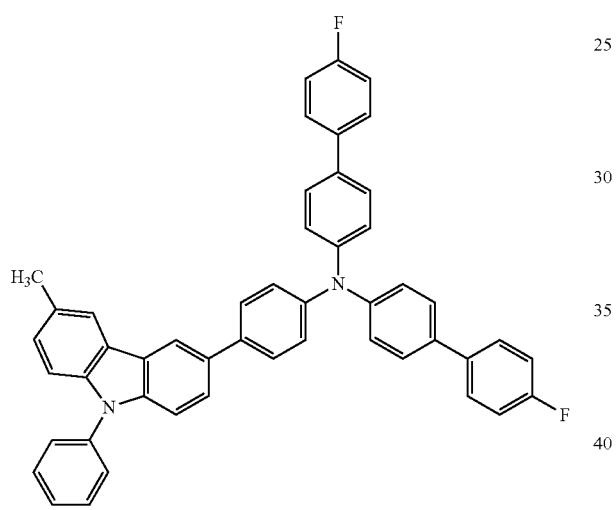
70
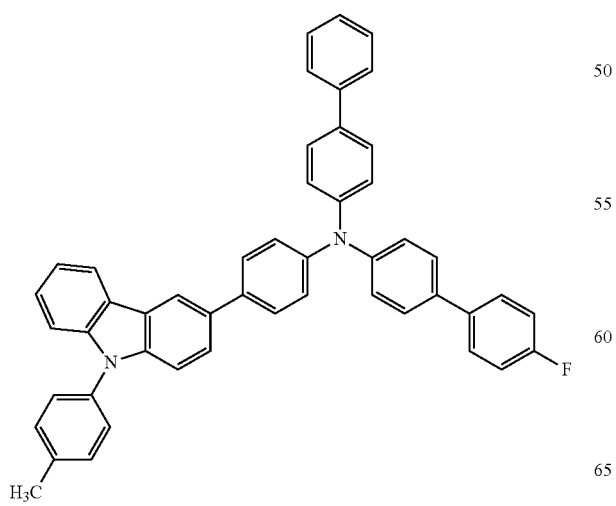
71
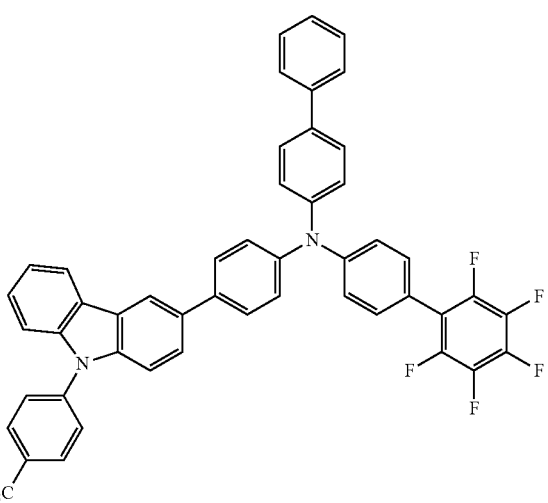
72
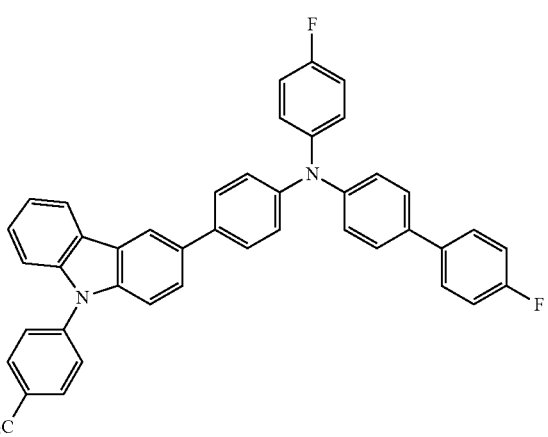
73
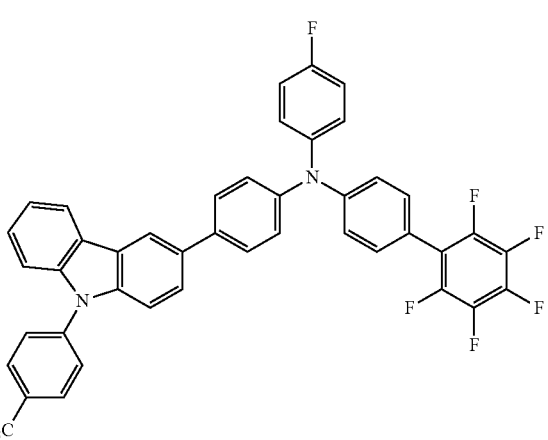
74

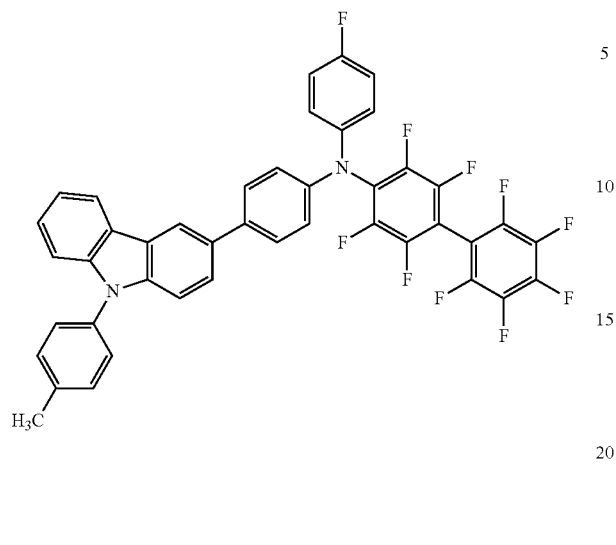
75
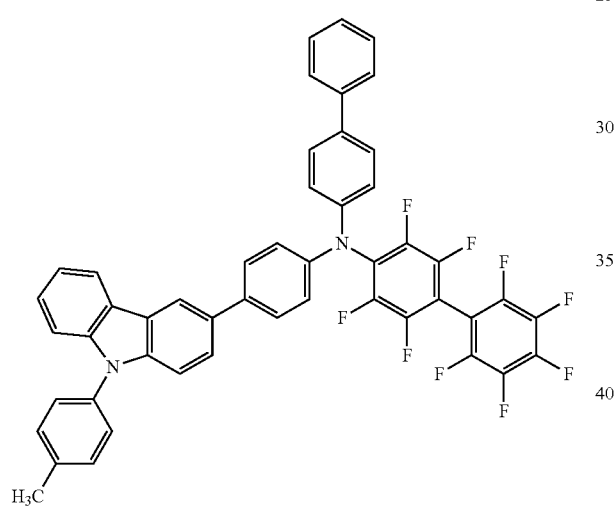
76
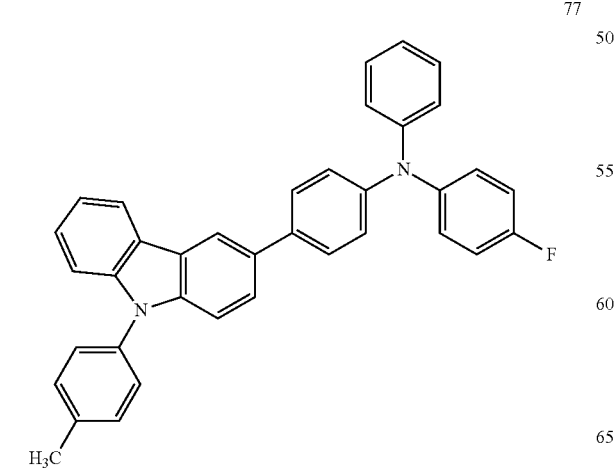
77
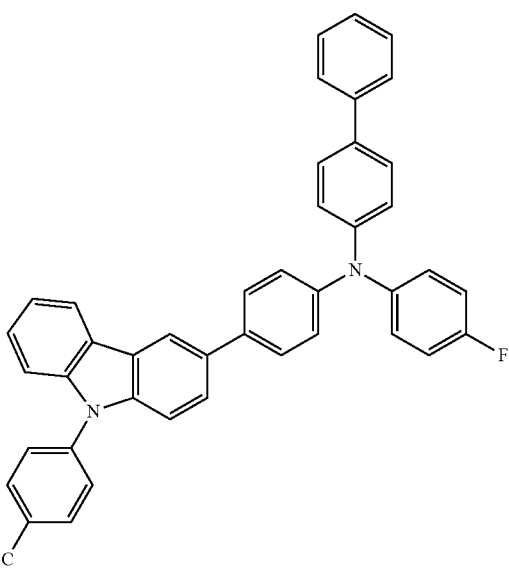
78
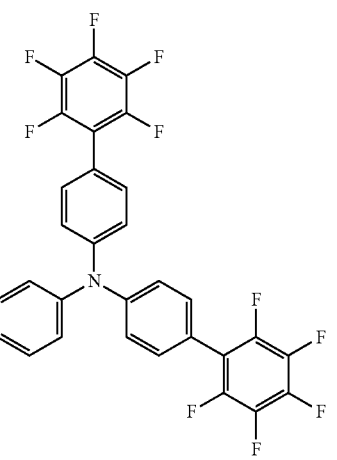
79

80
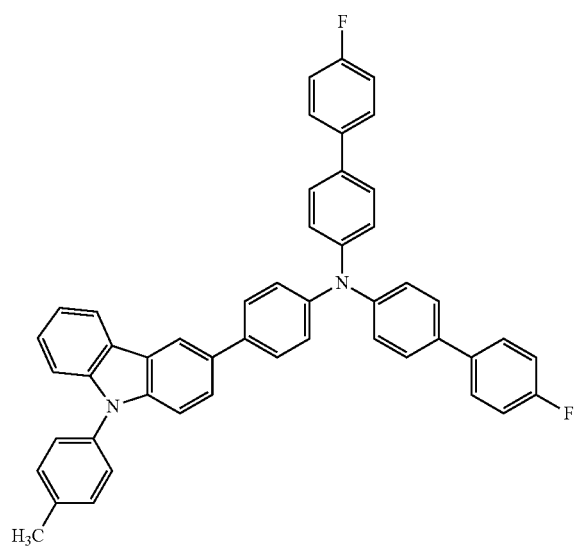
81
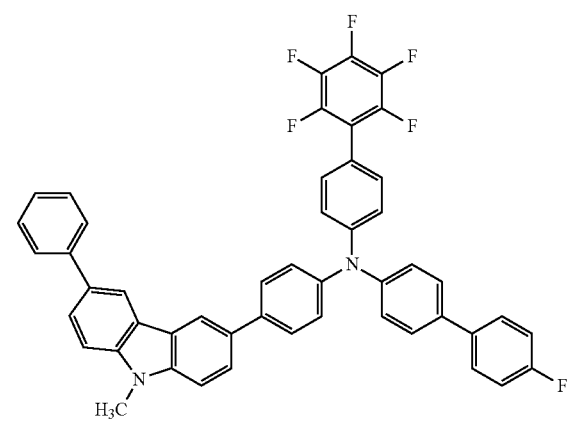
82
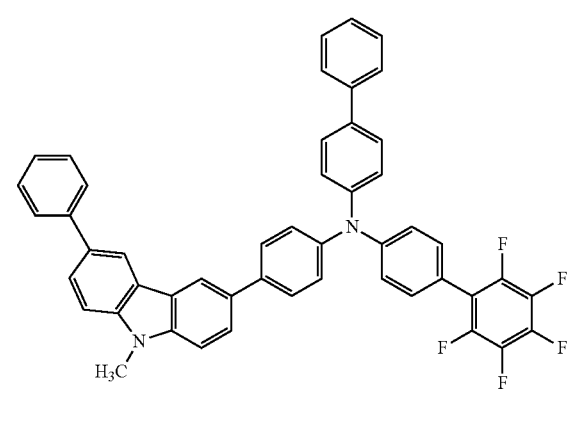
83
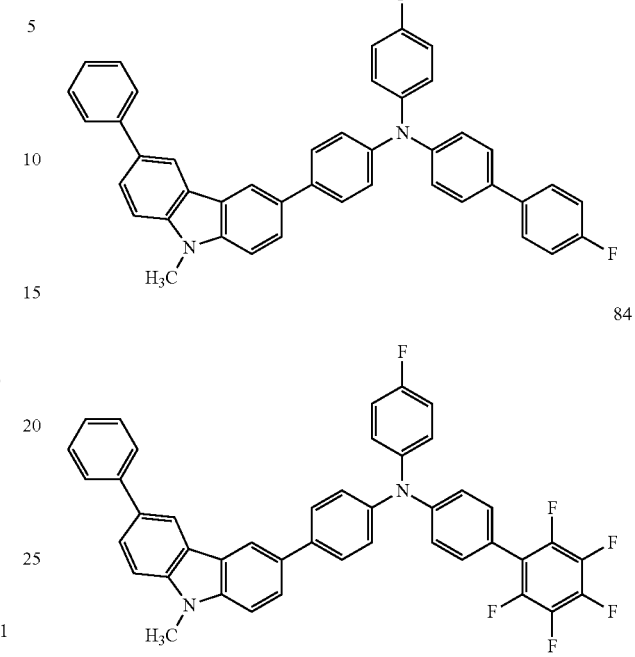
84
85
86
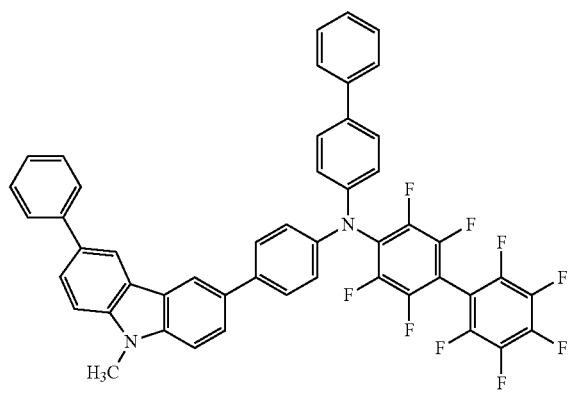

87
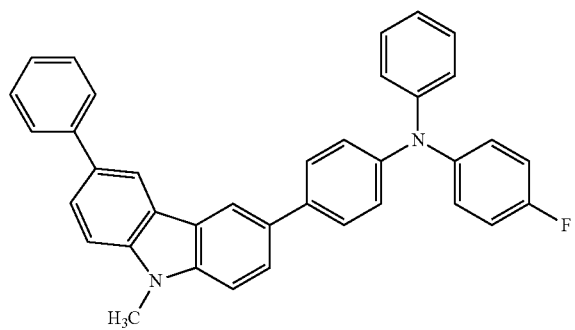
88
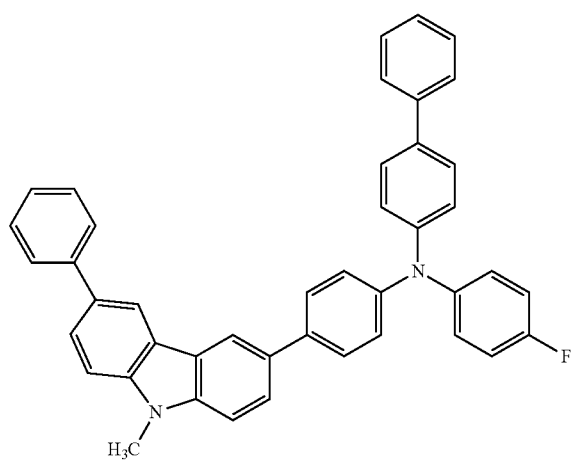
89
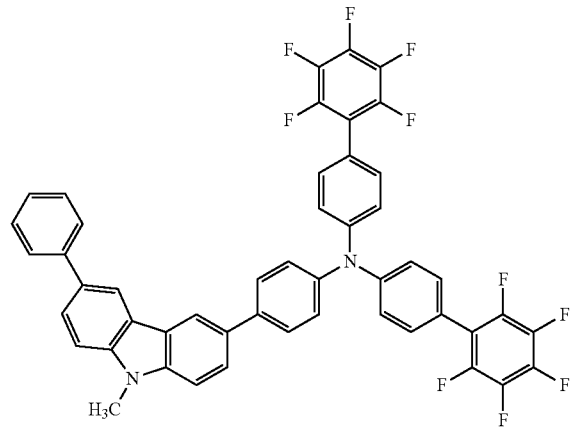
90
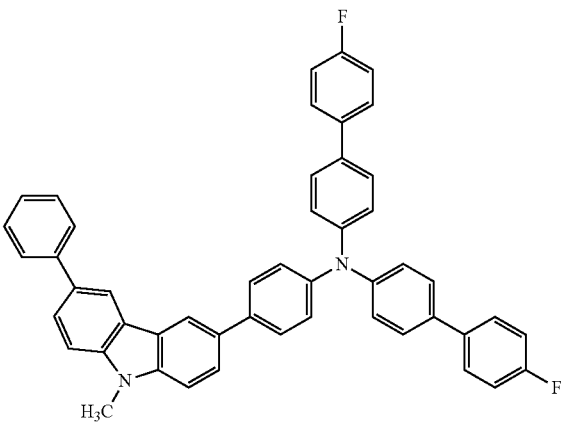
91
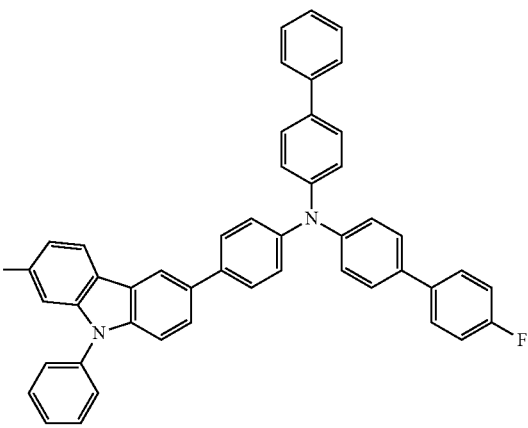
92
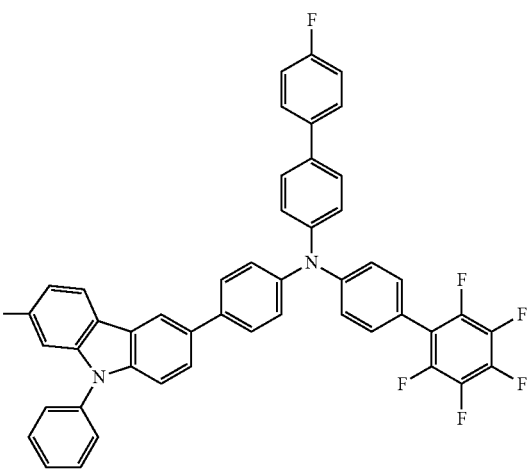

93
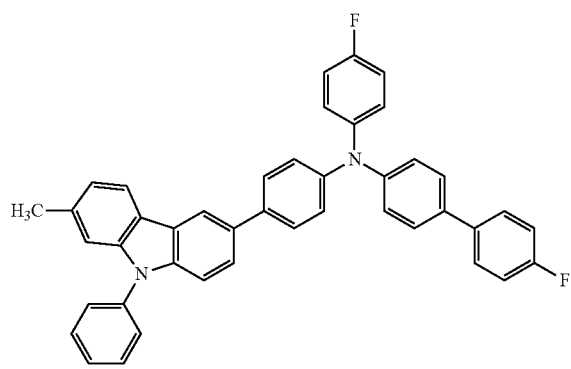
94
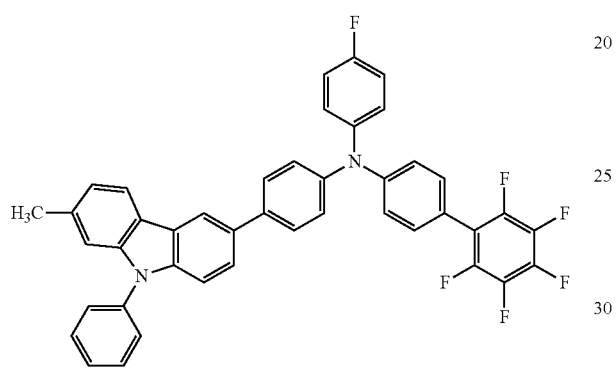
95
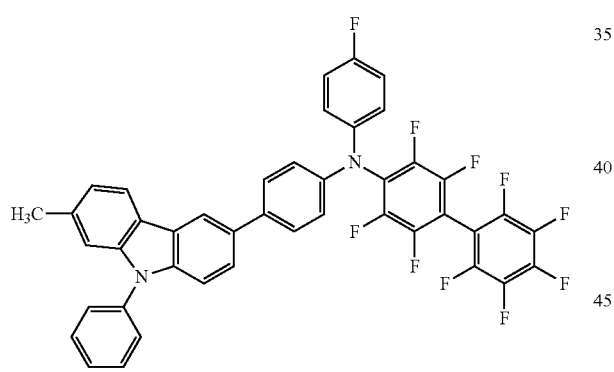
96
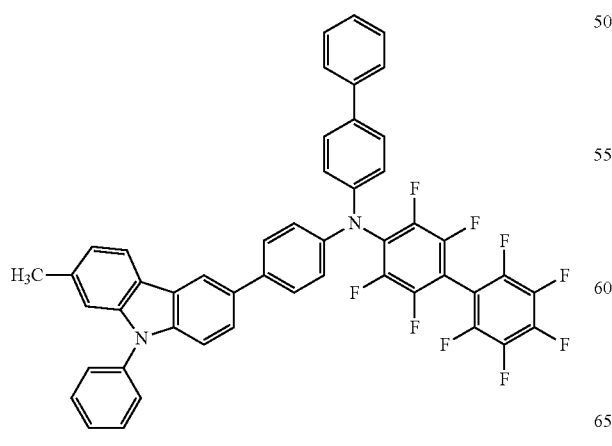
97
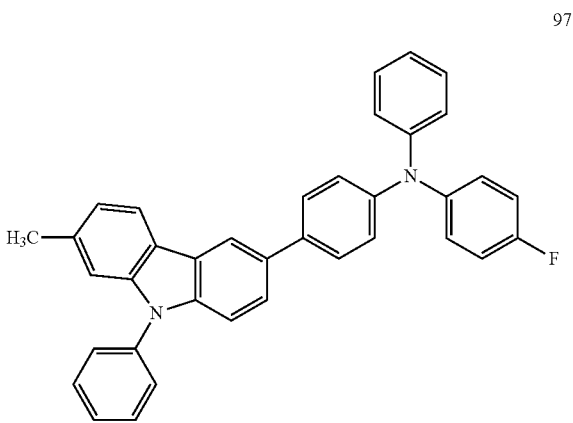
98
99

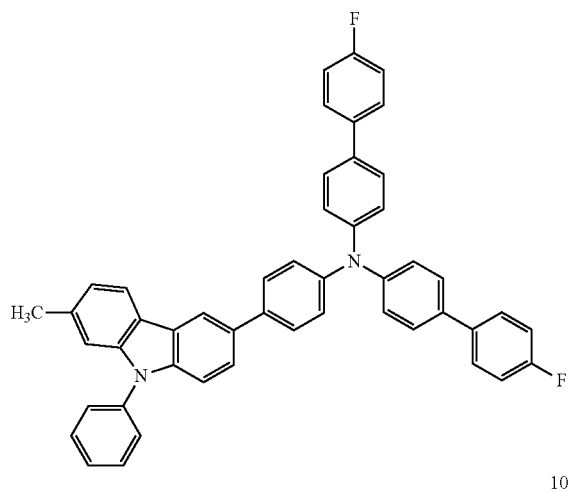
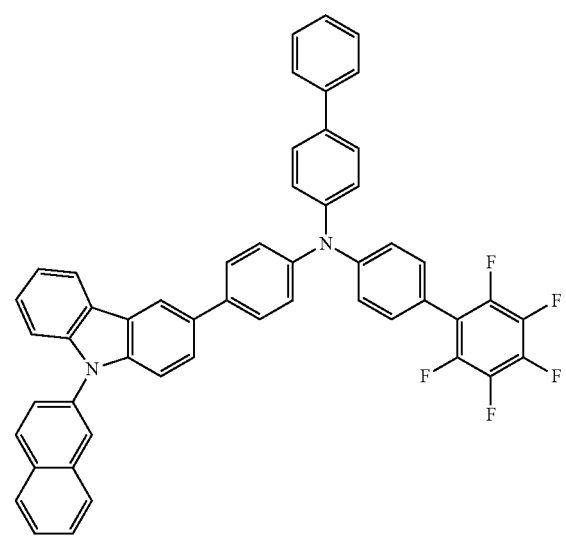
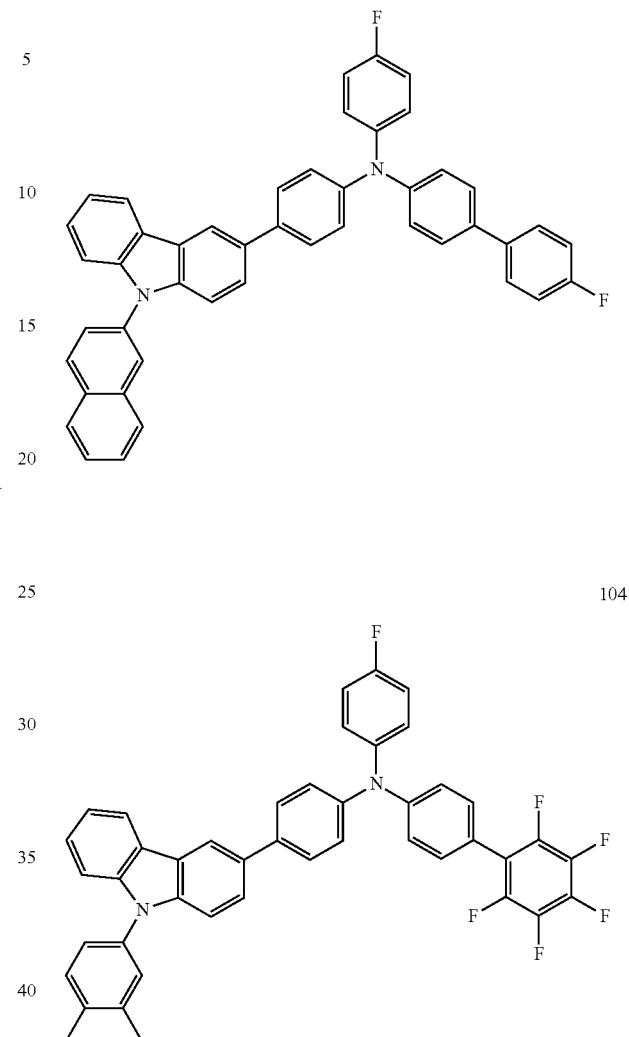

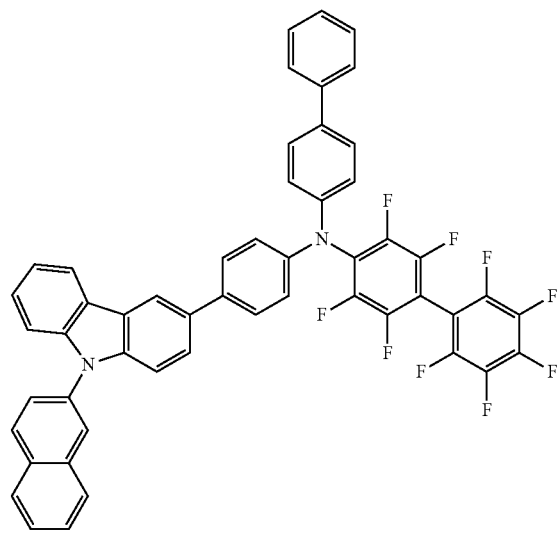
106
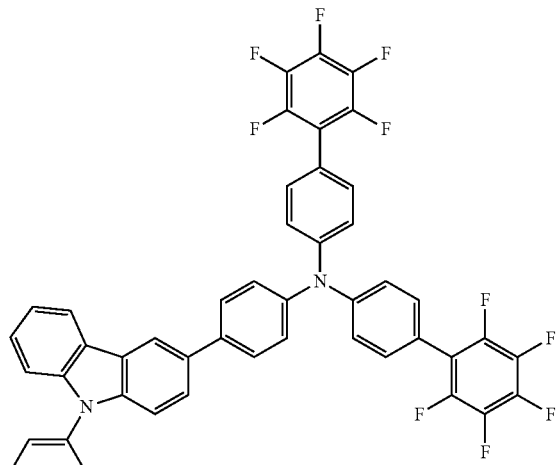
109
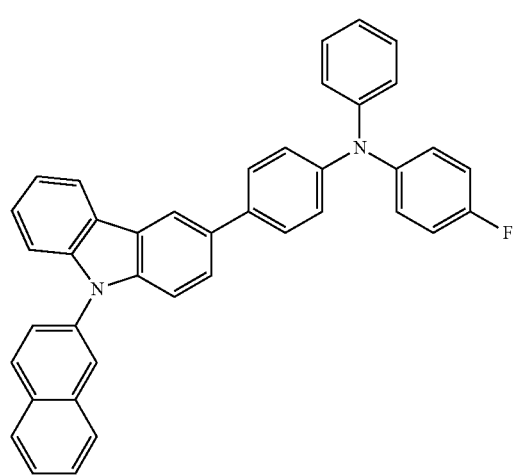
107
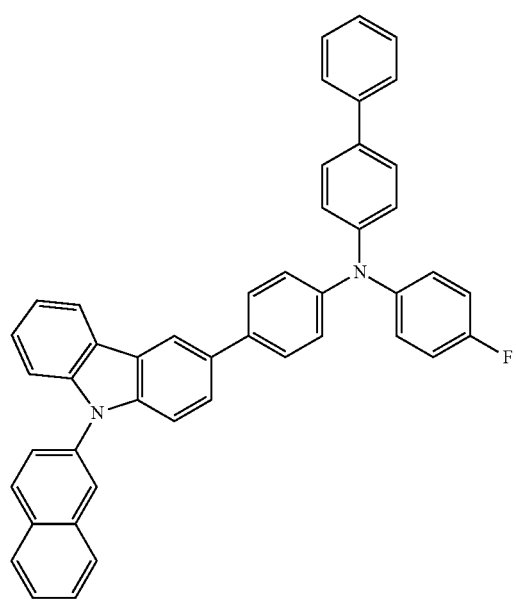
108
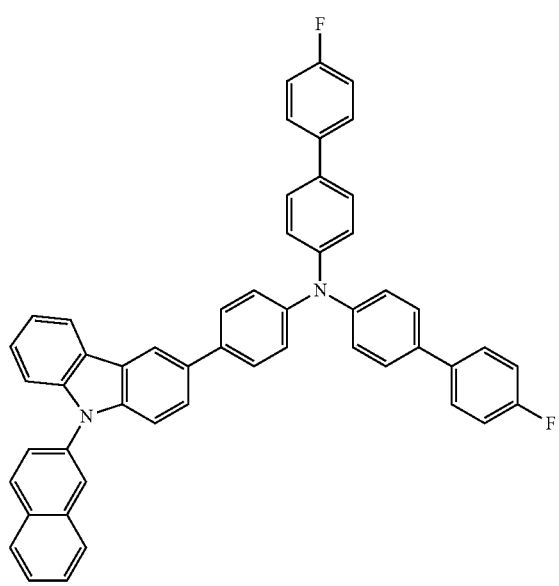
110

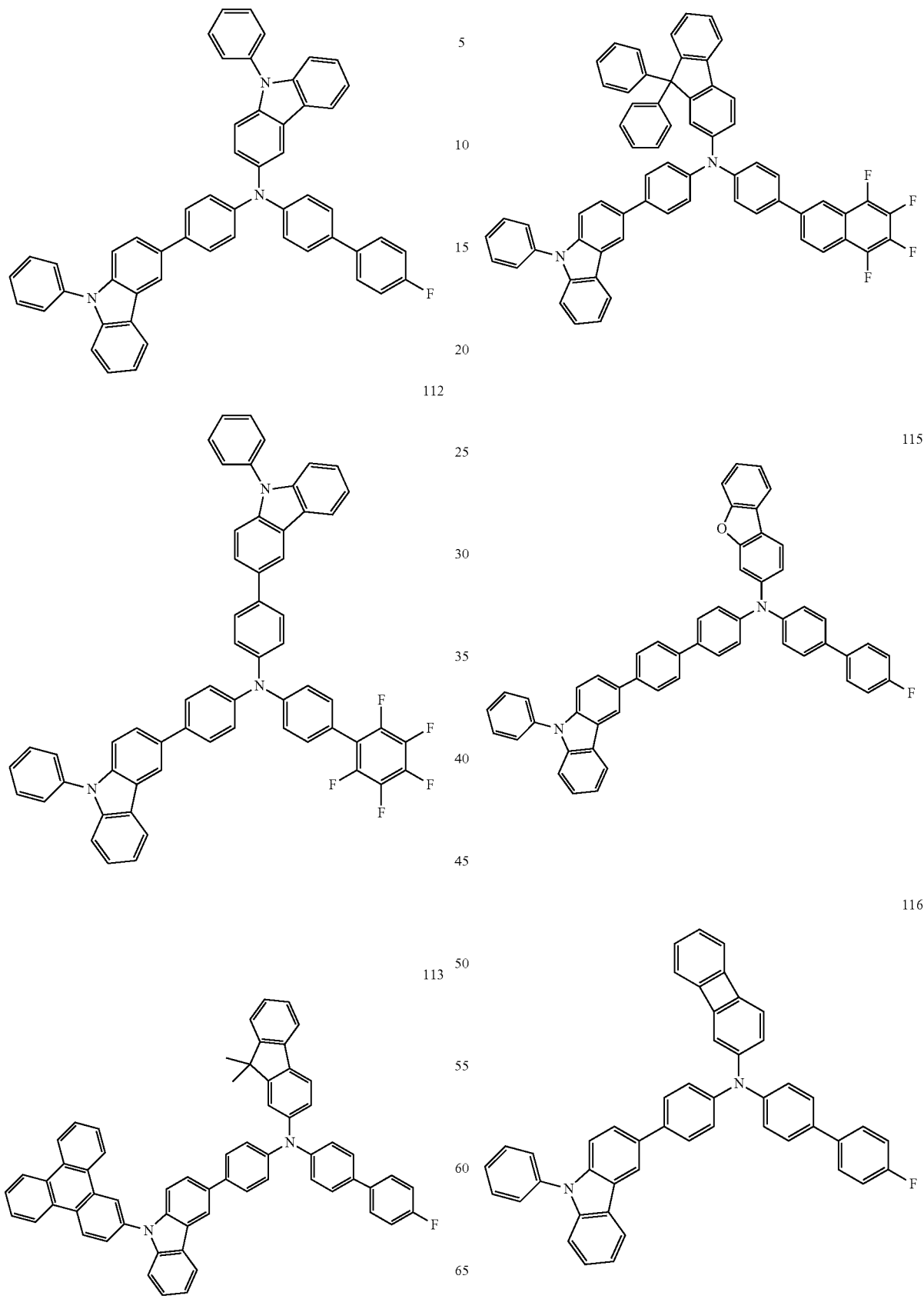

117
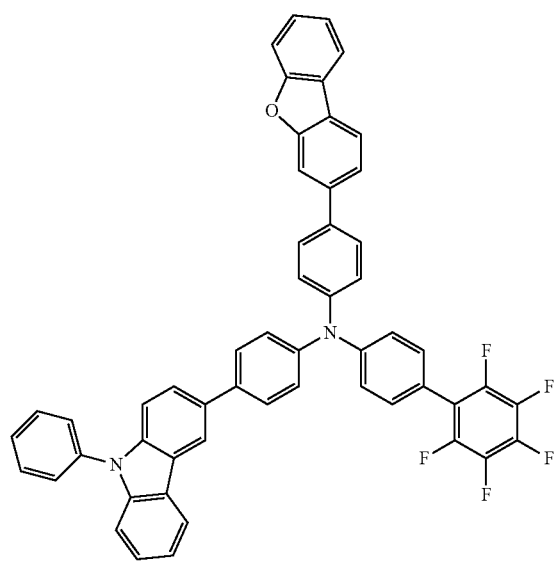
118
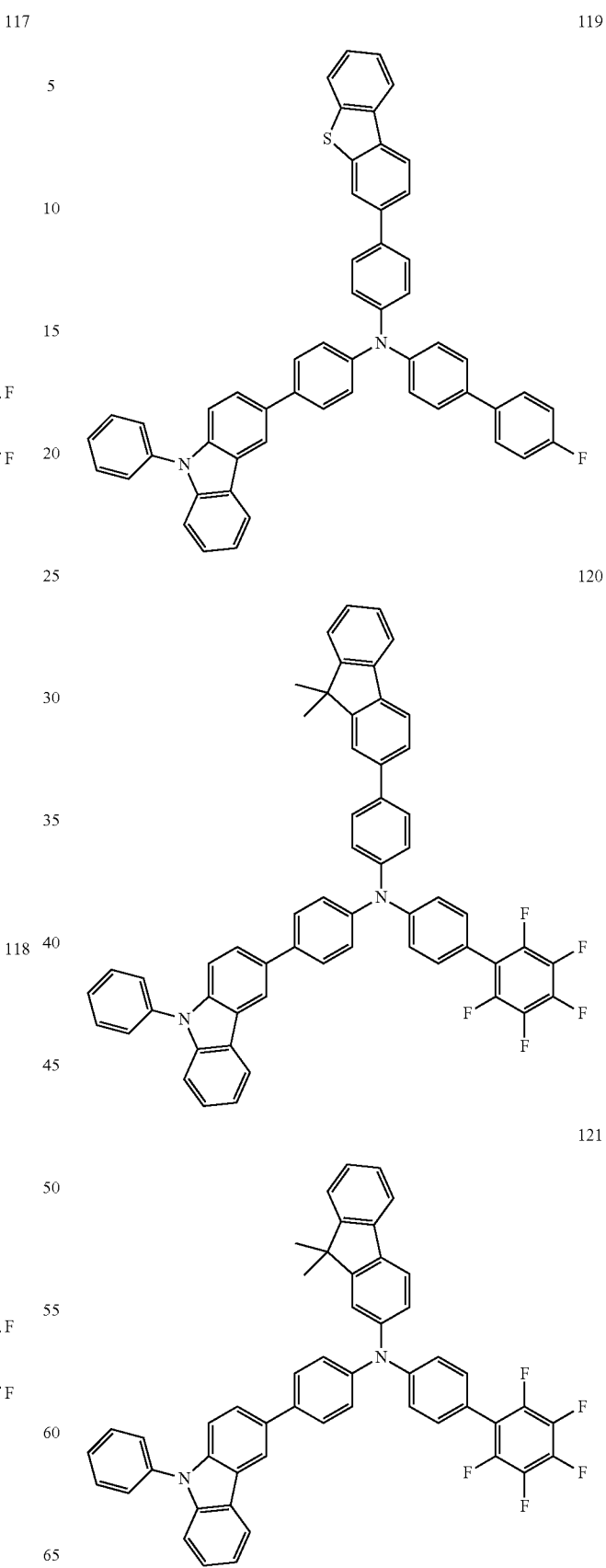

122
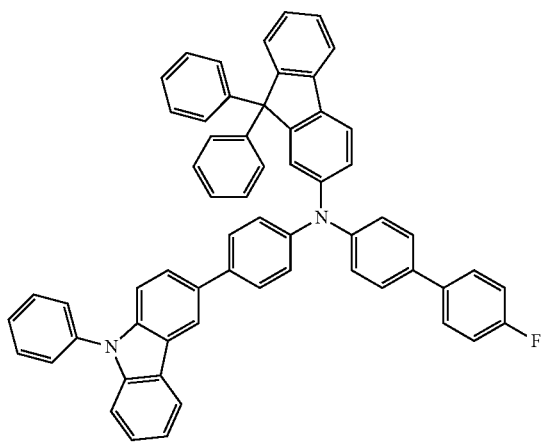
123
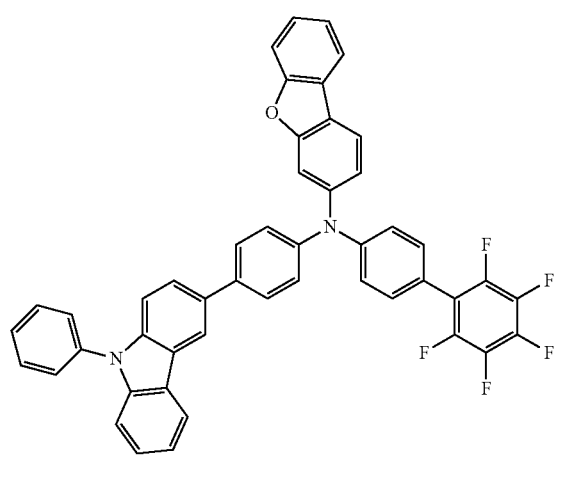
124
125
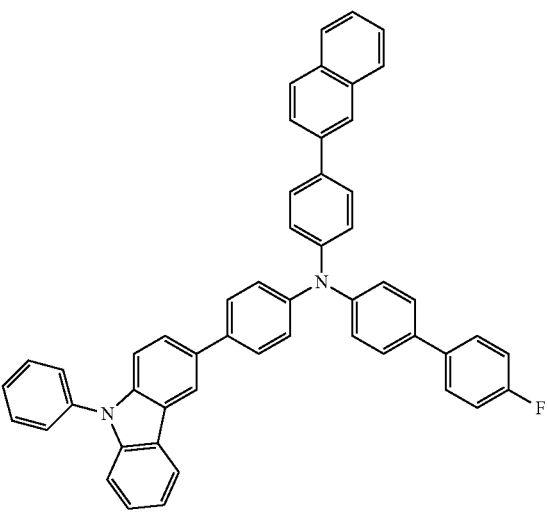
126
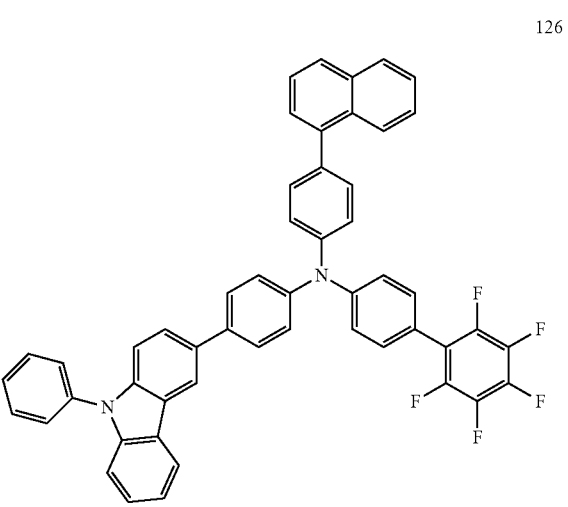
127
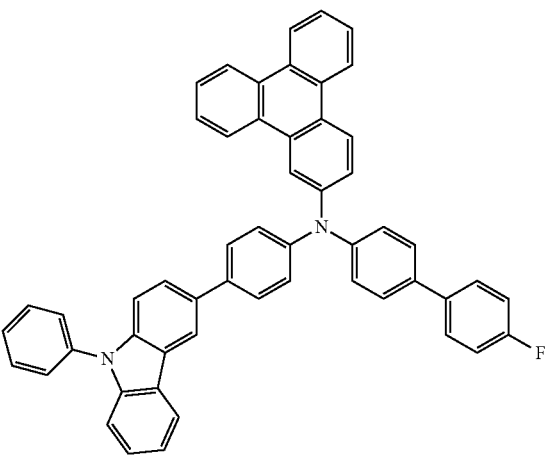

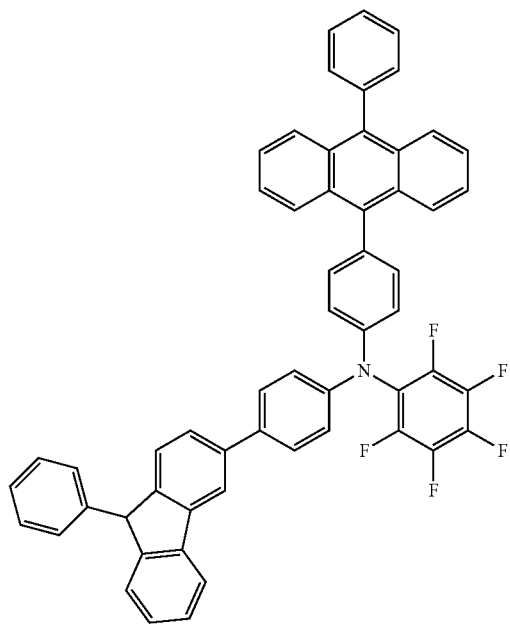
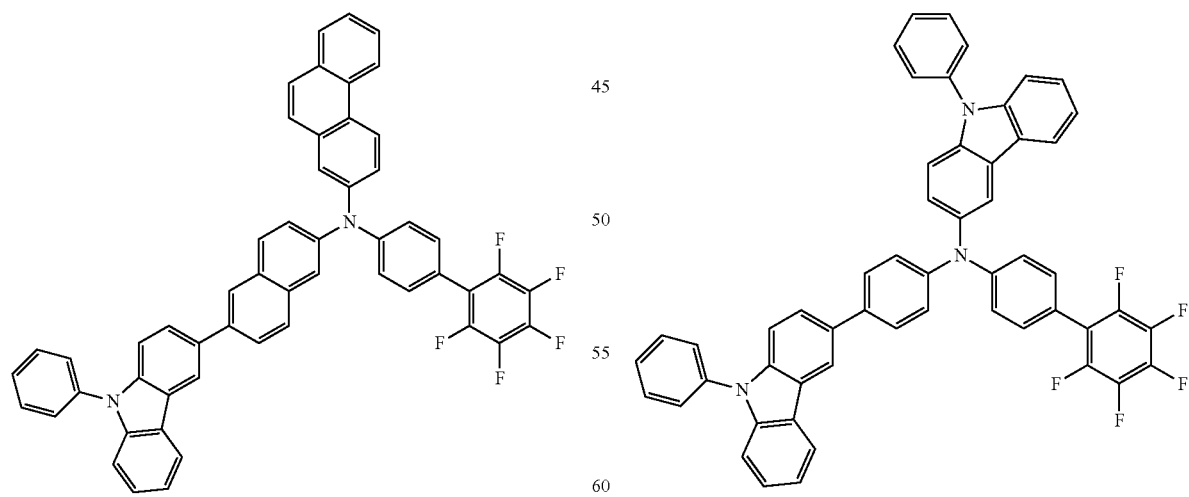

132
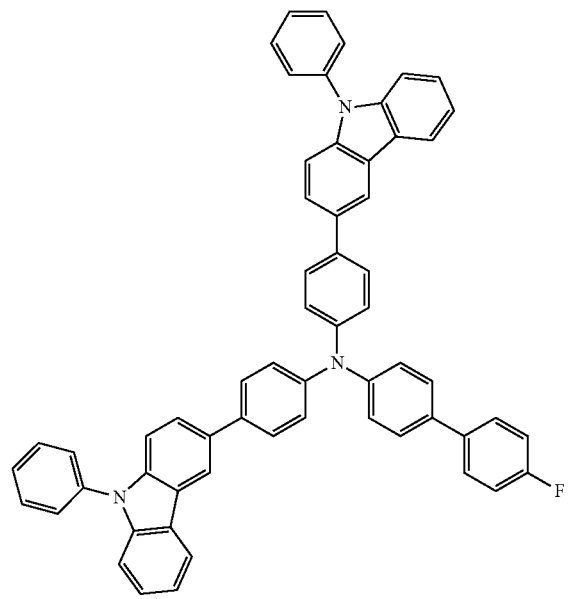
133
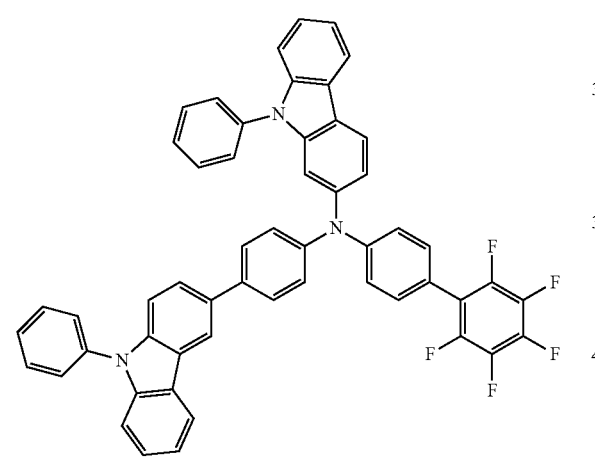
134
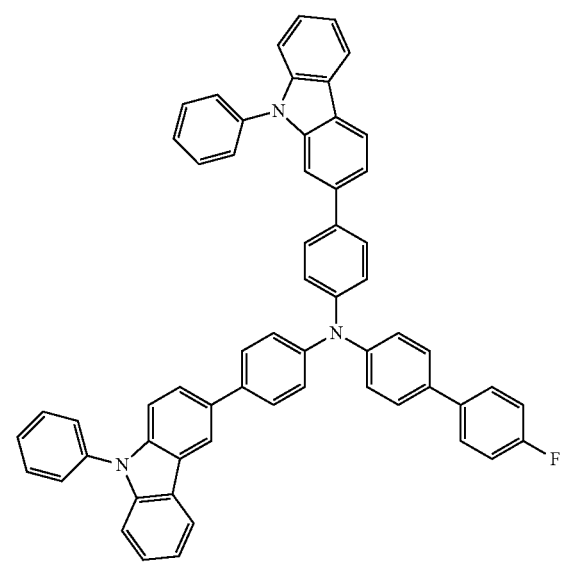
135
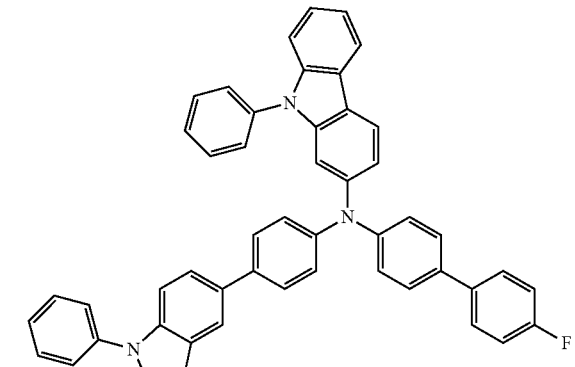
136
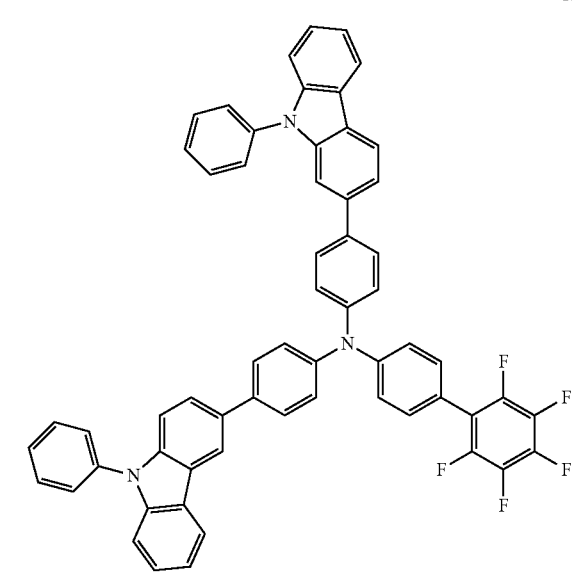
137
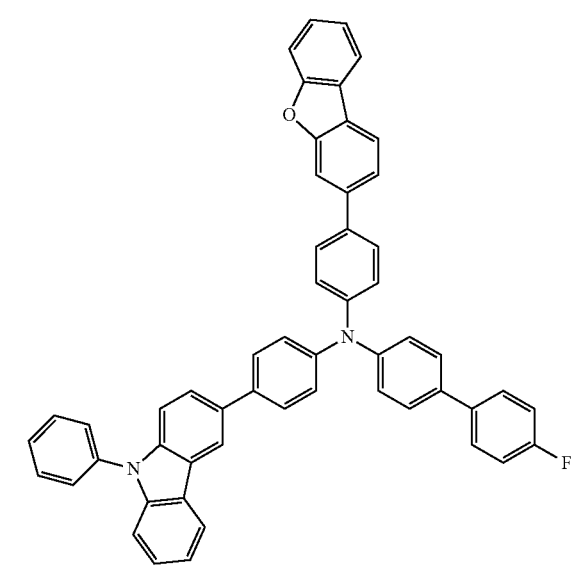

138
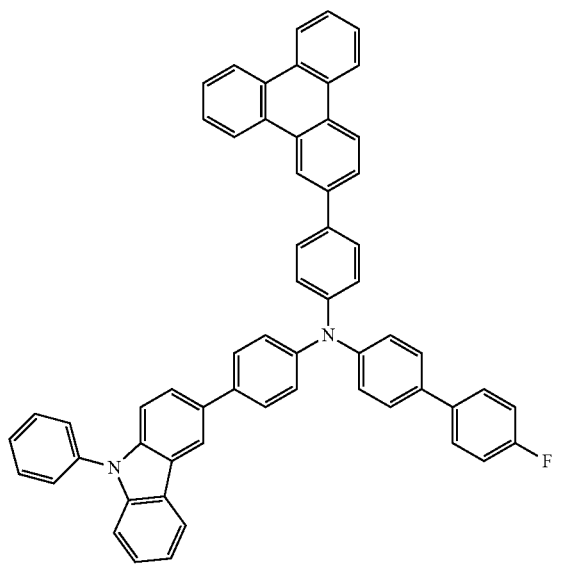
139
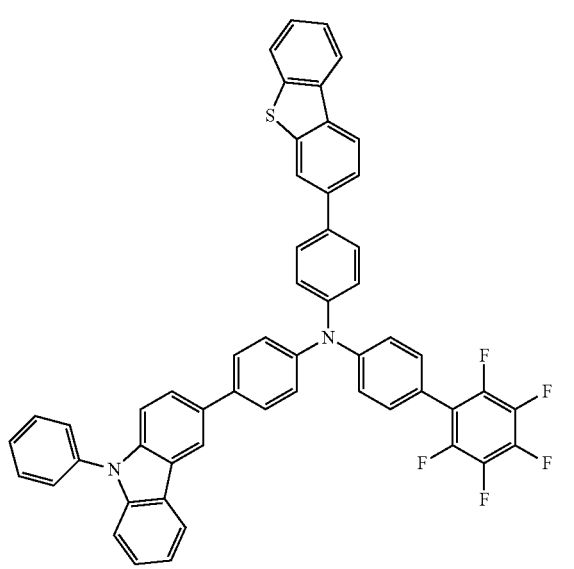
140
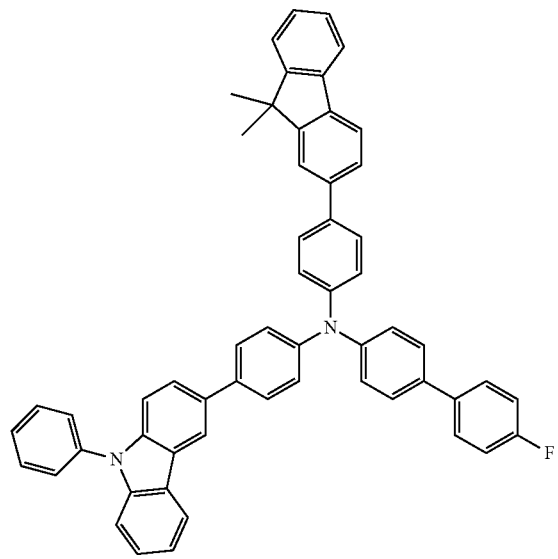
141
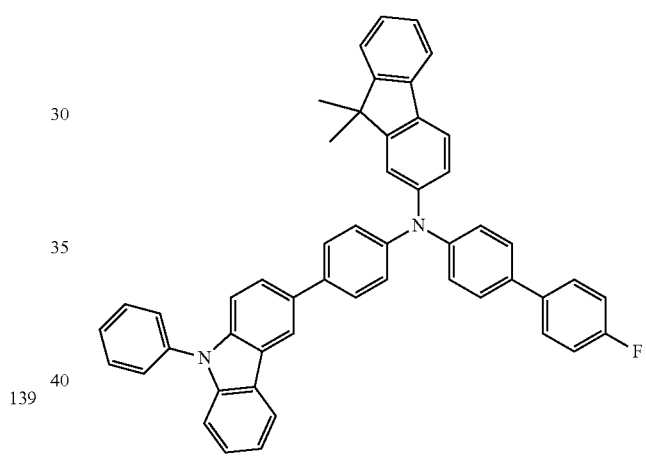
142
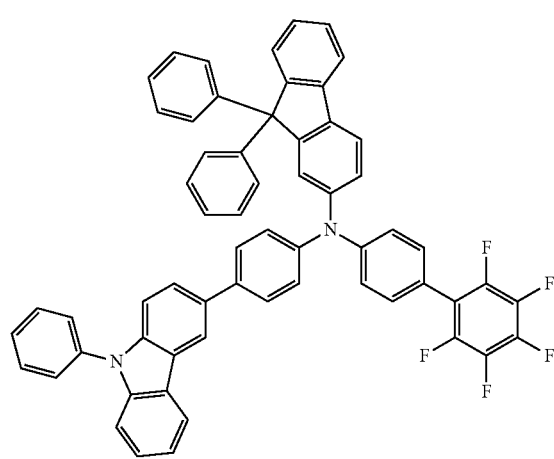

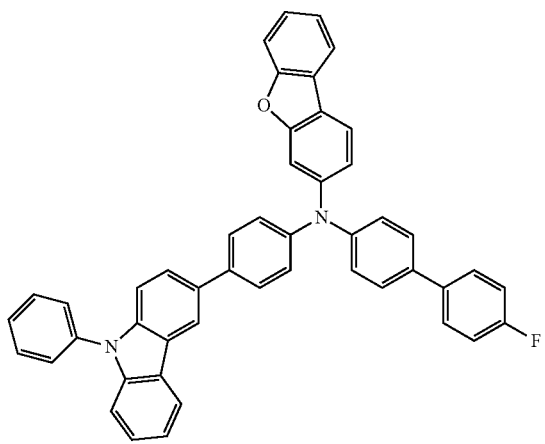
143
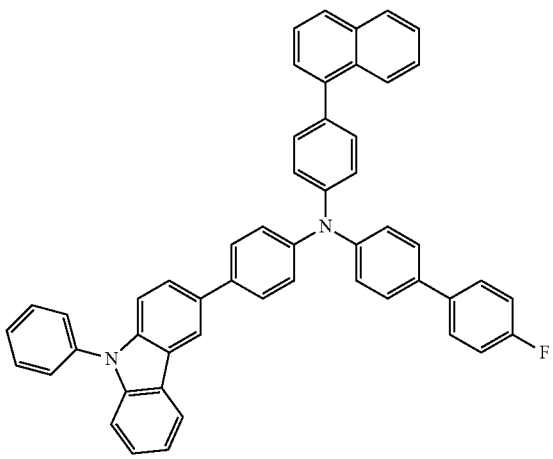
146
144
147
145
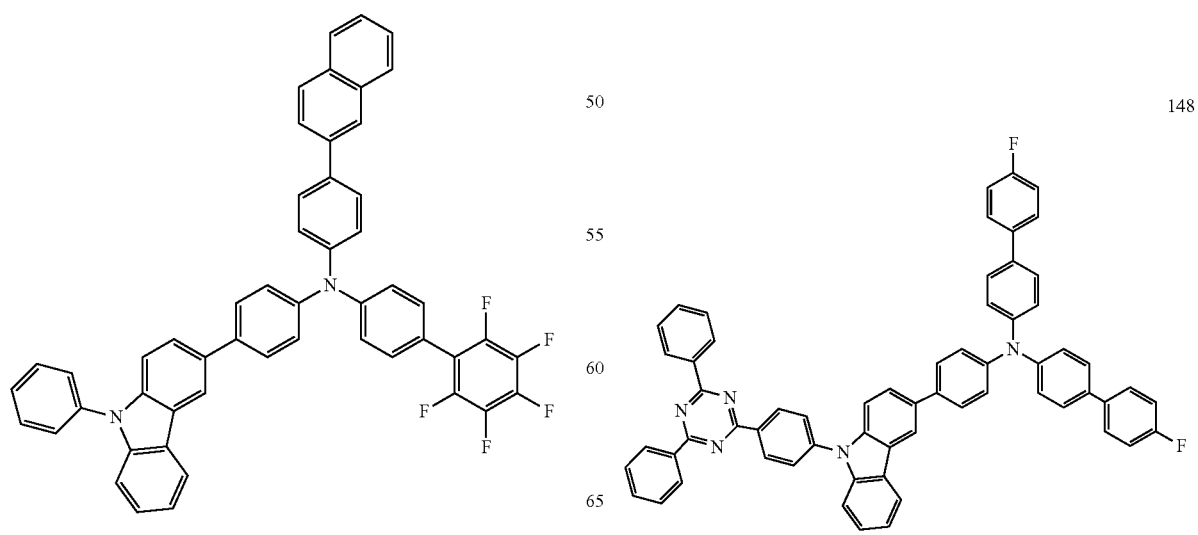
148

149
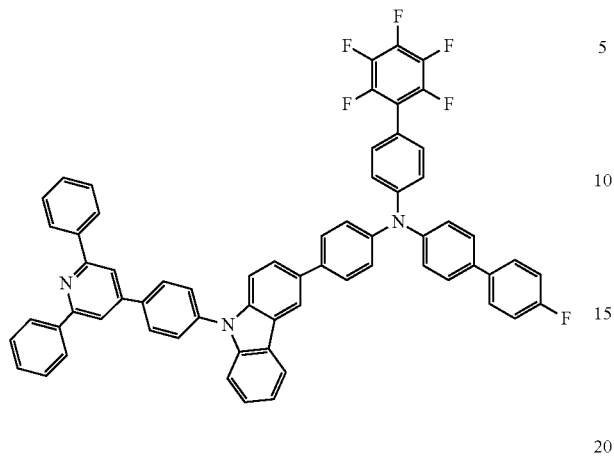
150
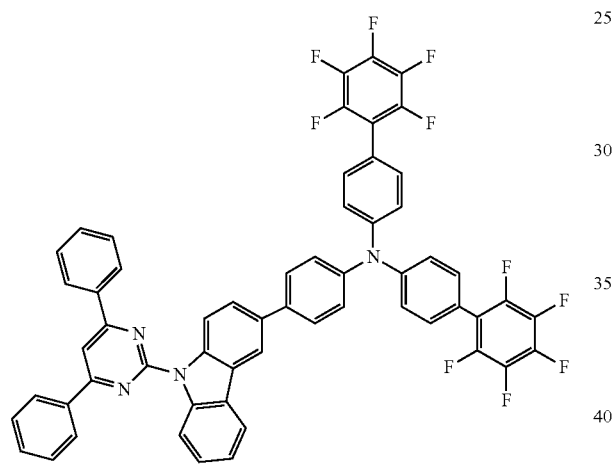
151
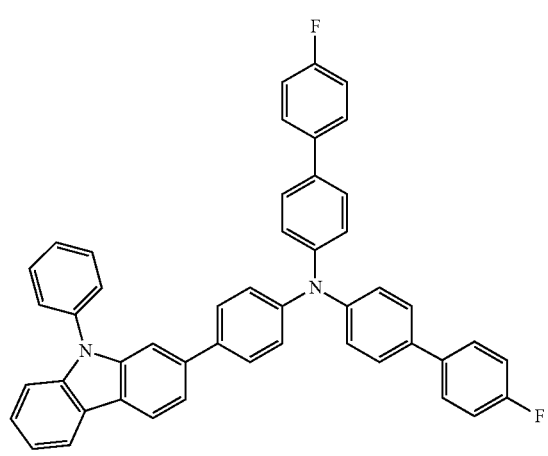
152
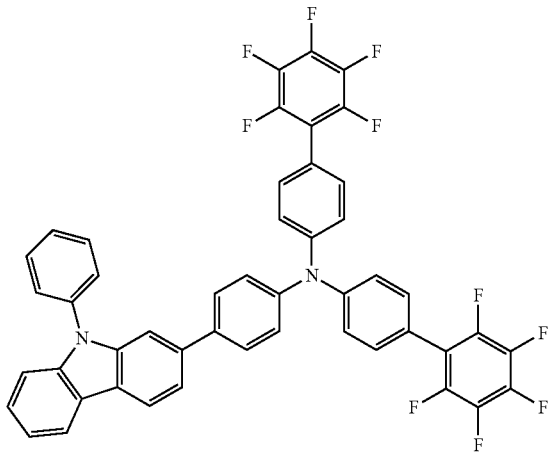
153
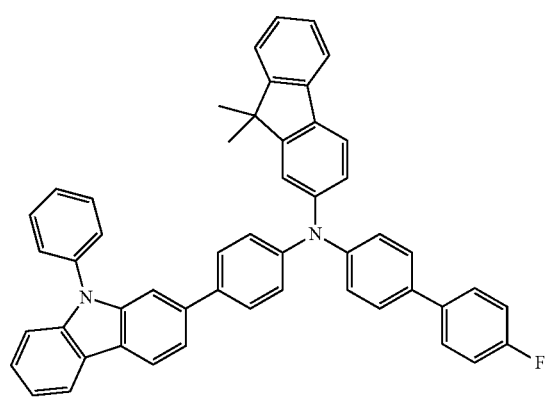
154
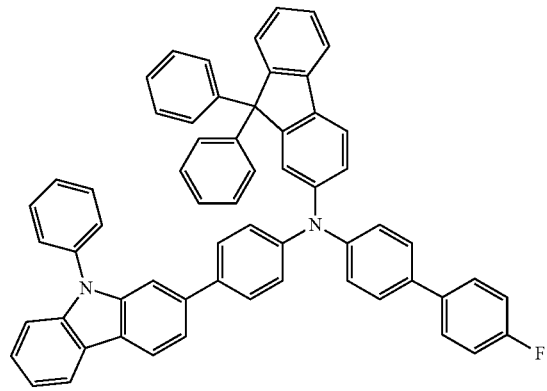

155
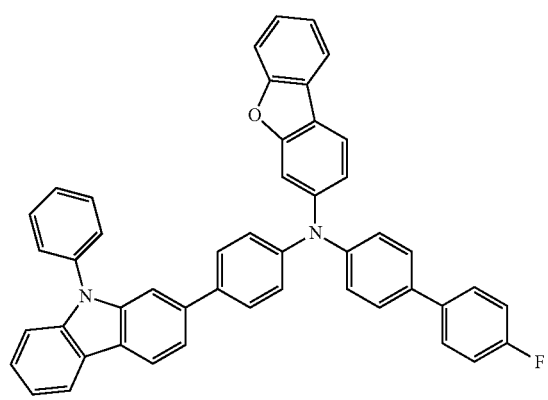
156
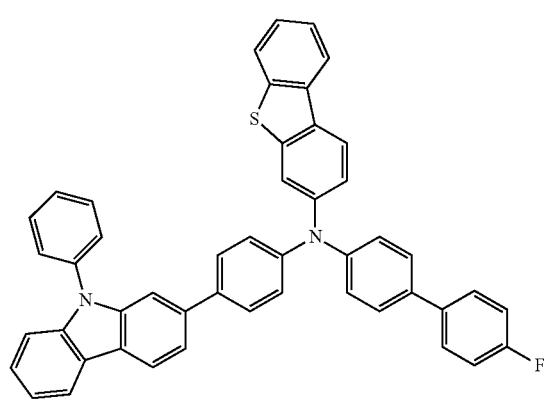
157
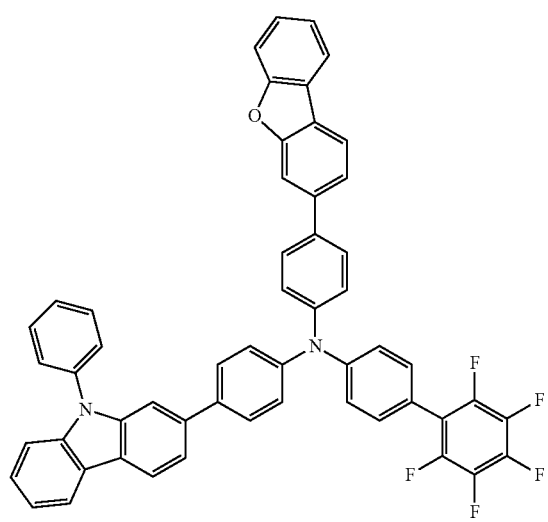
158
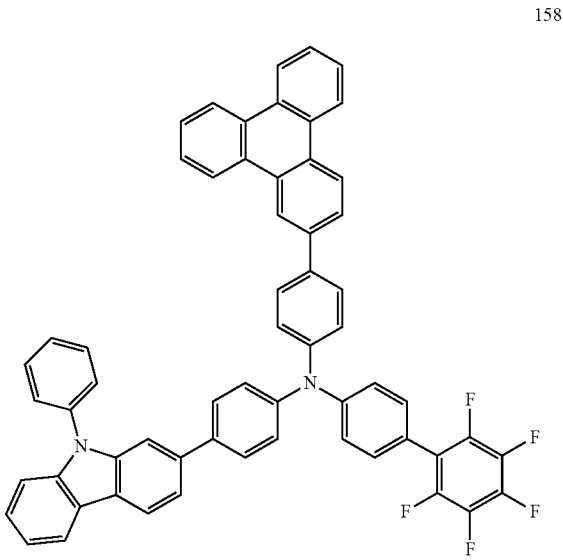
159
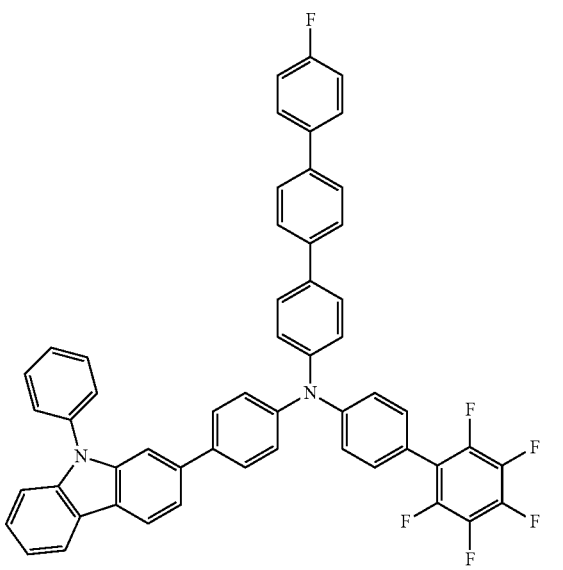
160
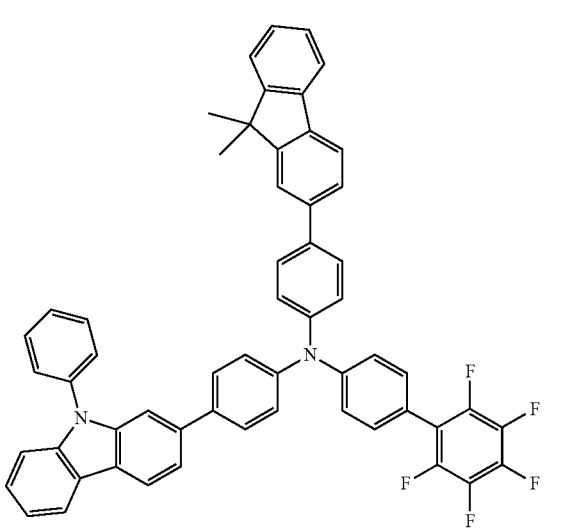

161
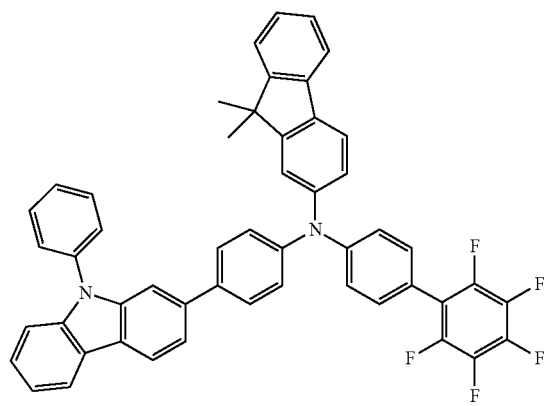
162
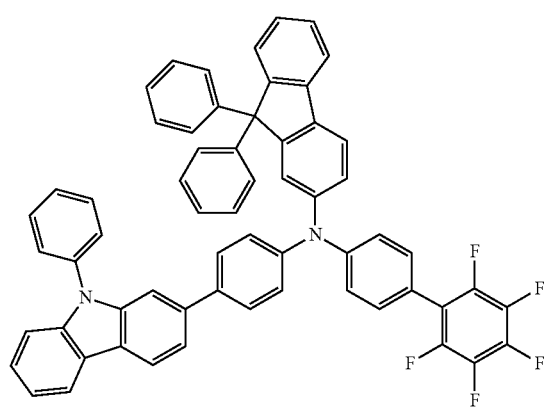
163
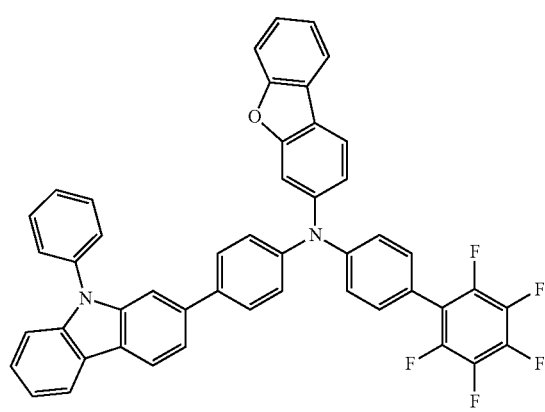
164
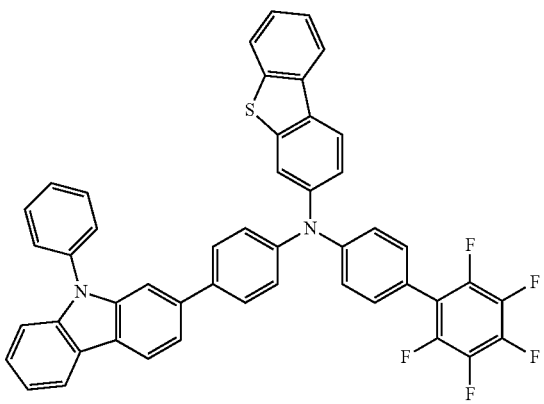
165
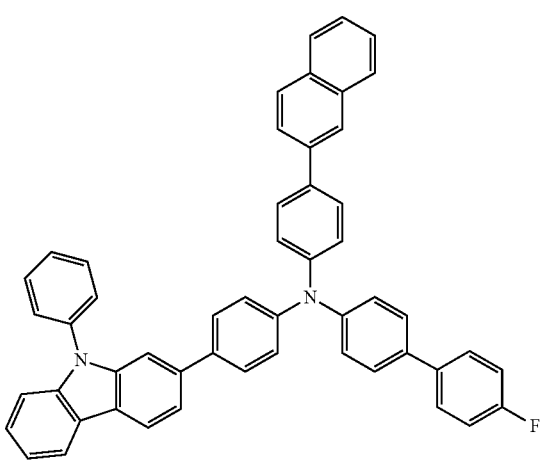
166
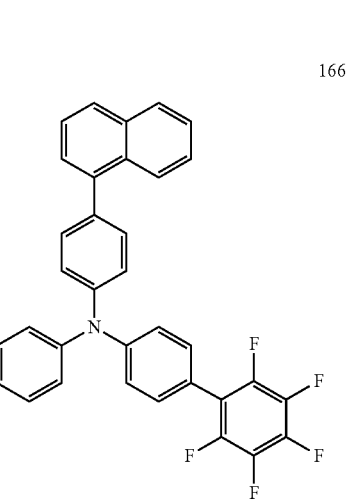

-continued
167
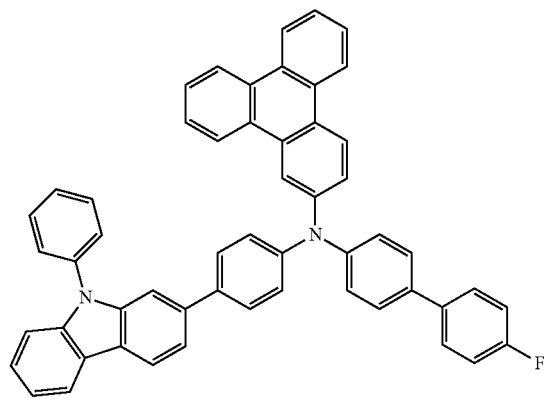
168
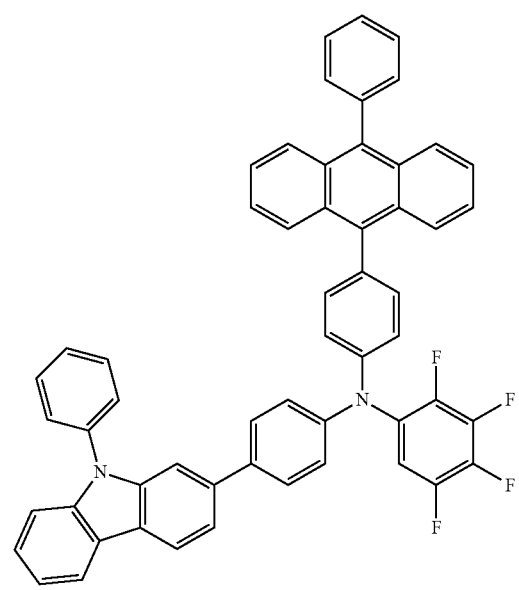
169
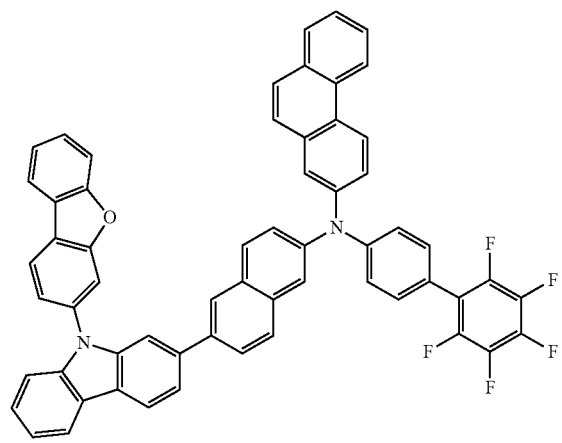
-continued
170
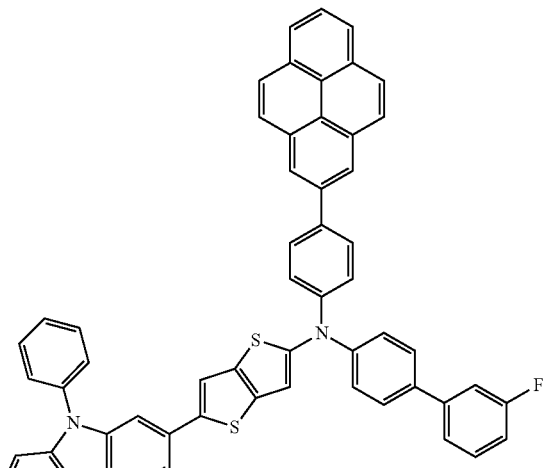
171
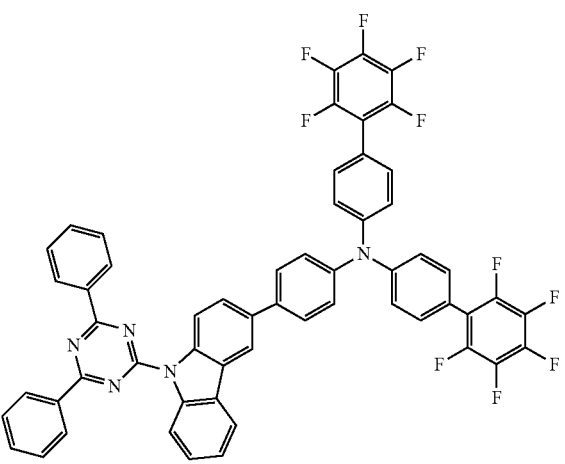
172
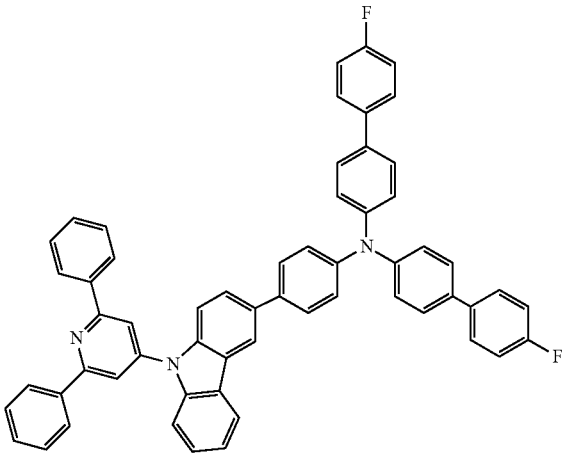

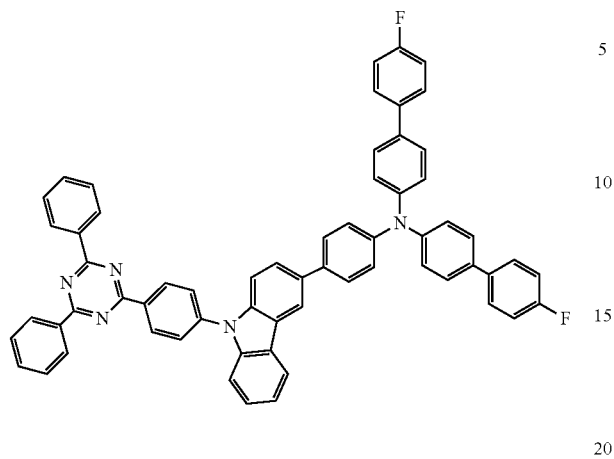
173
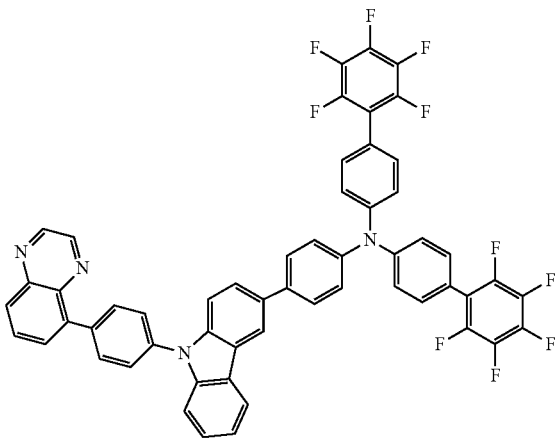
176
174
177
175
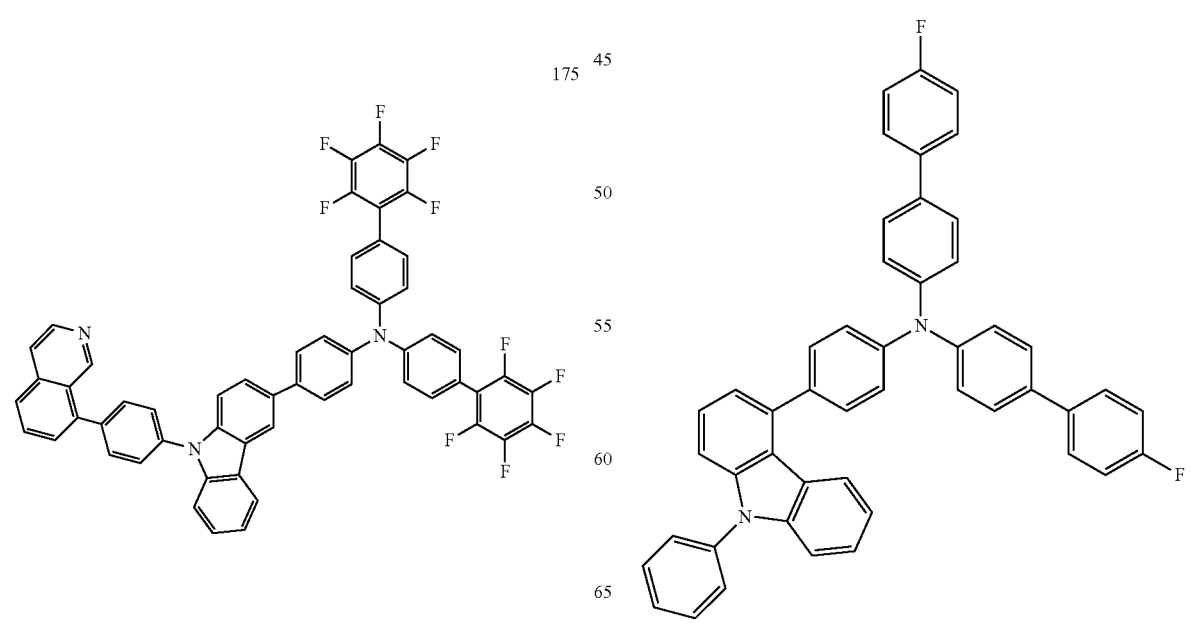
178

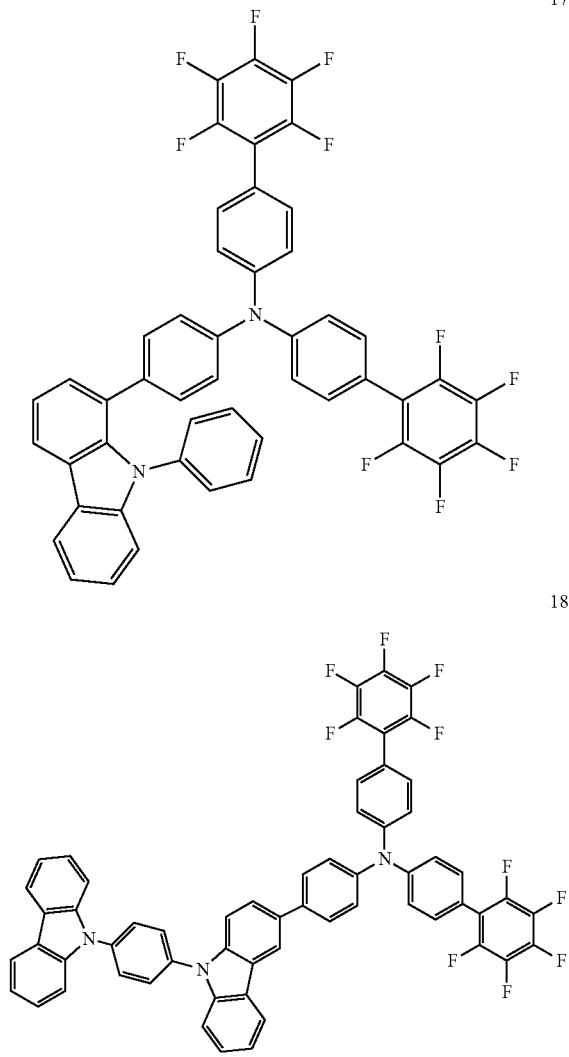

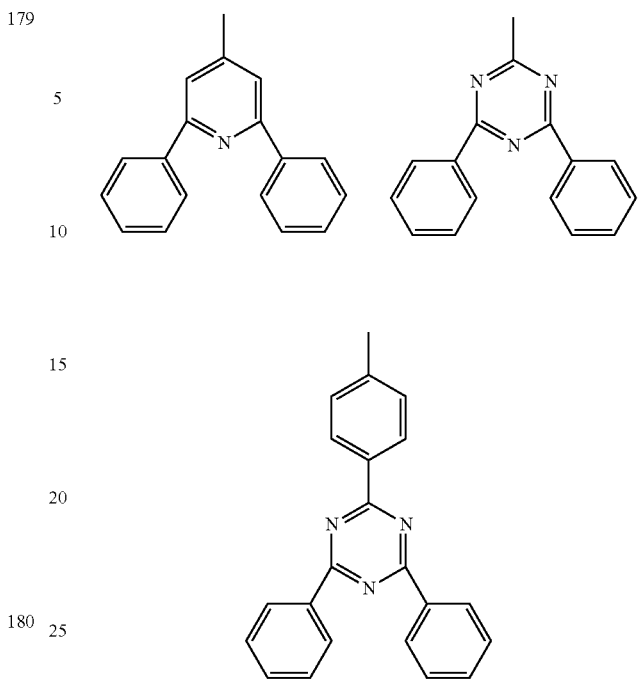

Even though the above explanation is concerned with the use of the amine derivative including the aryl group according to embodiments as an organic EL material of an organic EL device, in other implementations, the use of the amine derivative including the aryl group may be expanded to an organic electronics material or an organic electronics device.

With respect to the amine derivative including a fluorine substituted aryl group according to embodiments, the synthetic method of the above compounds 14, 16, 143 and 147 will be explained herein below. However, the synthetic method explained herein below is an embodiment.

(Synthesis of Compound 14)

As the amine derivative including a fluorine substituted aryl group according to examples, the above compounds 3, 8, 13, 14, 15, 16, 17, 20, 25, 26, 27, 29, 30, 31, 32, 36, 39, 40, 41, 42, 46, 49, 50, 66, 69, 70, 101, 102, 109, 110, 113, 117, 118, 119, 120, 121, 122, 124, 125, 126, 133, 134, 137, 138, 139, 140, 141, 143, 144, 147, 148, 149, 150, 151, 152, 153, 154, 155, 156, 157, 158, 160, 161, 162, 163, 164, 167, 171, 172 and 173 may be exemplified. For example, the above compounds 3, 13, 14, 15, 16, 17, 20, 30, 50, 121, 122, 141, 147, 151, 152, 153, 154, 161, 162, 171, 172, and 173 may be exemplified.

As described above, in other implementations, the amine derivative including a fluorine substituted aryl group according to embodiments may be compounds other than the above-described compounds 1 to 180. In addition, the amine derivative including a fluorine substituted aryl group according to embodiments may include a carbazole portion exhibiting hole transport properties and a fluorine substituted aryl group exhibiting high electron durability, and may be used as the hole transport material of an organic EL device. For example, an amine derivative may be used as a host material of an emission layer of an organic EL device by introducing the following substituents exhibiting electron transporting properties in R2 of Formula 1.

[Reaction Scheme 1]

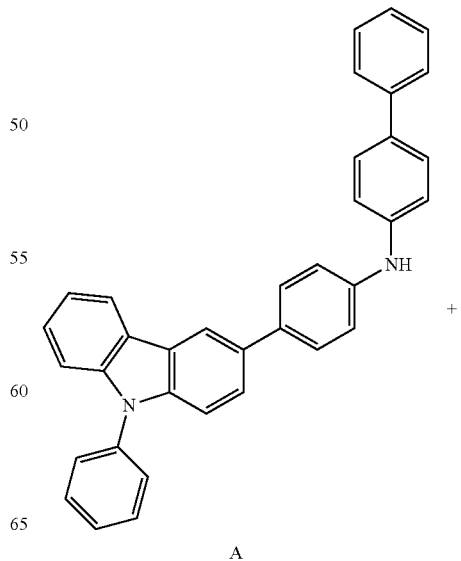

A

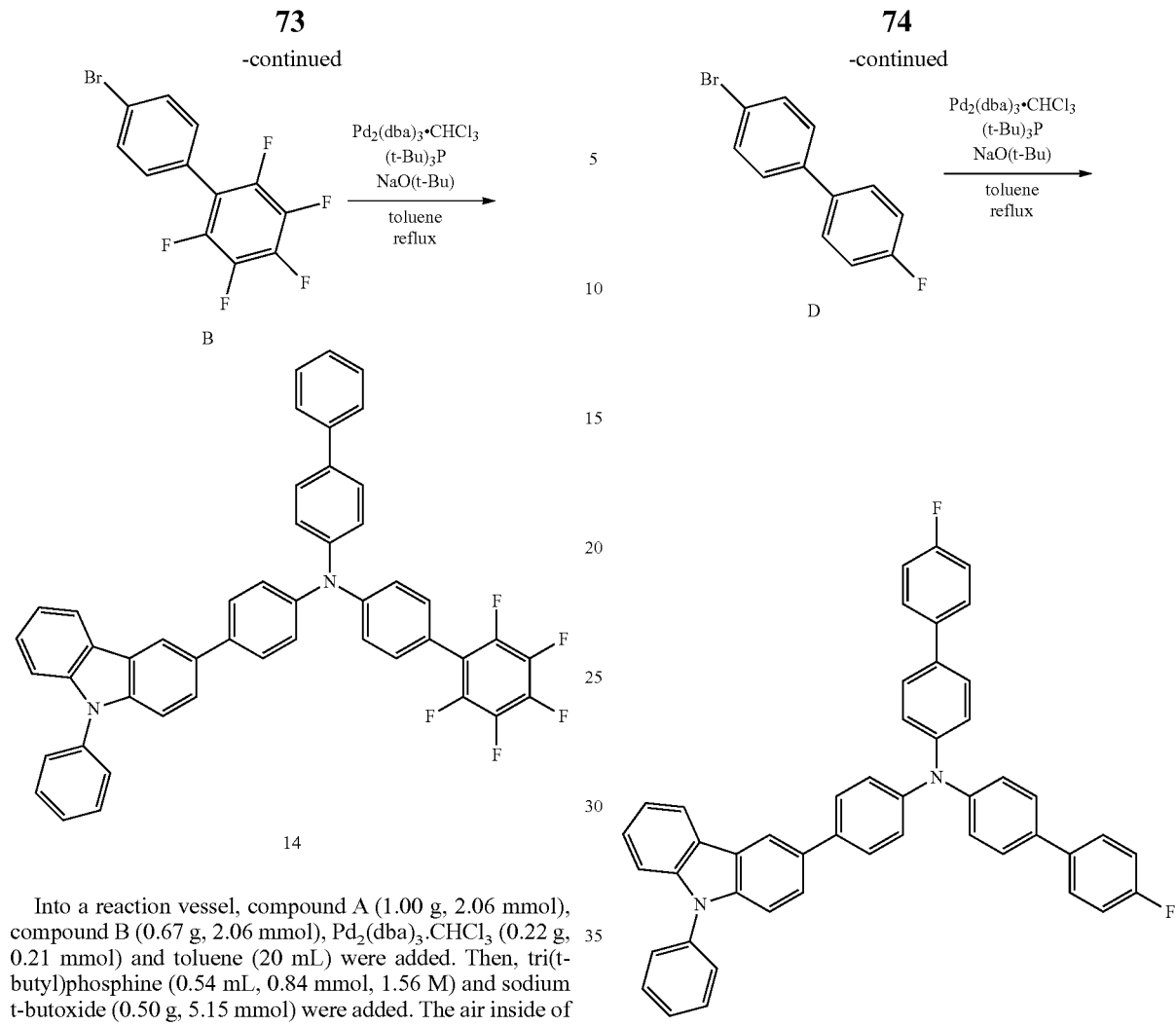

Into a reaction vessel, compound A (1.00 g, 2.06 mmol), compound B (0.67 g, 2.06 mmol), Pd$_2$(dba)$_3$·CHCl$_3$ (0.22 g, 0.21 mmol) and toluene (20 mL) were added. Then, tri(t-butyl)phosphine (0.54 mL, 0.84 mmol, 1.56 M) and sodium t-butoxide (0.50 g, 5.15 mmol) were added. The air inside of the reaction vessel was replaced with nitrogen gas, and the reactant was refluxed for 8 hours while stirring. After cooling, water was added into the reactant, and an organic layer was extracted. The organic layer thus obtained was dried using anhydrous magnesium sulfate, and filtered, and the filtrate was concentrated by using a rotary evaporator. The crude product thus obtained was purified by silica gel column chromatography (developing solvent: dichloromethane/hexane), and the solid thus obtained was recrystallized using toluene/hexane to obtain 0.75 g of the target product of compound 14 as a solid of a white powder. The yield was 50% (FAB-MS: C48H29F5N2, measured value 728).

(Synthesis of Compound 16)

[Reaction Scheme 2]

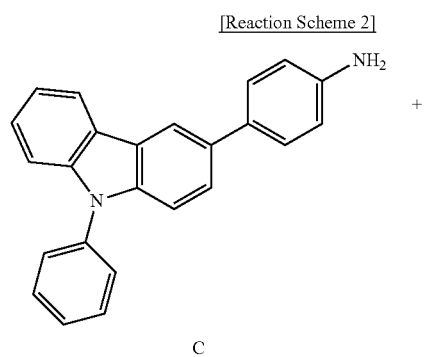

Into a reaction vessel, compound C (1.00 g, 2.06 mmol), compound D (1.03 g, 4.12 mmol), Pd$_2$(dba)$_3$-CHCl$_3$ (0.44 g, 0.42 mmol) and toluene (30 mL) were added. Then, tri(t-butyl)phosphine (1.08 mL, 1.68 mmol, 1.56 M) and sodium t-butoxide (0.50 g, 5.15 mmol) were added. The air inside of the reaction vessel was replaced with nitrogen gas, and the reactant was refluxed for 8 hours while stirring. After cooling, water was added into the reactant, and an organic layer was extracted. The organic layer thus obtained was dried using anhydrous magnesium sulfate, and filtered, and the filtrate was concentrated by using a rotary evaporator. The crude product thus obtained was purified by silica gel column chromatography (developing solvent: dichloromethane/hexane), and the solid thus obtained was recrystallized using toluene/hexane to obtain 0.83 g of the target product of compound 16 as a solid of a white powder. The yield was 60% (FAB-MS: C48H32F2N2, measured value 674).

75

(Synthesis of Compound 143)

[Reaction Scheme 3]

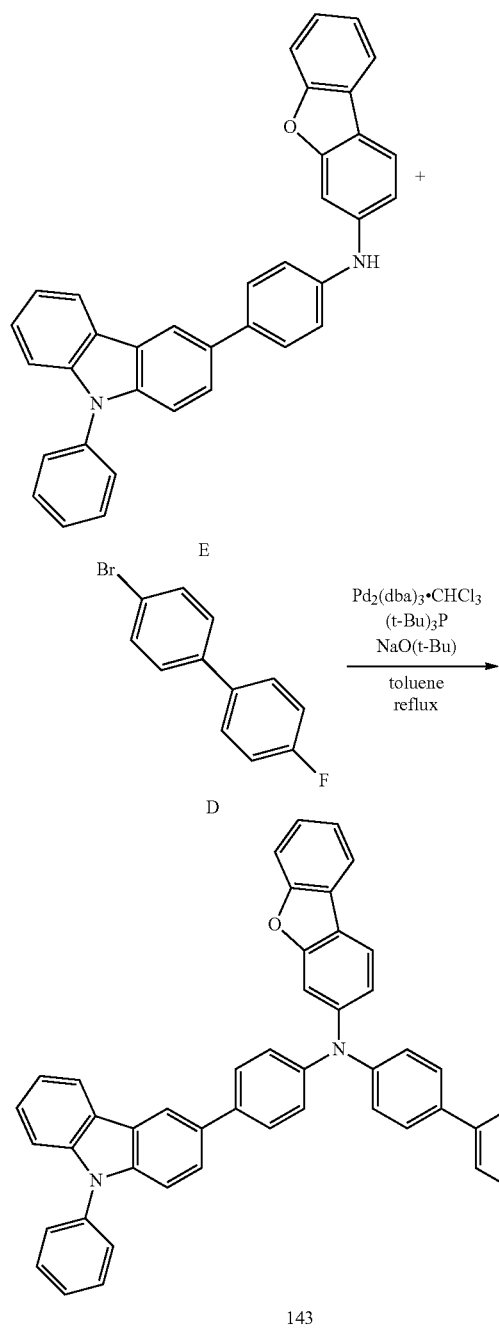

Into a reaction vessel, compound E (0.90 g, 1.80 mmol), compound D (0.45 g, 1.80 mmol), Pd$_2$(dba)$_3$·CHCl$_3$ (0.26 g, 0.18 mmol) and toluene (20 mL) were added. Then, tri(t-butyl)phosphine (0.46 mL, 0.72 mmol, 1.56 M) and sodium t-butoxide (0.43 g, 4.50 mmol) were added. The air inside of the reaction vessel was replaced with nitrogen gas, and the reactant was refluxed for 8 hours while stirring. After cooling, water was added into the reactant, and an organic layer was extracted. The organic layer thus obtained was dried using anhydrous magnesium sulfate, and filtered, and the filtrate was concentrated by using a rotary evaporator.

76

The crude product thus obtained was purified by silica gel column chromatography (developing solvent: dichloromethane/hexane), and the solid thus obtained was recrystallized using toluene/hexane to obtain 0.66 g of the target product of compound 143 as a solid of a white powder. The yield was 55% (FAB-MS: C48H31FN20, measured value 670).

(Synthesis of Compound 147)

[Reaction Scheme 4]

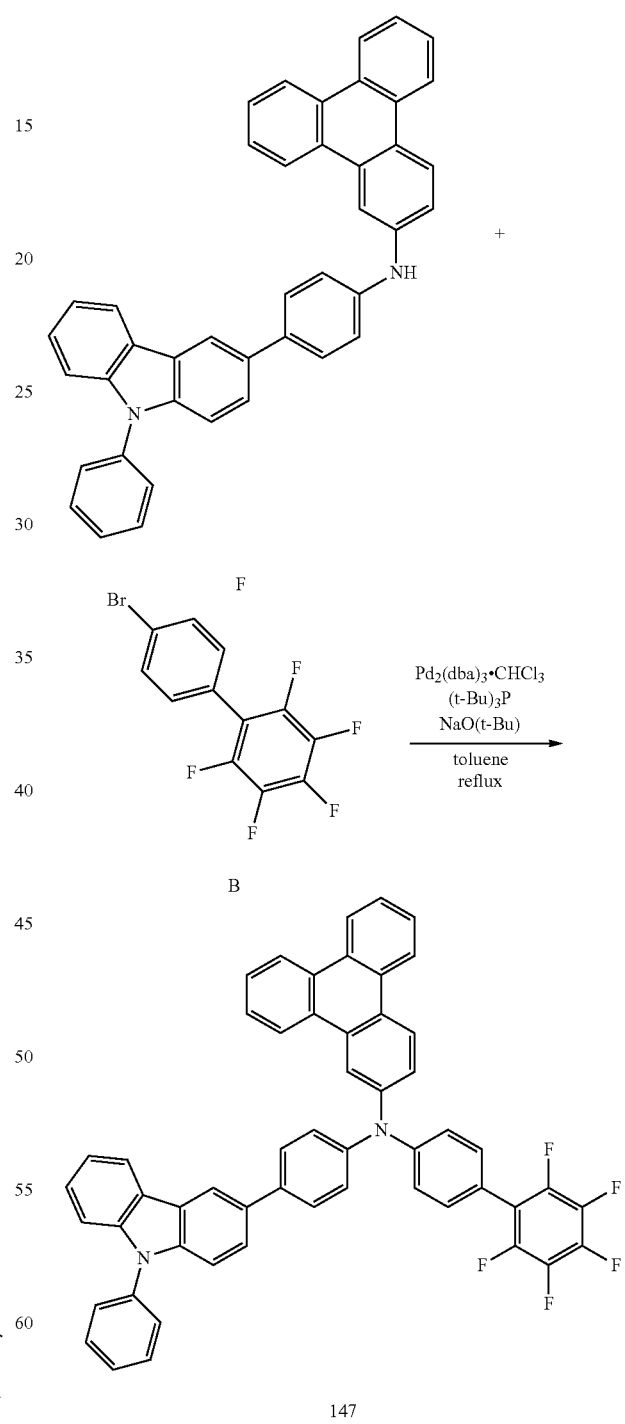

Into a reaction vessel, compound F (1.20 g, 2.14 mmol), compound B (0.70 g, 2.14 mmol), Pd$_2$(dba)$_3$·CHCl$_3$ (0.22 g, 0.21 mmol) and toluene (20 mL) were added. Then, tri(t- butyl)phosphine (0.54 mL, 0.84 mmol, 1.56 M) and sodium t-butoxide (0.51 g, 5.35 mmol) were added. The air inside of the reaction vessel was replaced with nitrogen gas, and the reactant was refluxed for 8 hours while stirring. After cooling, water was added into the reactant, and an organic layer was extracted. The organic layer thus obtained was dried using anhydrous magnesium sulfate, and filtered, and the filtrate was concentrated by using a rotary evaporator. The crude product thus obtained was purified by silica gel column chromatography (developing solvent: dichloromethane/hexane), and the solid thus obtained was recrystallized using toluene/hexane to obtain 0.77 g of the target product of compound 147 as a solid of a white powder. The yield was 45% (FAB-MS: C48H29F5N2, measured value 802).

The following Examples and Comparative Examples are provided in order to highlight characteristics of one or more embodiments, but it is to be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

EXAMPLES

Light-emitting life (T50%) of an organic EL device using the amine derivative including a fluorine substituted aryl group according to embodiments as a hole transport material was measured. As the hole transport materials of the organic EL device, the above compounds 14, 16, 143, and 147 were used. In addition, comparative compound 1 and comparative compound 2 illustrated in the following chemical formulae as comparative compounds were used as the hole transport materials of the organic EL device. Here, an organic EL device using compound 14 as the hole transport material corresponds to Example 1, an organic EL device using compound 16 as the hole transport material corresponds to Example 2, an organic EL device using compound 143 as the hole transport material corresponds to Example 3, an organic EL device using compound 147 as the hole transport material corresponds to Example 4, an organic EL device using comparative compound 1 as the hole transport material corresponds to Comparative Example 1, and an organic EL device using comparative compound 2 as the hole transport material corresponds to Comparative Example 2.

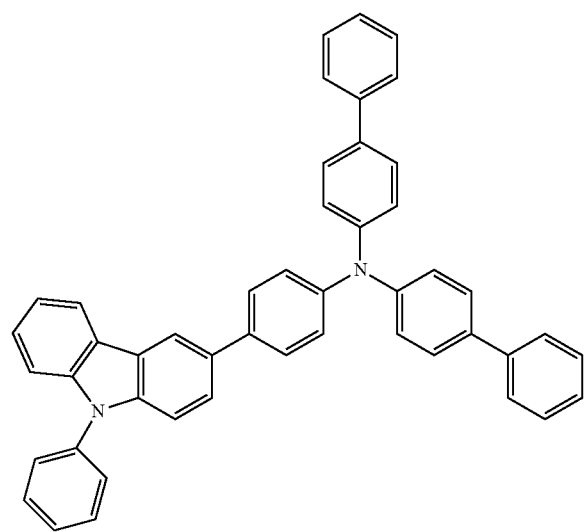

Comparative compound 1

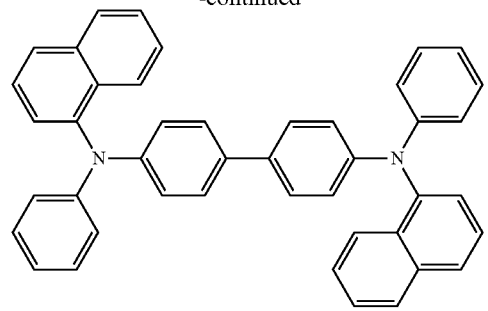

Comparative compound 2

The configuration of an organic EL device used for the measurement is illustrated in FIG. 1. In FIG. 1, an organic EL device 100 includes a glass substrate 102, a positive electrode 104 disposed on the glass substrate 102 and formed by using indium tin oxide (ITO), a hole injection layer 106 disposed on the positive electrode 104 and including 4,4',4''-Tris-(N-(naphthylen-2-yl)-N-phenylamine)triphenylamine (2-TNATA), a hole transport layer 108 disposed on the hole injection layer 106 and including one among compounds 14, 16, 143 and 147, which are the amine derivatives including a fluorine substituted aryl group according to embodiments, or comparative compound 1, or comparative compound 2, an emission layer 110 disposed on the hole transport layer 108 and formed by using a host material including 9,10-di(2-naphthyl)anthracene (ADN) doped with 3% tetra-t-butyl perylene (TBP), an electron transport layer 112 disposed on the emission layer 110 and including Alq₃, an electron injection layer 114 disposed on the electron transport layer 112 and including LiF and a negative electrode 116 disposed on the electron injection layer 114 and formed by using Al. The thickness of the positive electrode 104 was about 150 nm, the thickness of the hole injection layer 106 was about 60 nm, the thickness of the hole transport layer 108 was about 30 nm, the thickness of the emission layer 110 was about 25 nm, the thickness of the electron transport layer 112 was about 25 nm, the thickness of the electron injection layer 114 was about 1 nm and the thickness of the negative electrode 116 was about 100 nm.

Through the positive electrode 104 and the negative electrode 116, currents flowed from a power source through the organic EL device 100, and the light-emitting life (T50%) of the organic EL device 100 when using compound 14, compound 16, compound 143, compound 147, comparative compound 1 or comparative compound 2 as the material of the hole transport layer 108 was measured. The result is illustrated in the following Table 2. The light-emitting life was measured at 1,000 cd/cm².

TABLE 2

| | Hole transport material | Voltage (V) | Current efficiency (cd/A) (@10 mA/cm²) | Life (hr) (@1,000 cd/cm²) |
|---|---|---|---|---|
| Example 1 | Compound 14 | 6.9 | 6.4 | 1,700 |
| Example 2 | Compound 16 | 7.0 | 6.4 | 1,800 |
| Example 3 | Compound 143 | 6.7 | 6.9 | 1,700 |
| Example 4 | Compound 147 | 6.5 | 7.0 | 1,900 |
| Comparative Example 1 | Comparative compound 1 | 7.5 | 6.2 | 1,500 |
| Comparative Example 2 | Comparative compound 2 | 8.1 | 5.3 | 1,200 |

As may be seen in Table 1, the organic EL device using the amine derivative including a fluorine substituted aryl group according to embodiments as the hole transport material exhibited longer life than the organic EL device using comparative compound 1 or comparative compound 2 as the hole transport material.

In the above-described examples, the amine derivative including a fluorine substituted aryl group according to embodiments was used as the organic EL material in the organic EL device of a passive type. In other implementations, the amine derivative including a fluorine substituted aryl group may also be used as the organic EL material of the organic EL device of an active type, and an organic EL device of the active type having increased life may be realized.

As described above, an organic EL device having long life may be realized by using the amine derivative including a fluorine substituted aryl group according to embodiments as the hole transport material. In addition, regarding the amine derivative including a fluorine substituted aryl group according to embodiments, various modifications may be possible. Also, the amine derivative including a fluorine substituted aryl group according to embodiments may be used as an organic electronics material or an organic electronics device.

By way of summation and review, in the application of the organic EL device to a display apparatus, high efficiency and long life of the organic EL device are desirable, and for realizing the high efficiency and long life, the normalization, stabilization, durability, etc. of each layer constituting an organic EL device have been examined.

The organic EL device using the amine derivative including a fluorine substituted aryl group according to embodiments as an organic EL material may be used in an organic EL display apparatus or a lighting apparatus.

According to the organic EL material, an organic EL device having long life may be realized.

In Formulas 1 to 3, each of R1 and R2 may independently represent a hydrogen atom, or a substituted or unsubstituted aryl group. According to the organic EL material, an organic EL device having long life may be realized.

In Formulas 1 to 3, each of Ar1 and Ar2 may independently represent a substituted or unsubstituted biphenyl group, L may be a substituted or unsubstituted phenylene group, R1 may be a hydrogen atom, and R2 may be a substituted or unsubstituted aryl group. According to the organic EL material, an organic EL device having long life may be realized.

The organic EL material may be used as the hole transport material of an organic EL device. According to the organic EL material, an organic EL device having long life may be realized.

An organic EL device according to an embodiment may include an amine derivative including a fluorine substituted aryl group according to embodiments.

The organic electroluminescence device may include at least an emission layer and a hole transport layer disposed between a negative electrode and a positive electrode. The hole transport layer may include the amine derivative including a fluorine substituted aryl group according to embodiment. Accordingly, an organic EL material realizing an organic EL device having long life may be provided.

The above-disclosed subject matter is to be considered illustrative and not restrictive, and the appended claims are intended to cover all such modifications, enhancements, and other embodiments, which fall within the true spirit and scope of the inventive concept. Thus, to the maximum extent allowed by law, the scope of the inventive concept is to be determined by the broadest permissible interpretation of the following claims and their equivalents, and shall not be restricted or limited by the foregoing detailed description.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope thereof as set forth in the following claims.

What is claimed is:

1. An amine derivative selected from the following compounds 1 to 180:

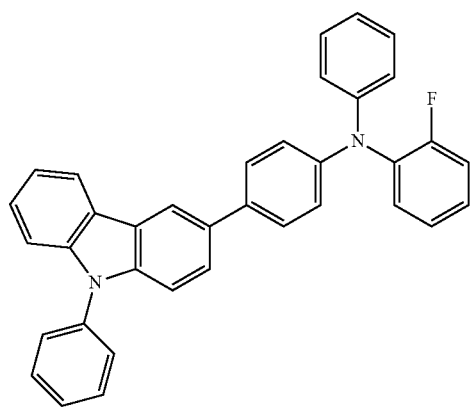

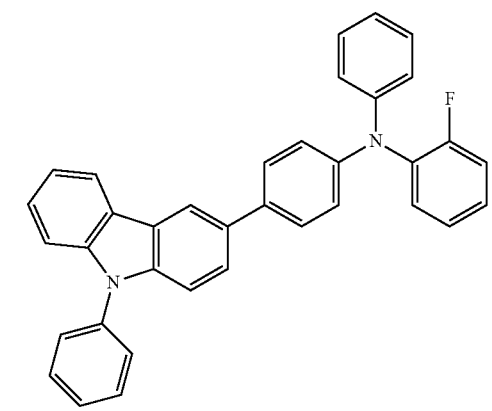

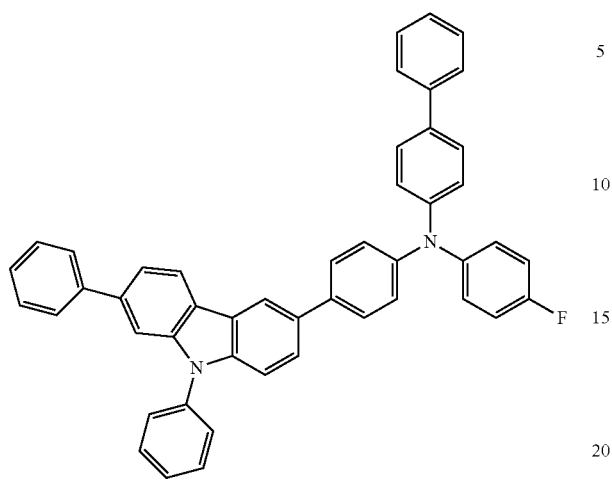
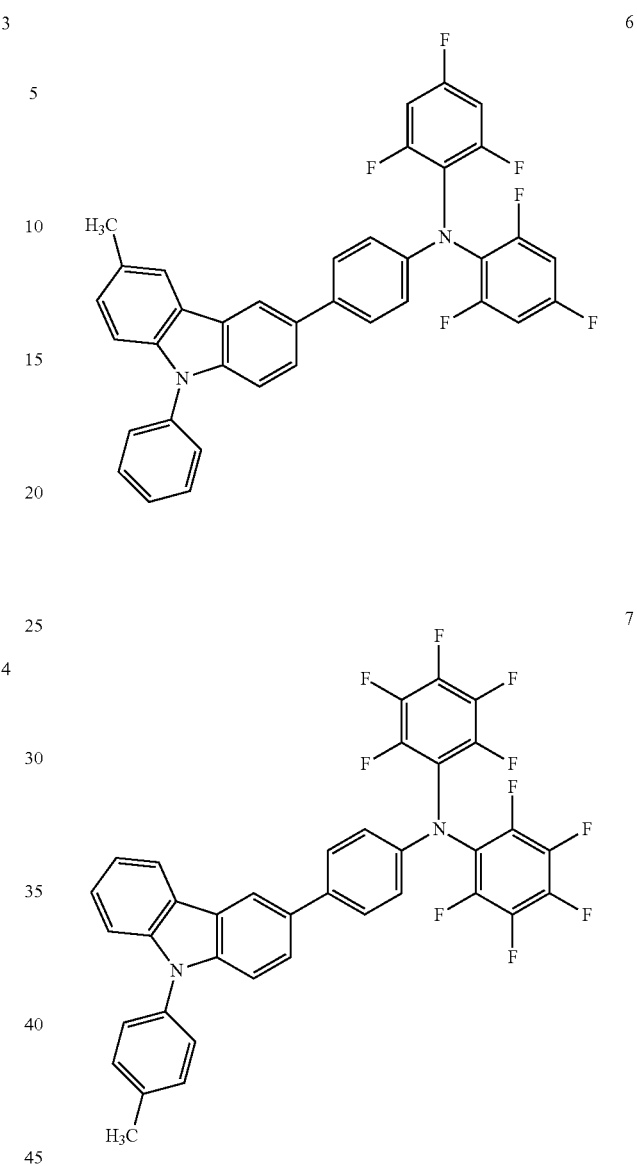
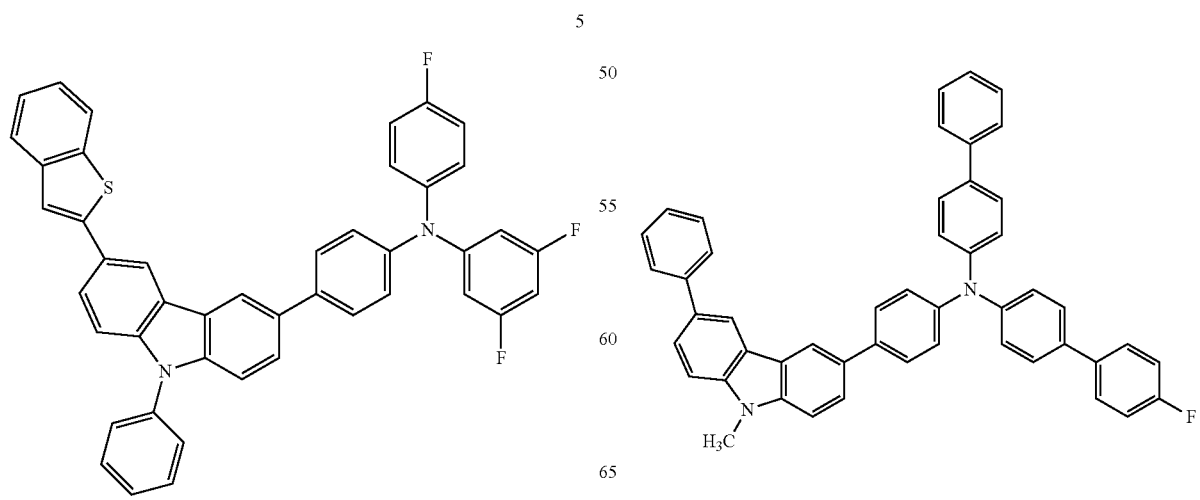

9
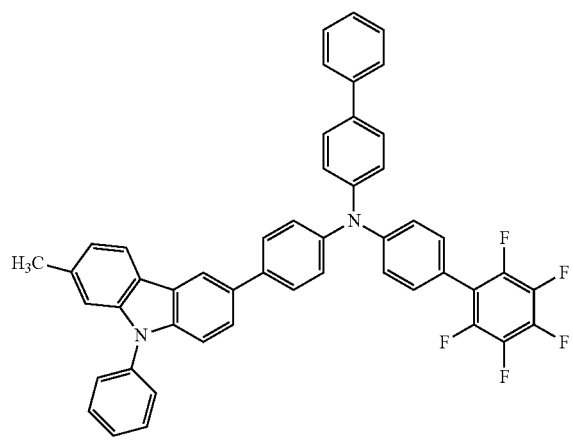
12
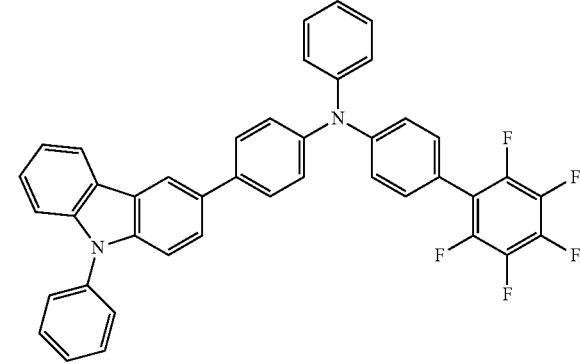
10
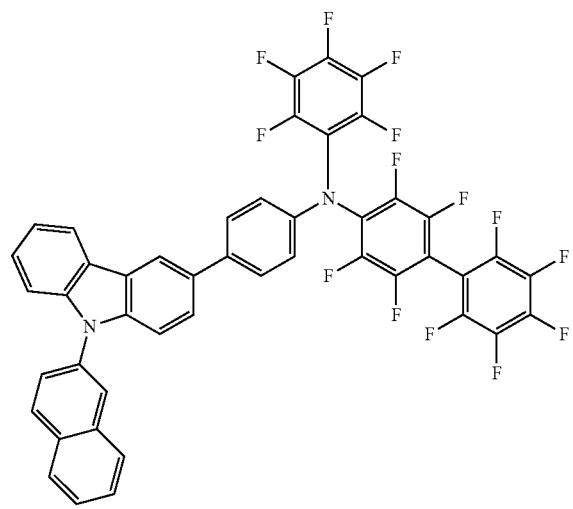
13
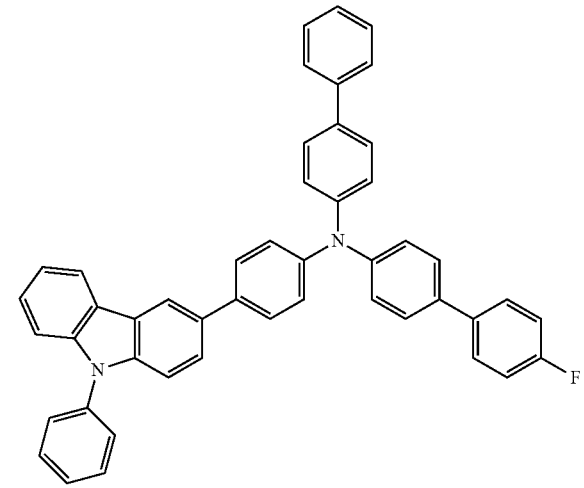
11
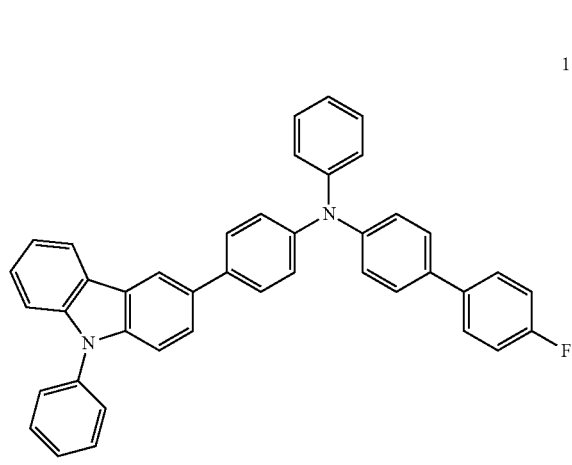
14
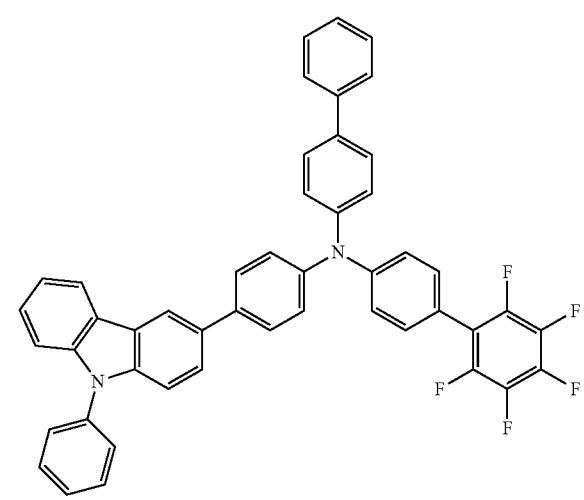

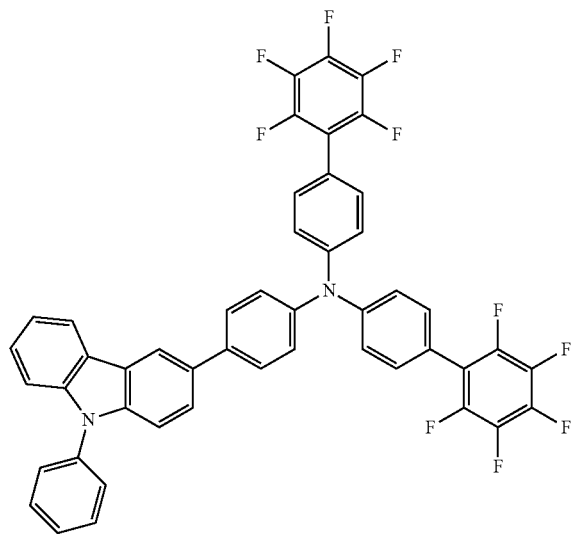
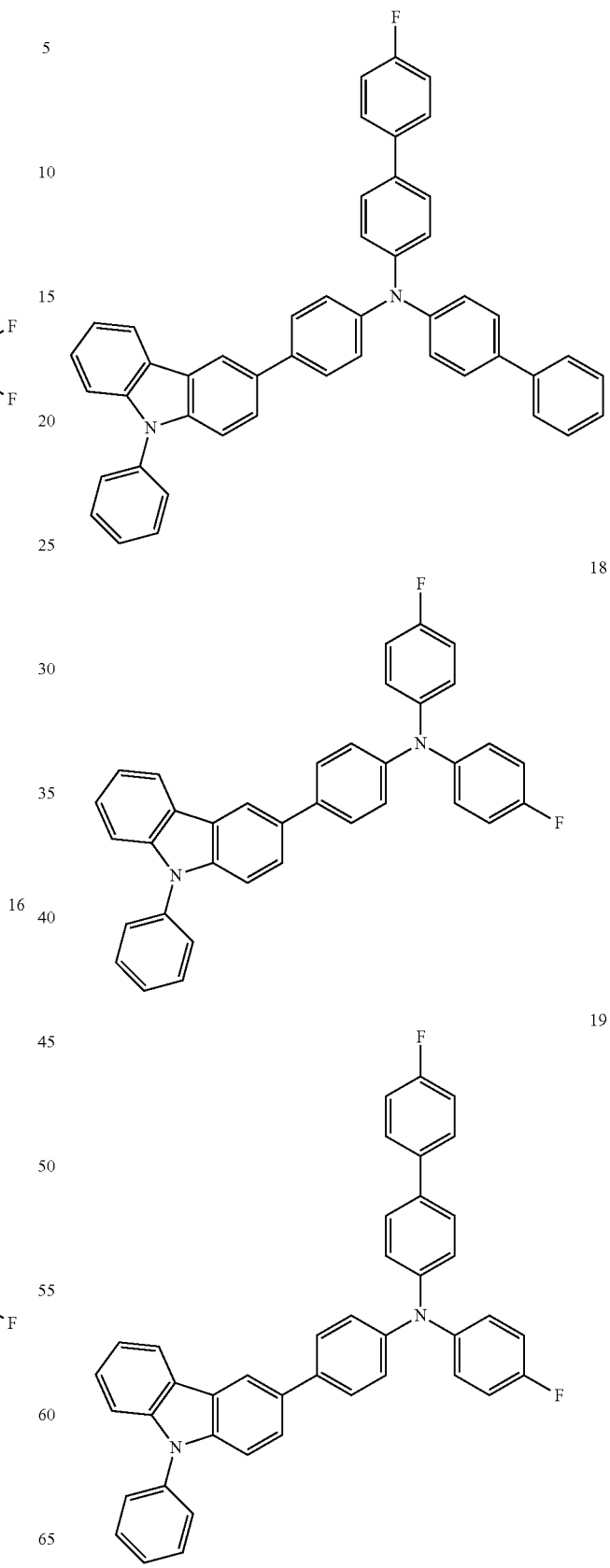

87
-continued
20
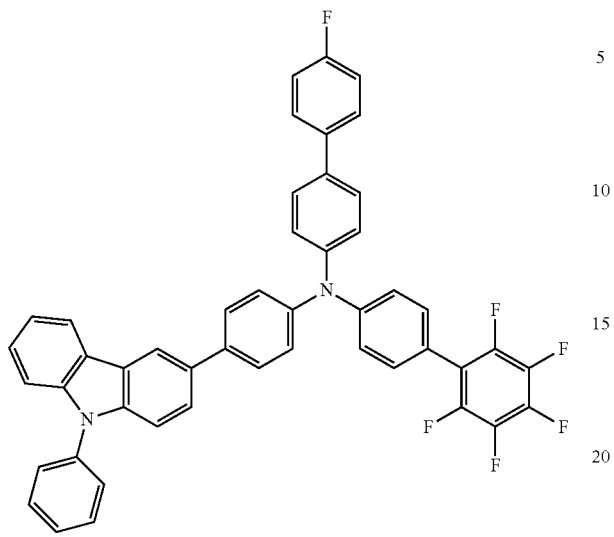
21
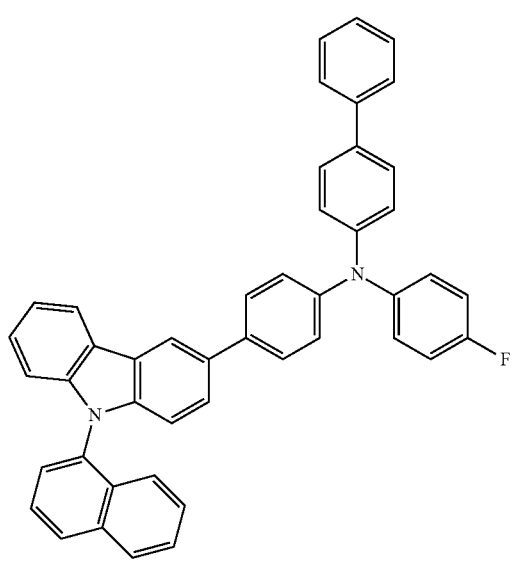
22
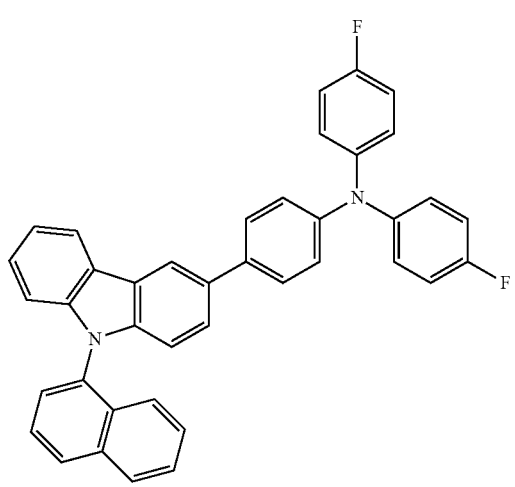
88
-continued
24
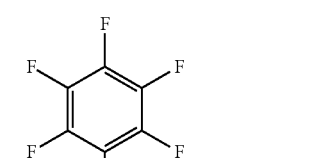
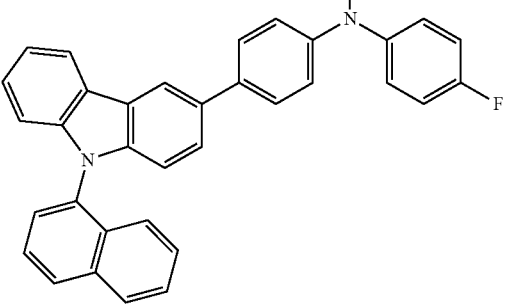
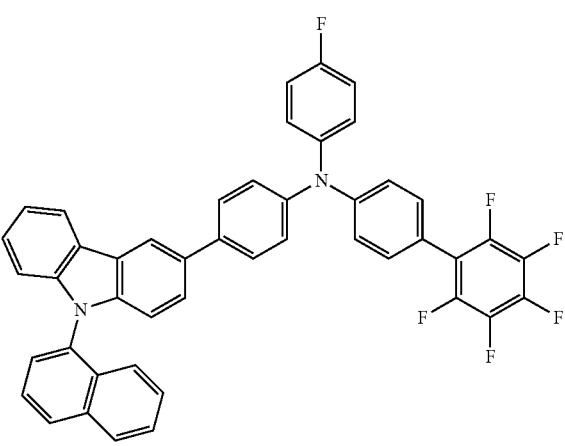

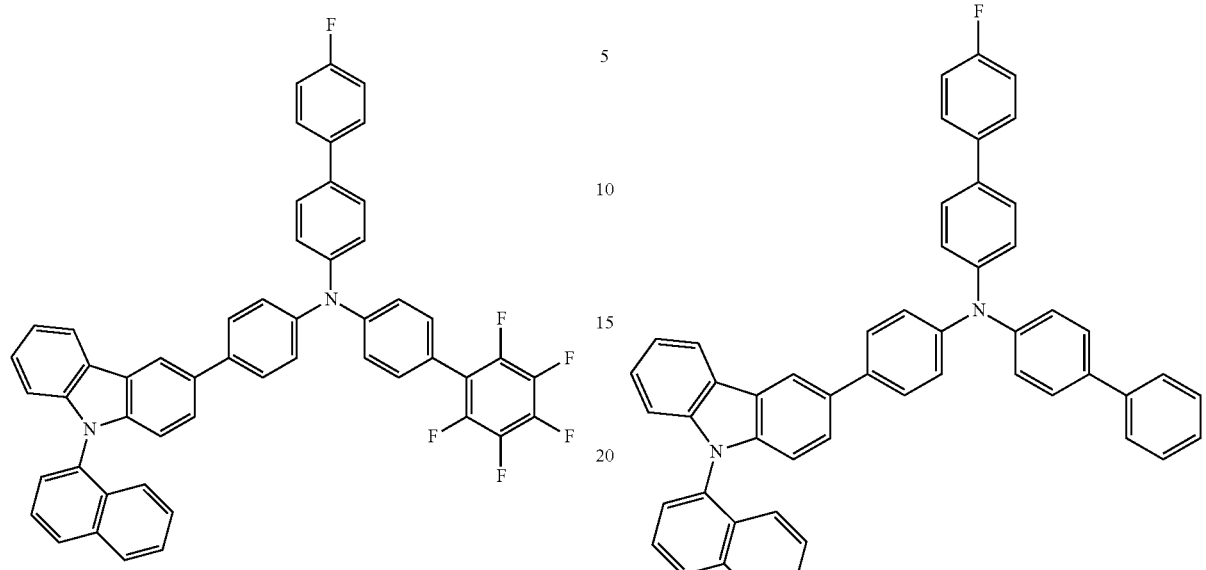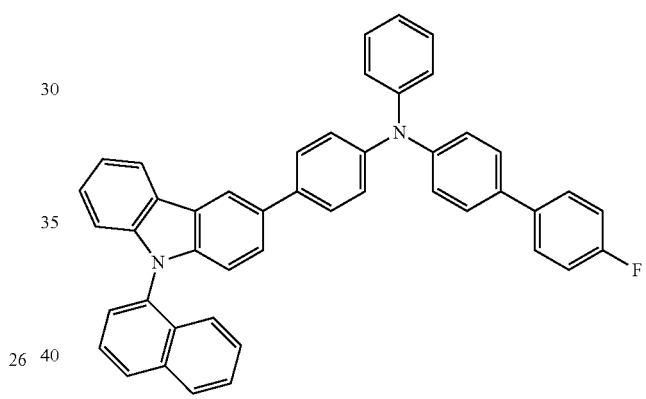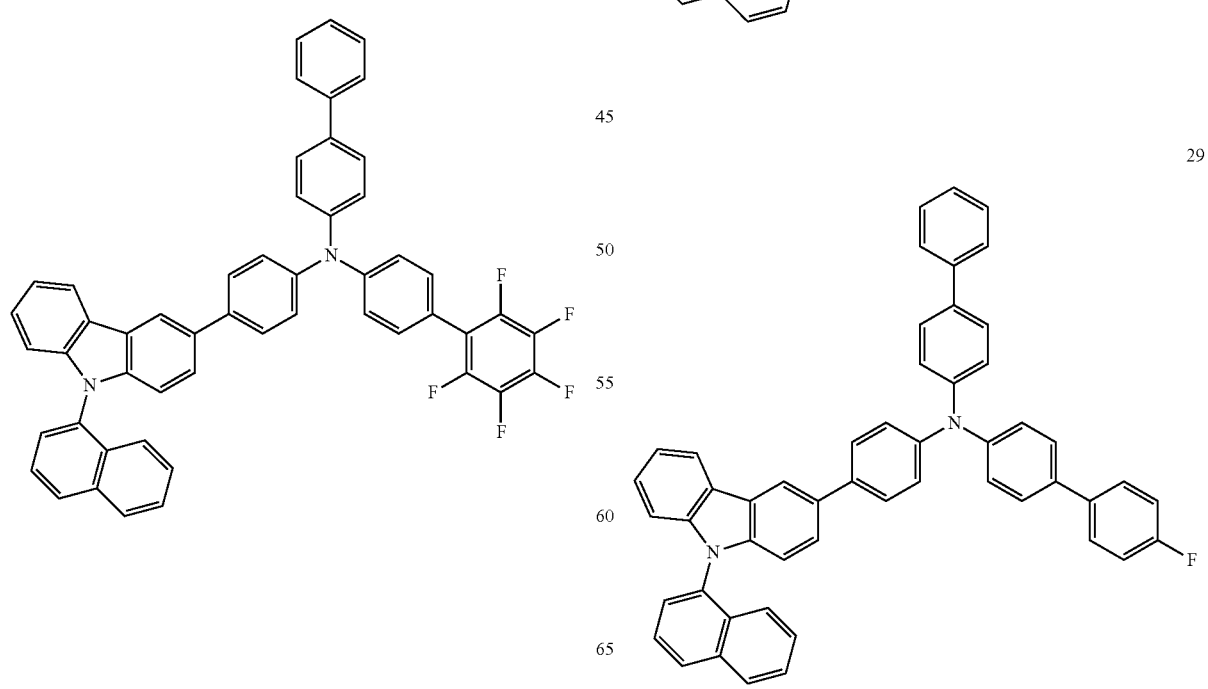

30
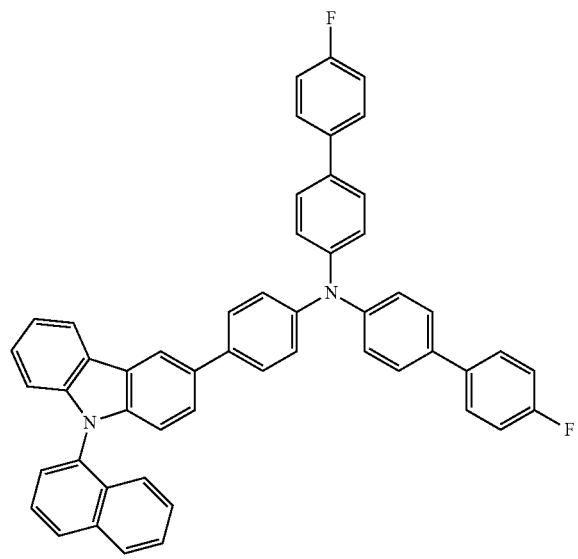
31
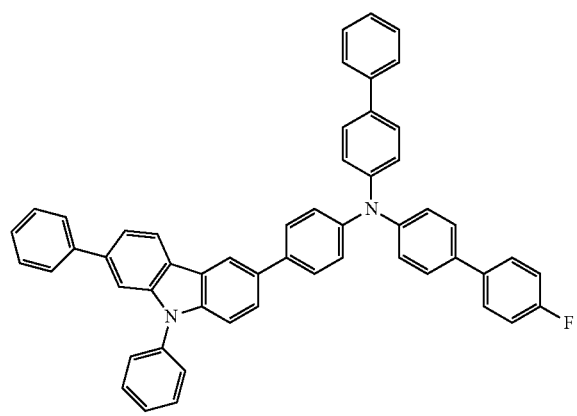
32
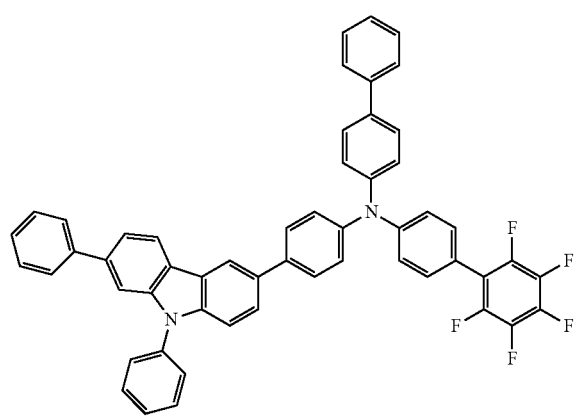
33
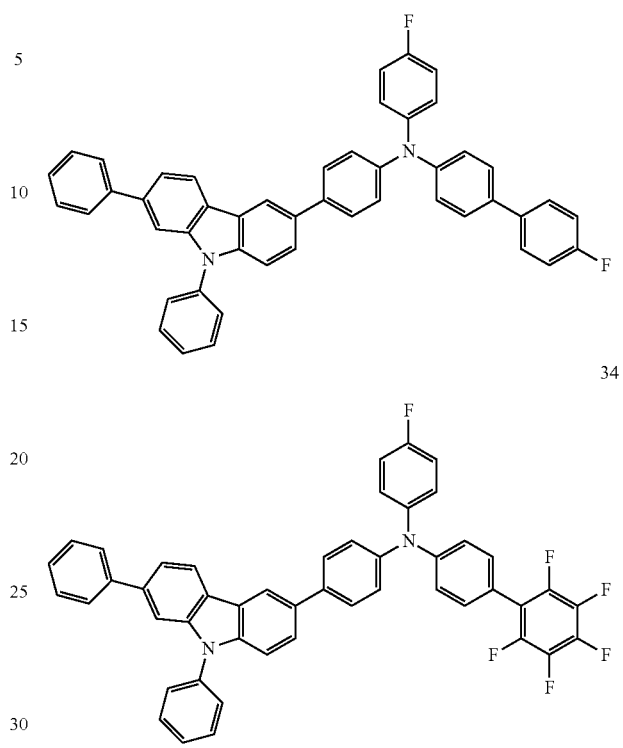
34
35
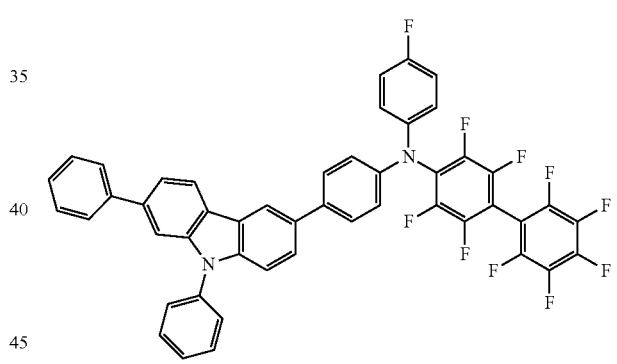
36
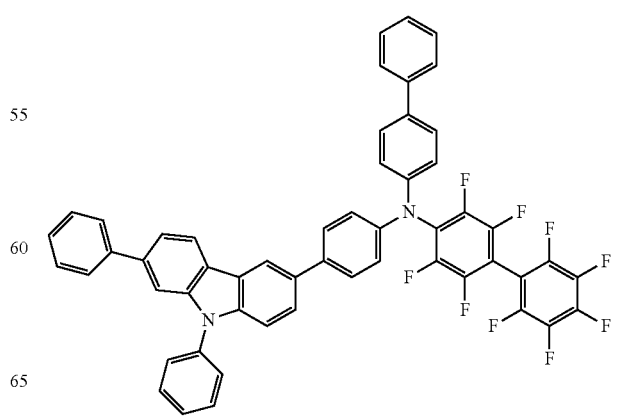

37
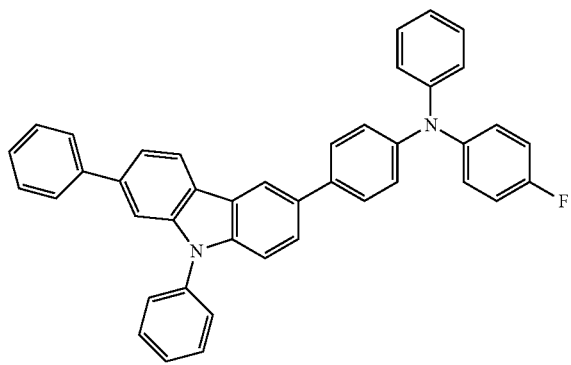
38
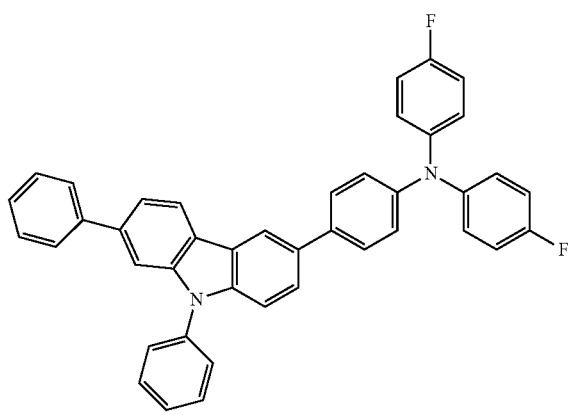
39
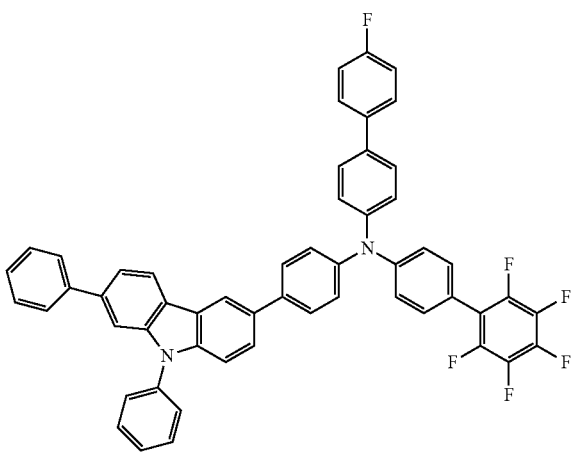
40
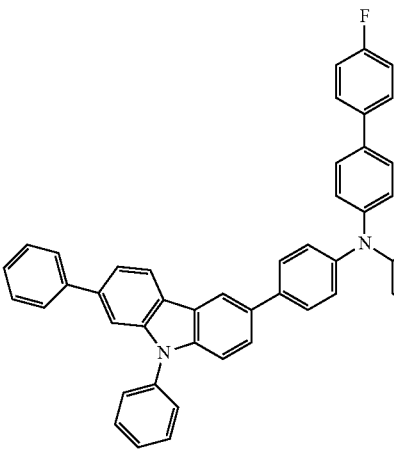
41
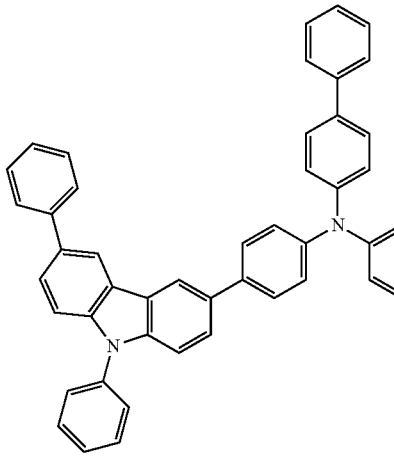
42
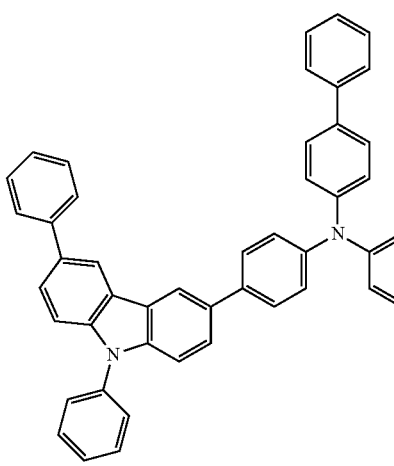

43
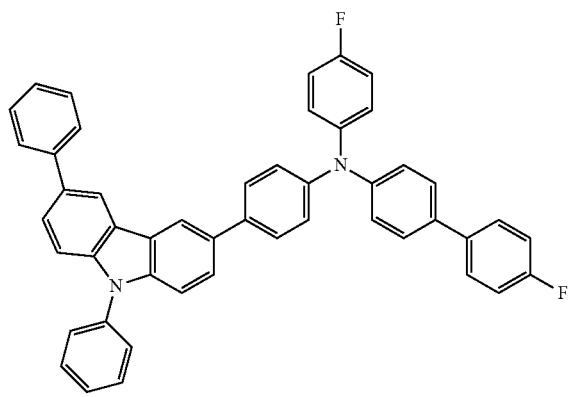
44
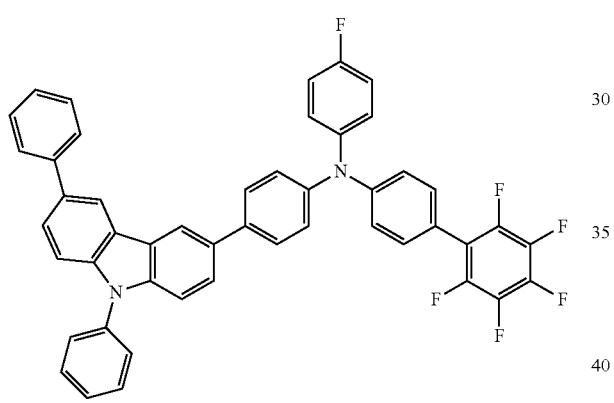
45
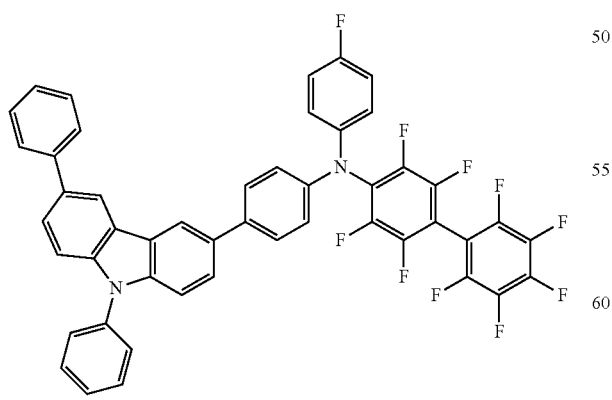
46
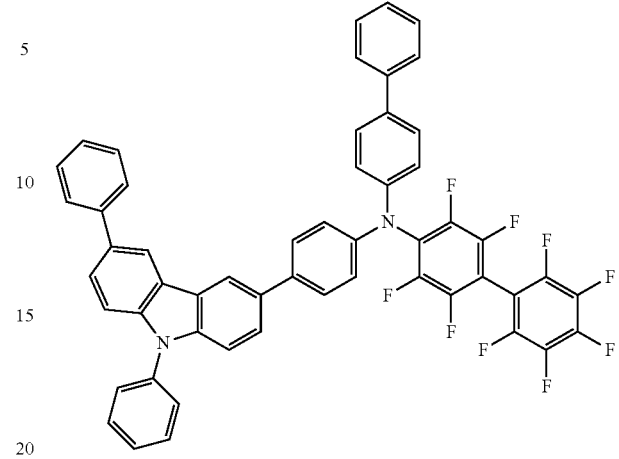
47
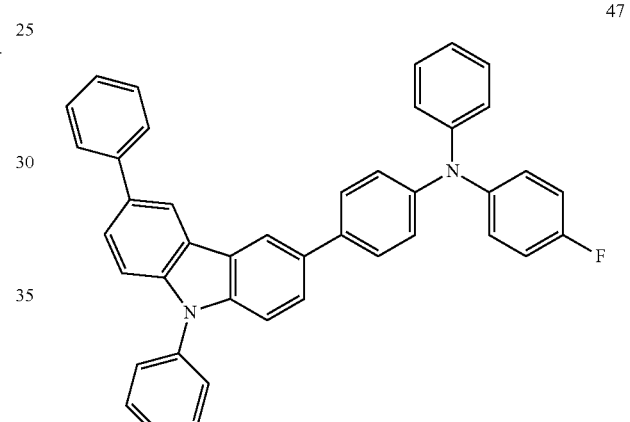
48
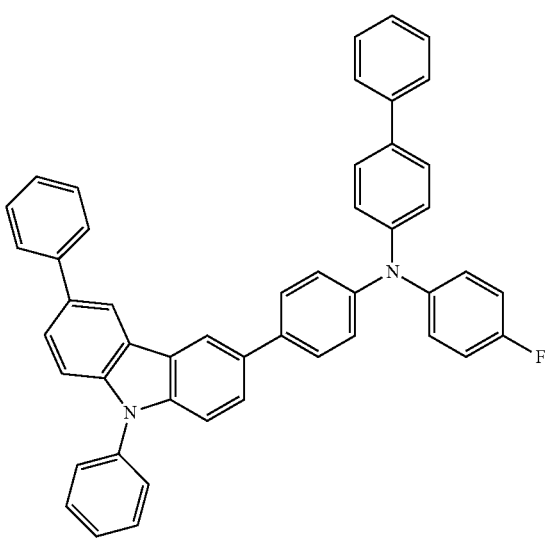

49
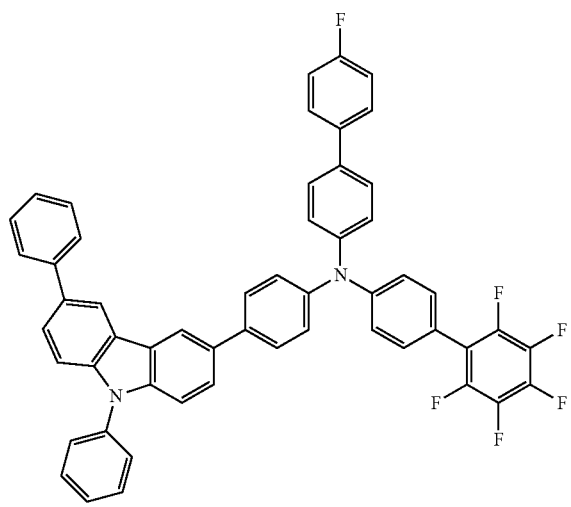
50
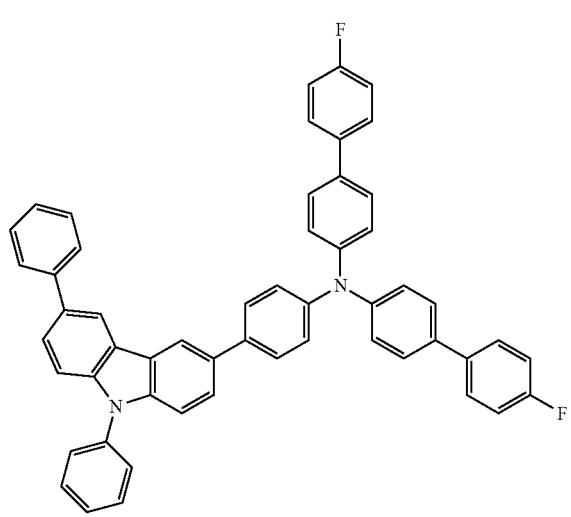
51
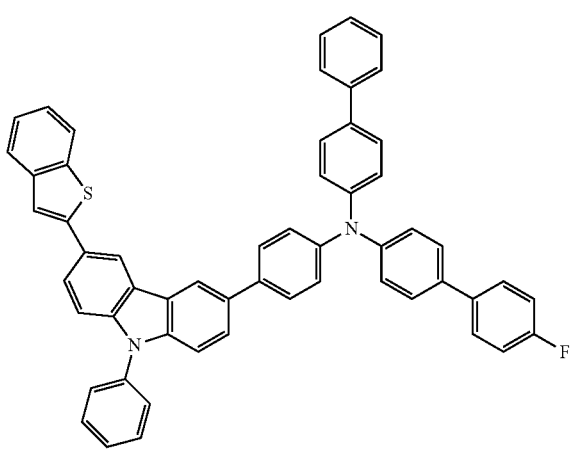
52
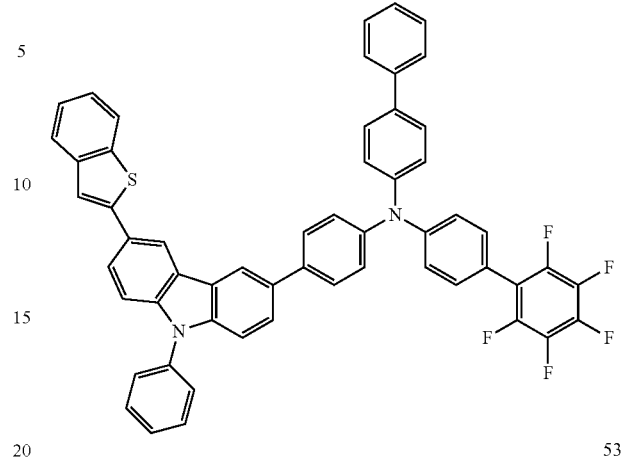
53
54
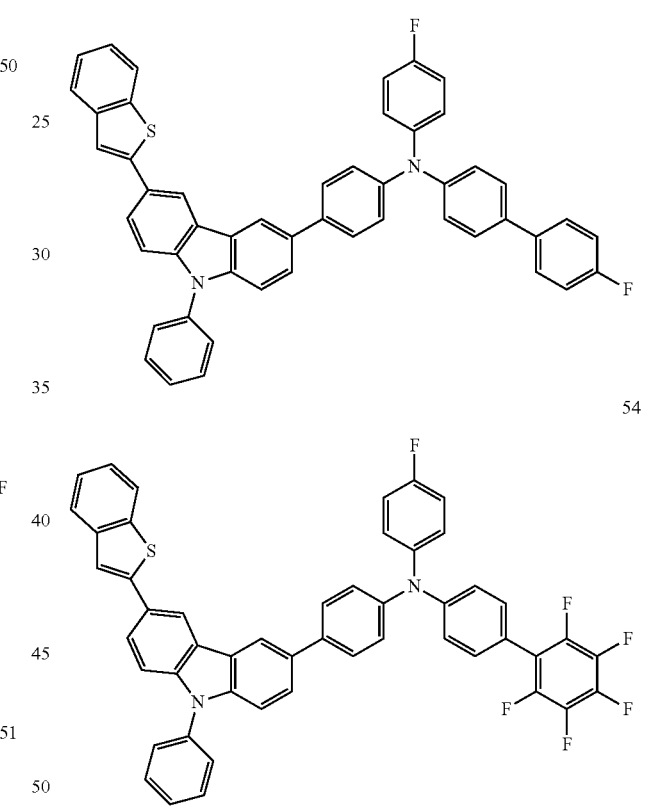
55
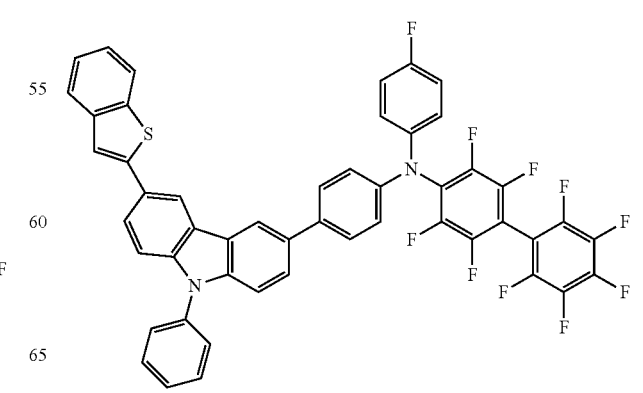

56
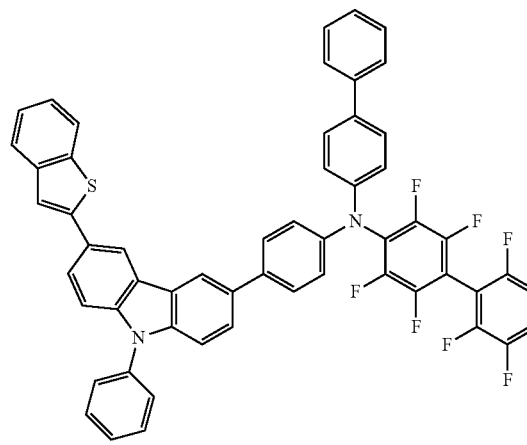
57
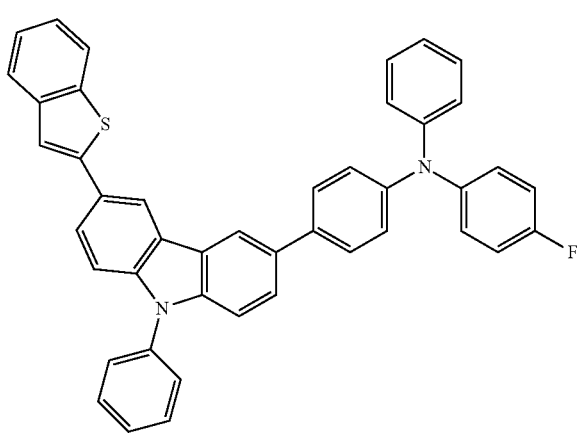
58
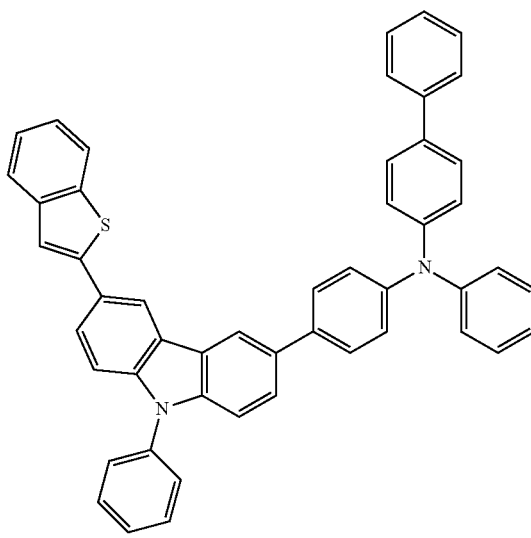
59
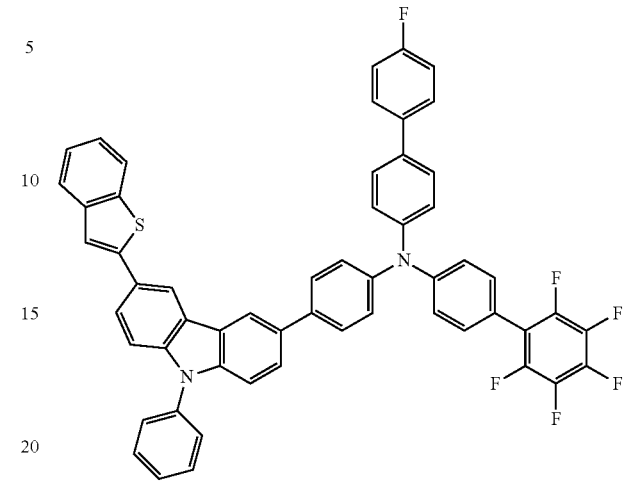
60
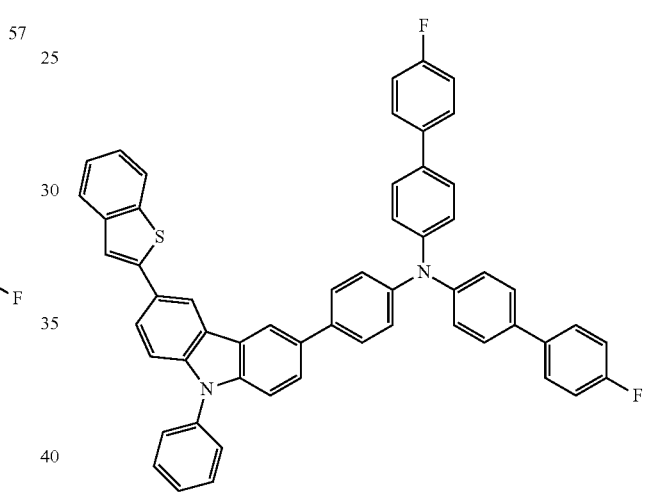
61
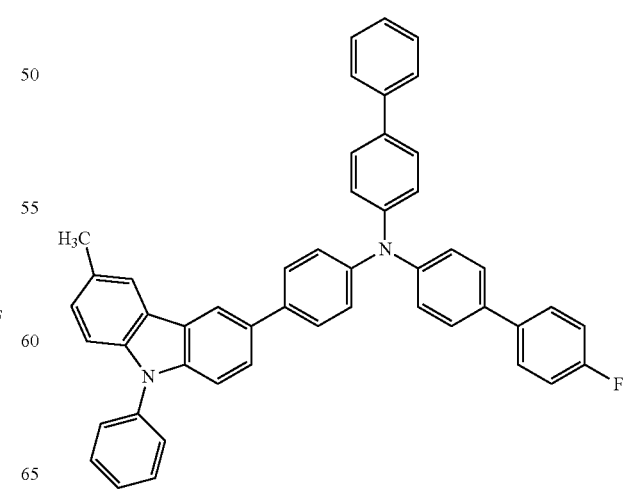

62
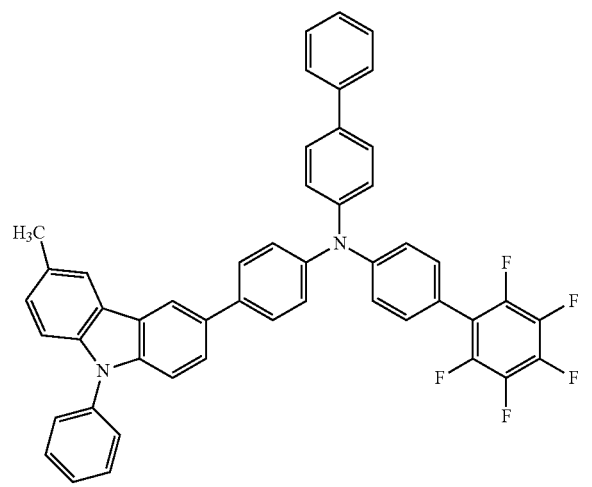
65
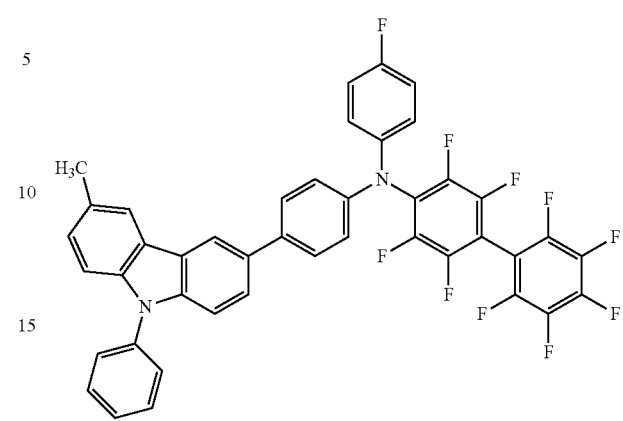
63
66
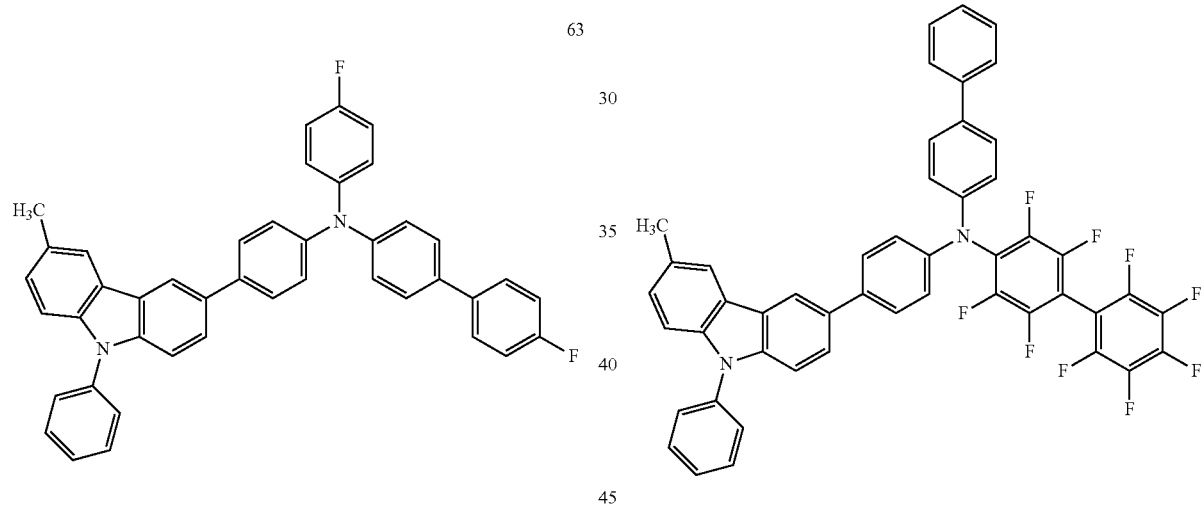
64
67
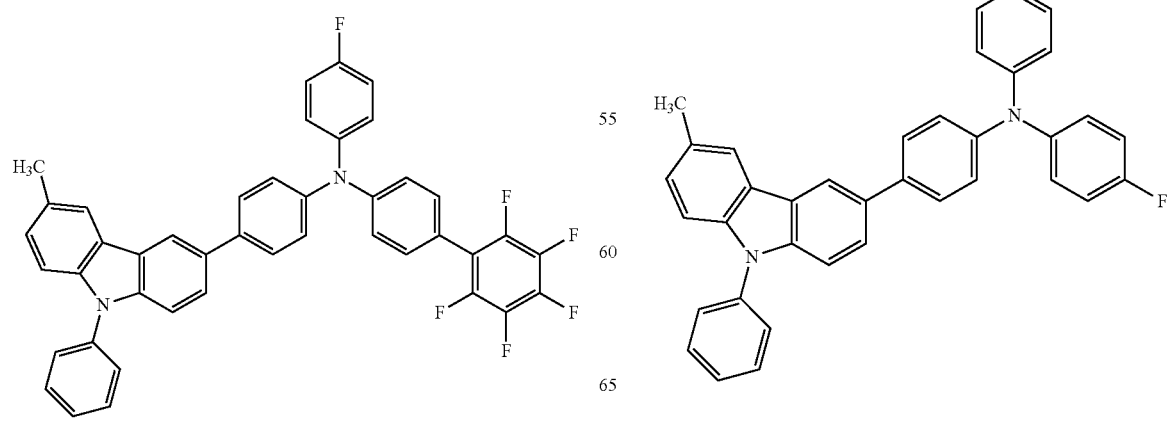

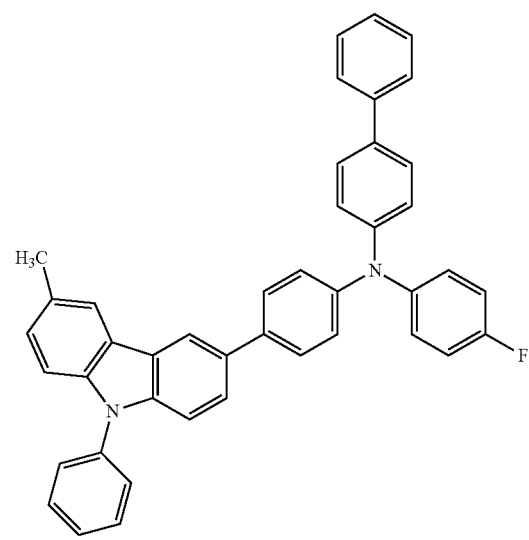
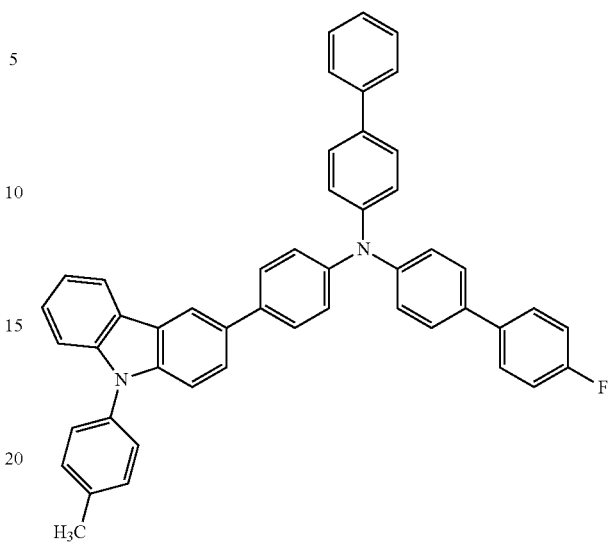
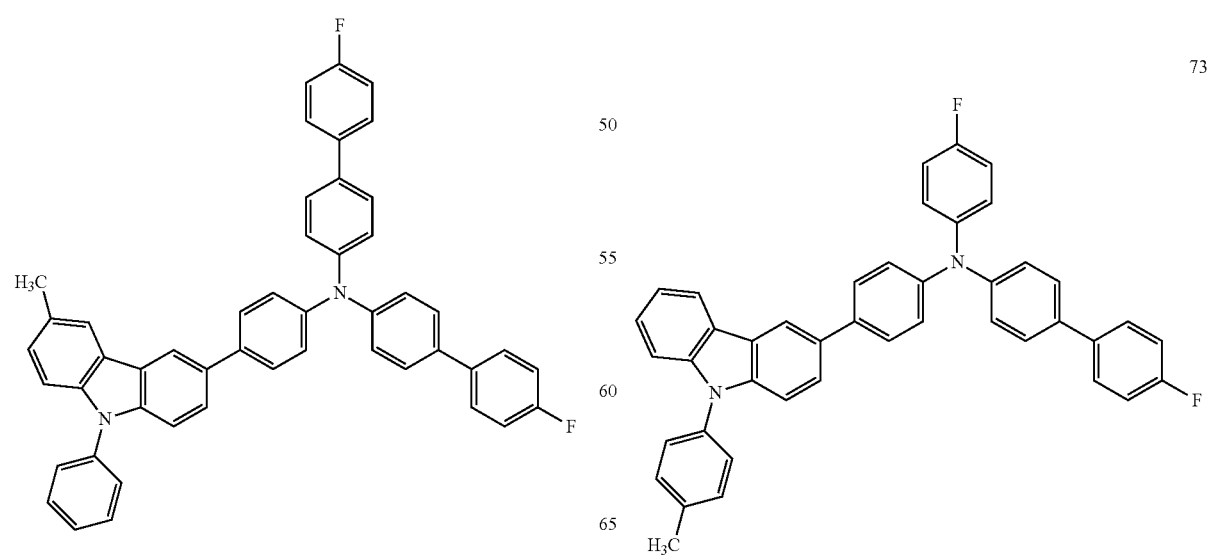

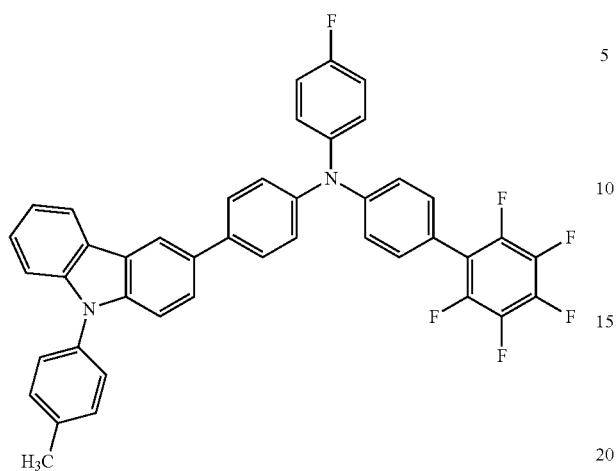
74
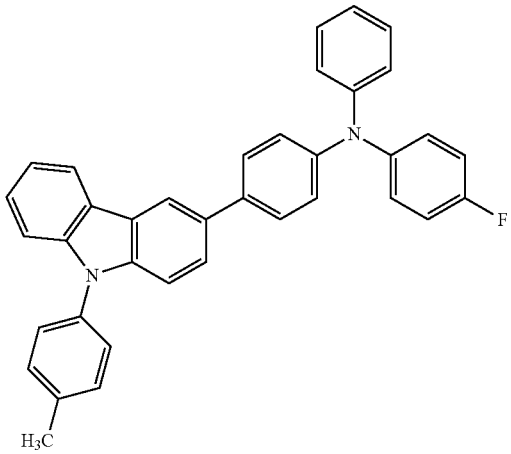
77
75
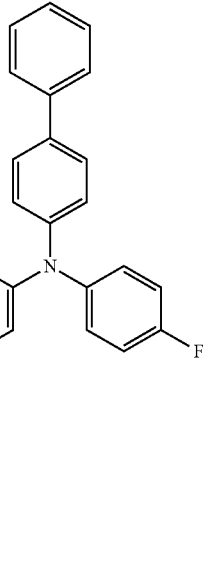
78
76
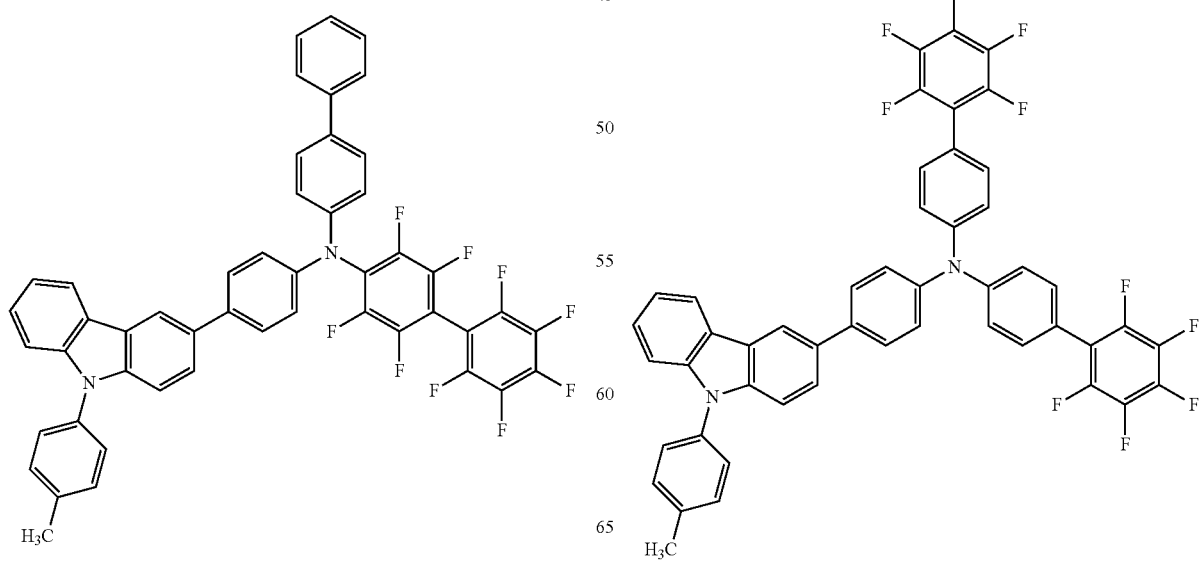
79

107
-continued
80
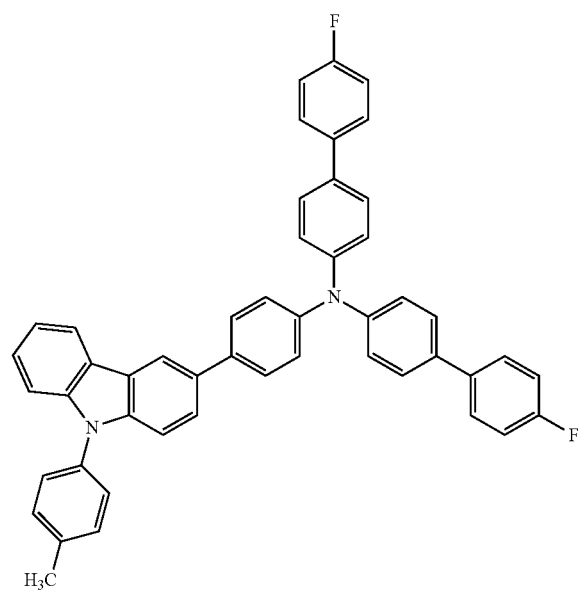
81
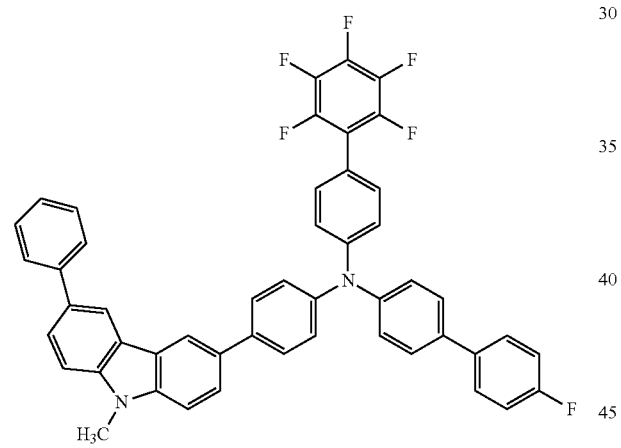
82
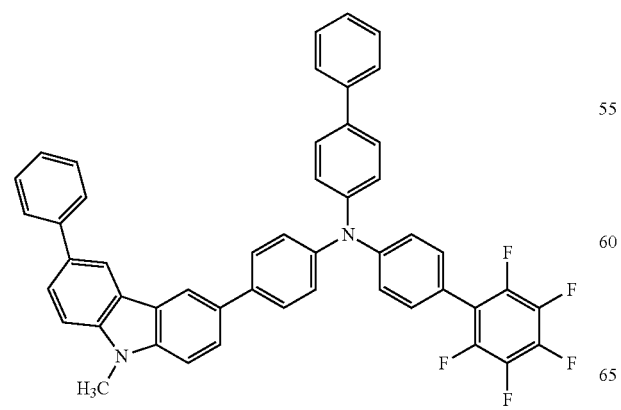
108
-continued
83
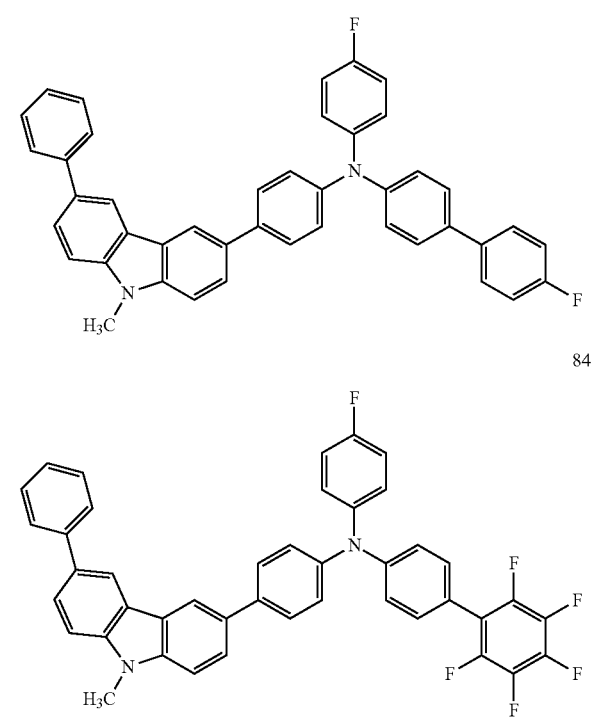
84
85
86
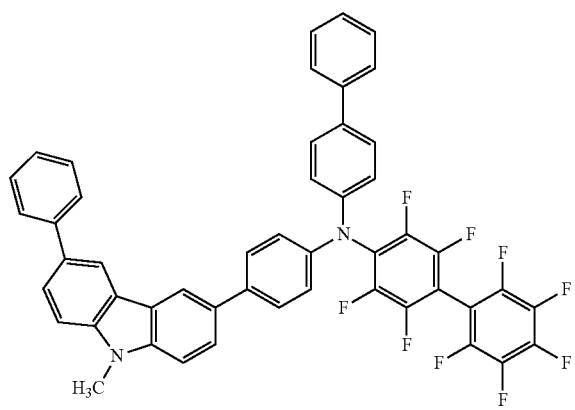

-continued
87
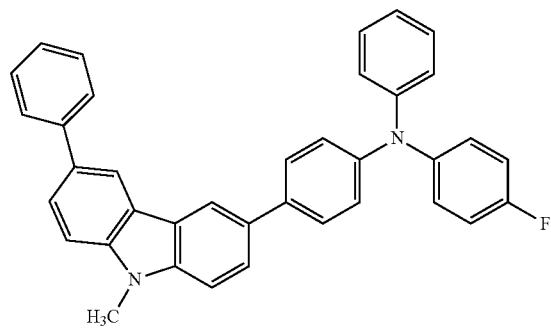
88
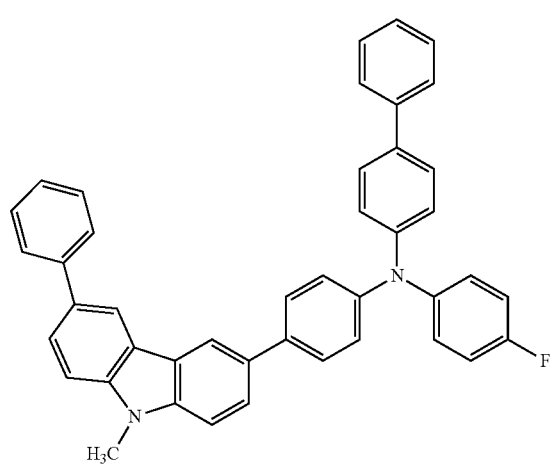
89
-continued
90
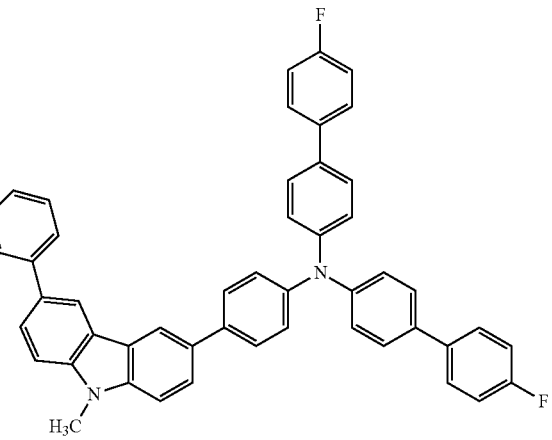
91
92
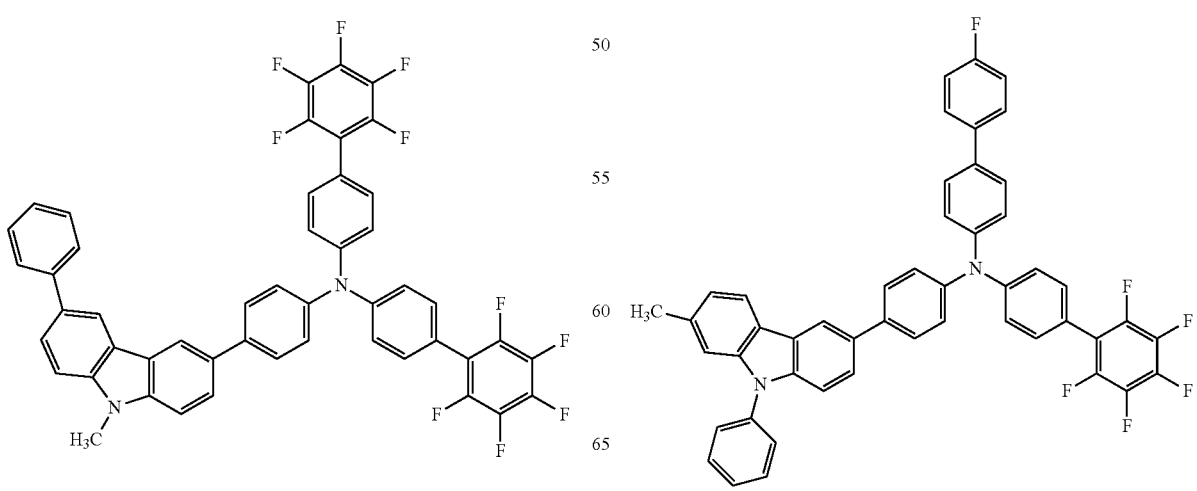

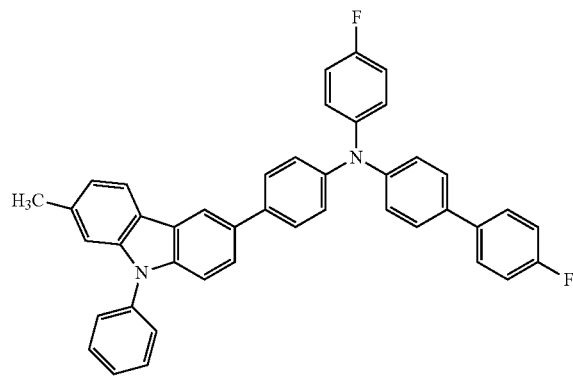
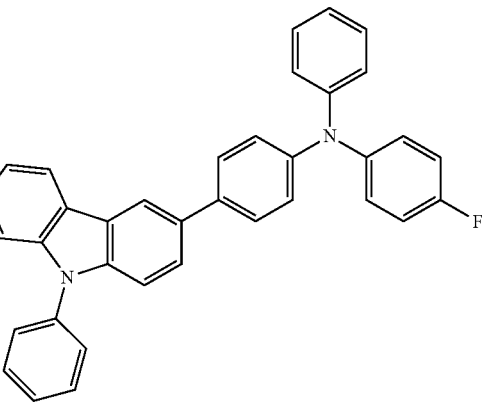
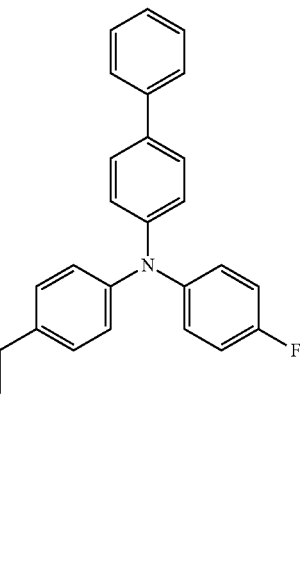

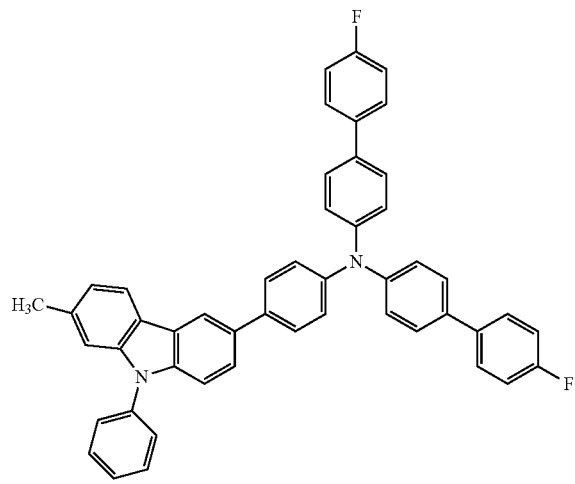
100
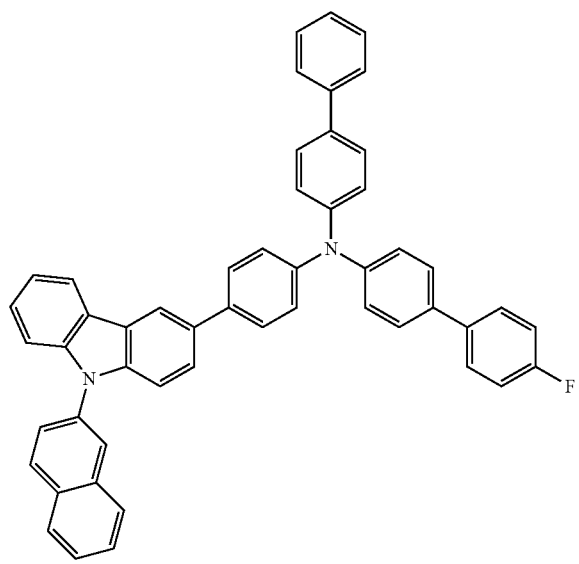
101
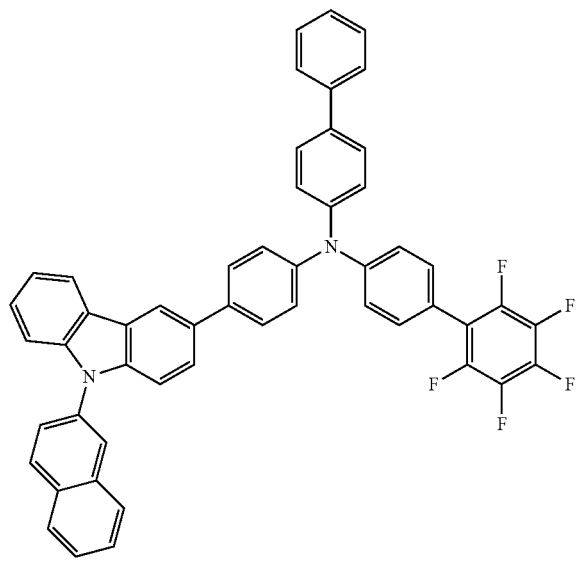
102
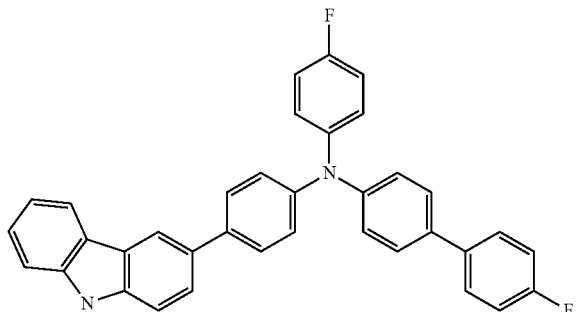
103
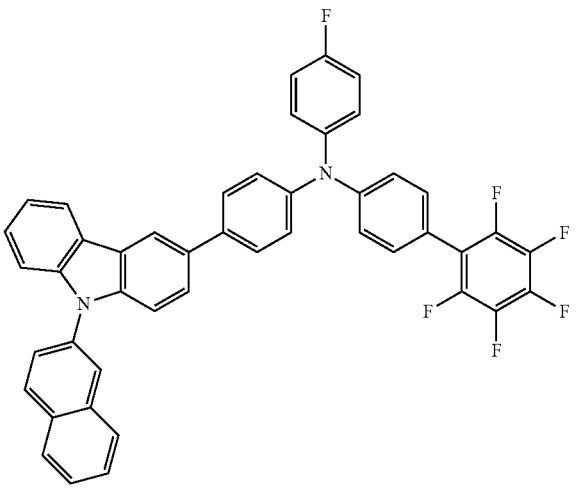
104
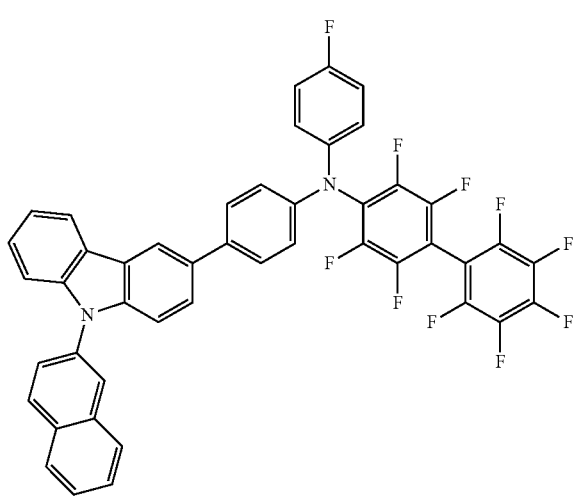
105

-continued
106
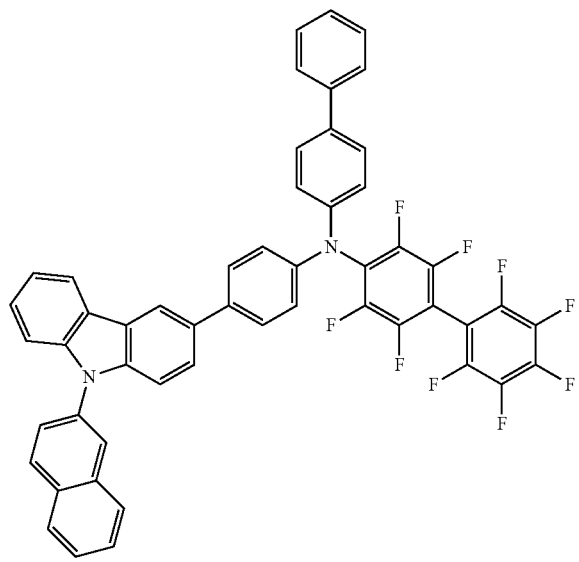
107
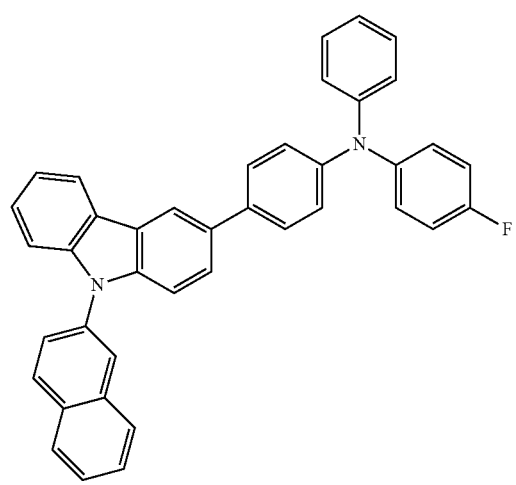
108
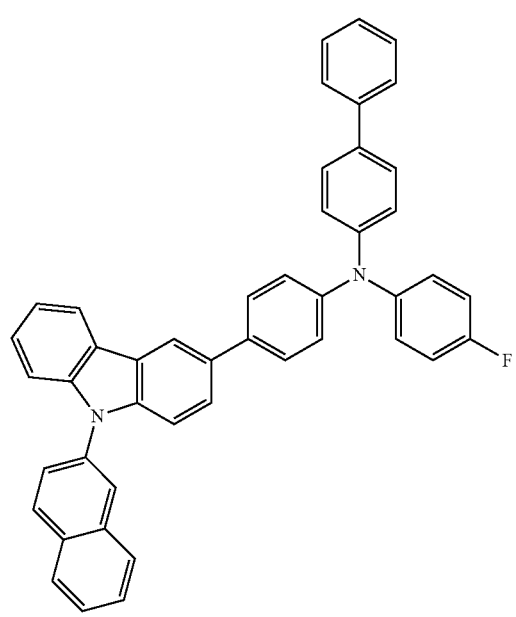
-continued
109
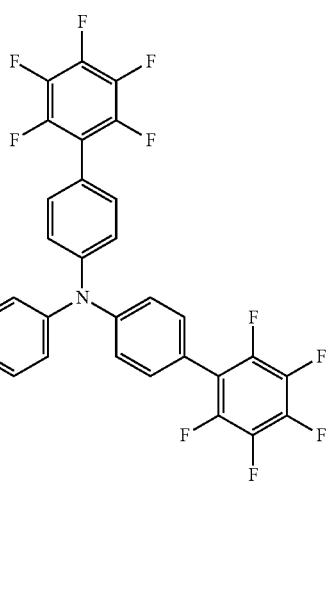
110
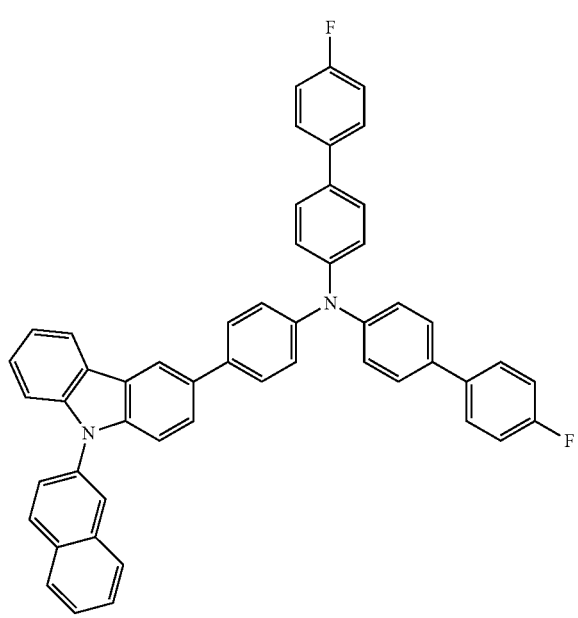

-continued
111
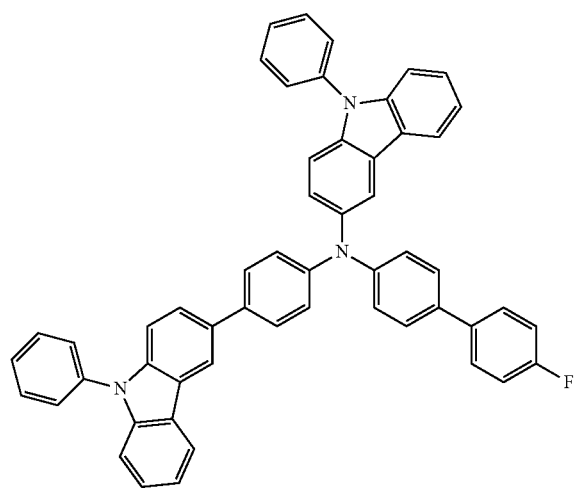
112
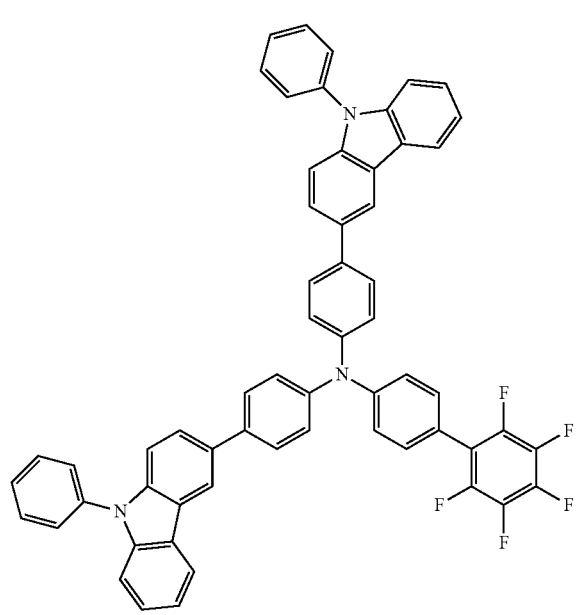
113
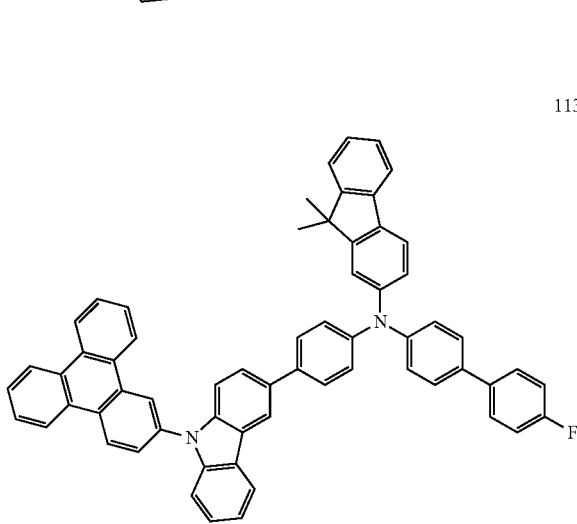
-continued
114
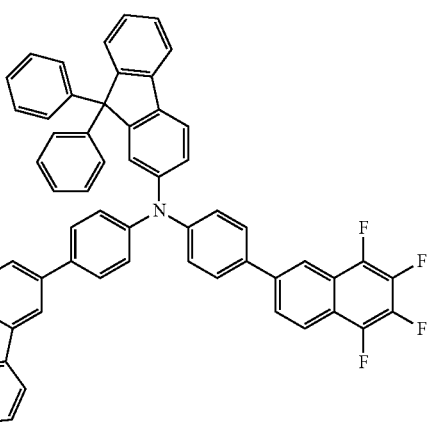
115
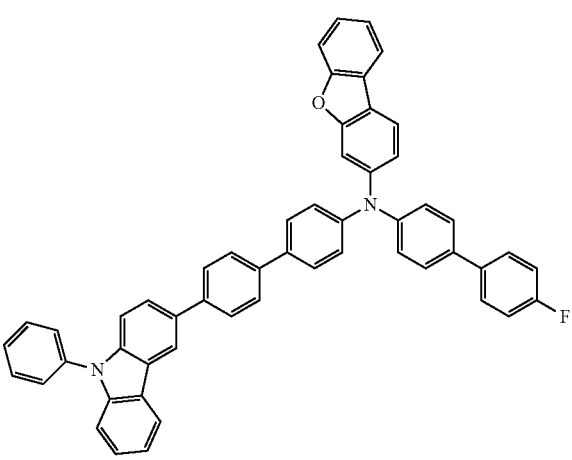
116
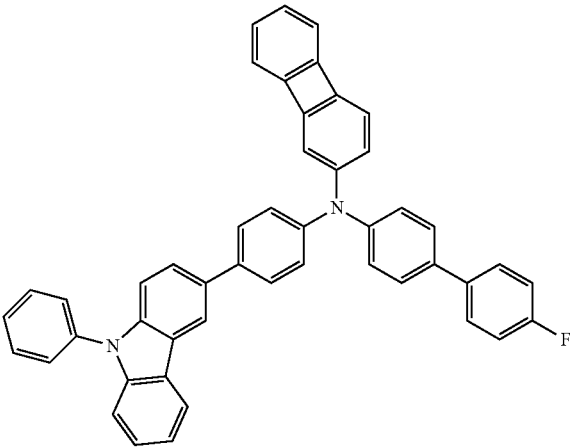

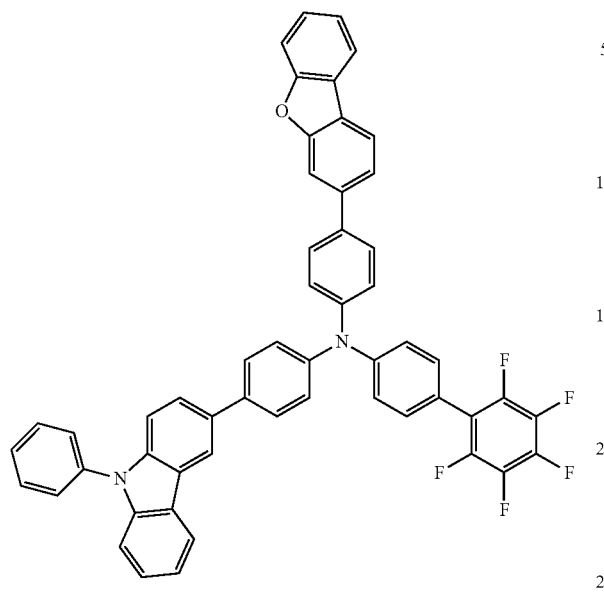
117
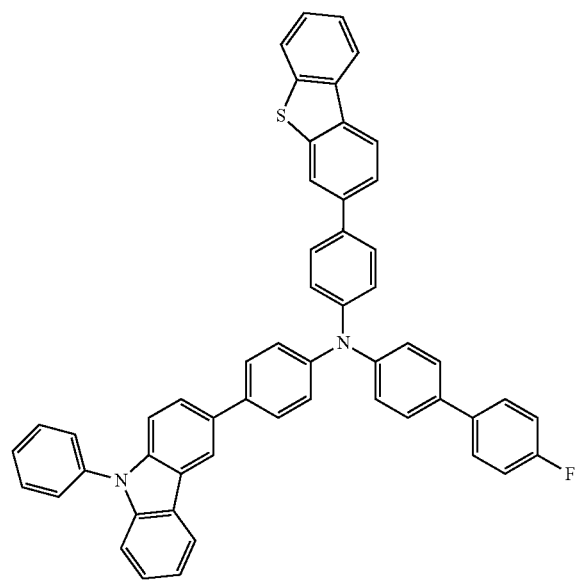
119
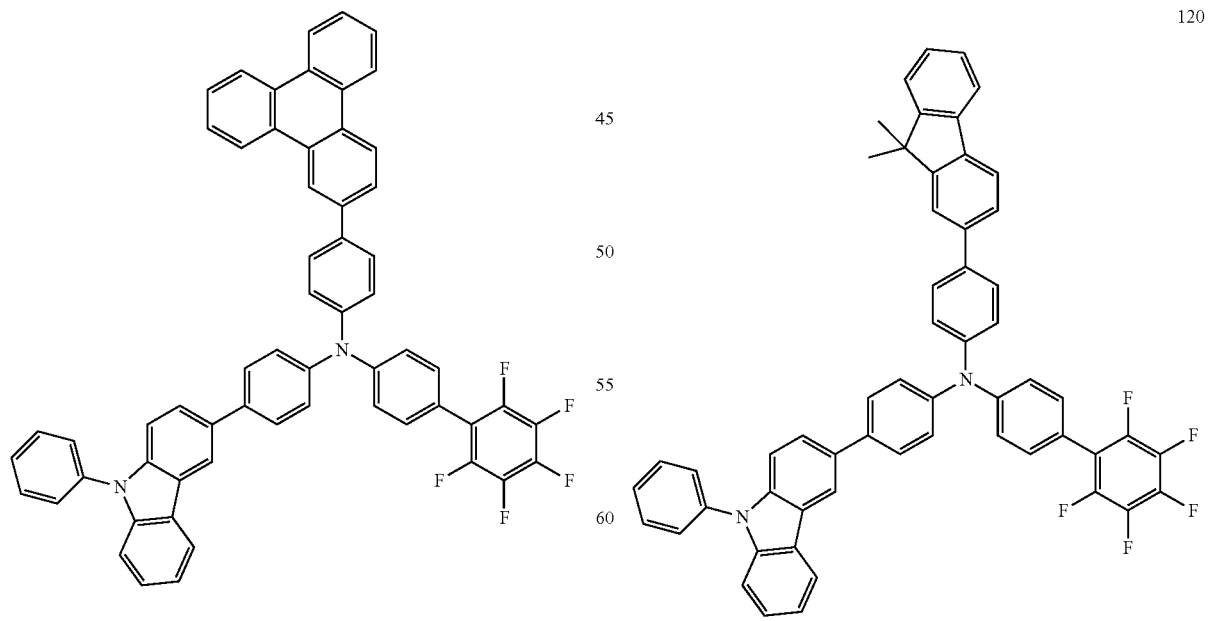

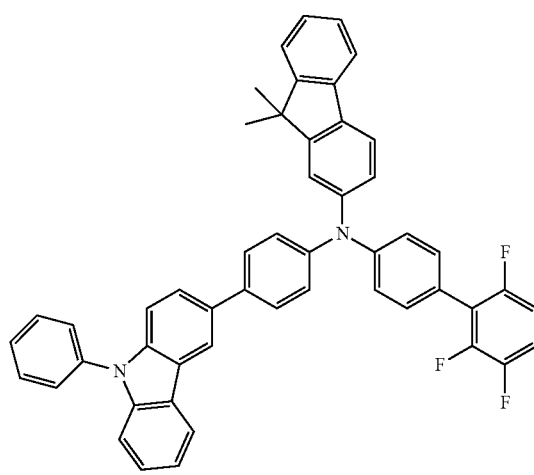
121
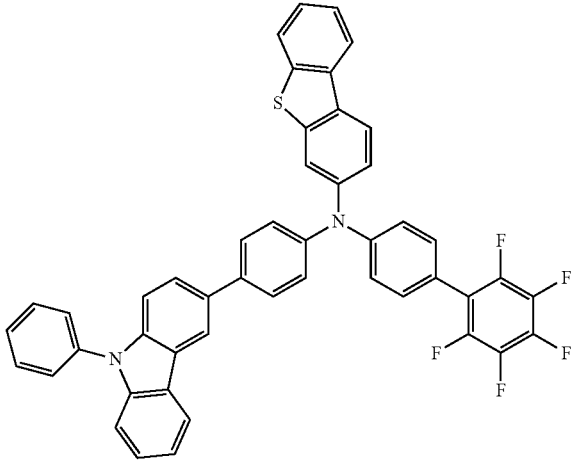
124
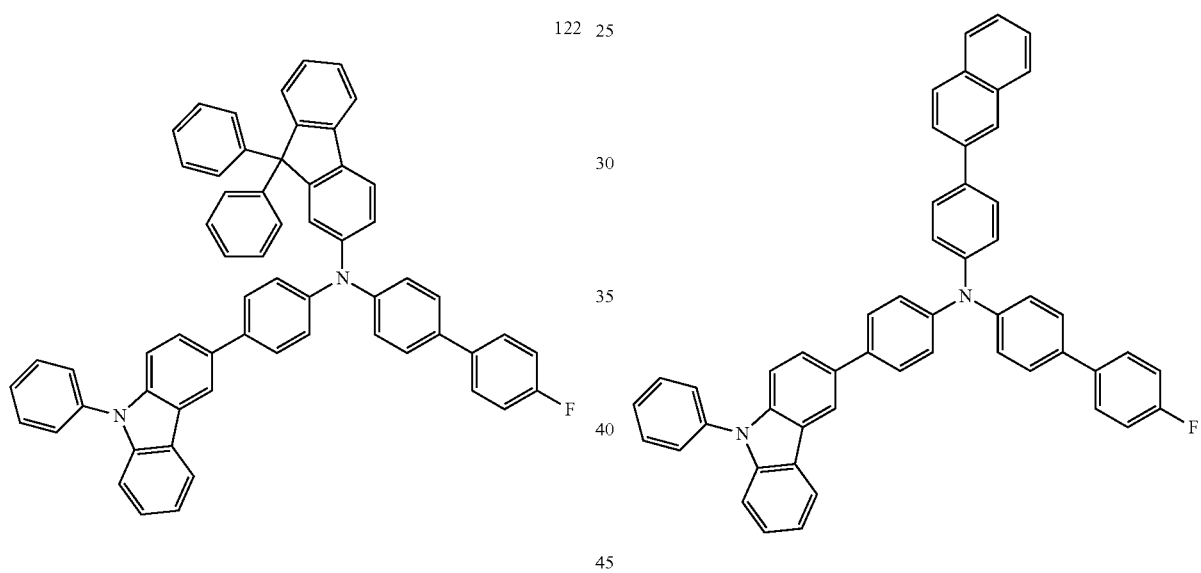
122
125
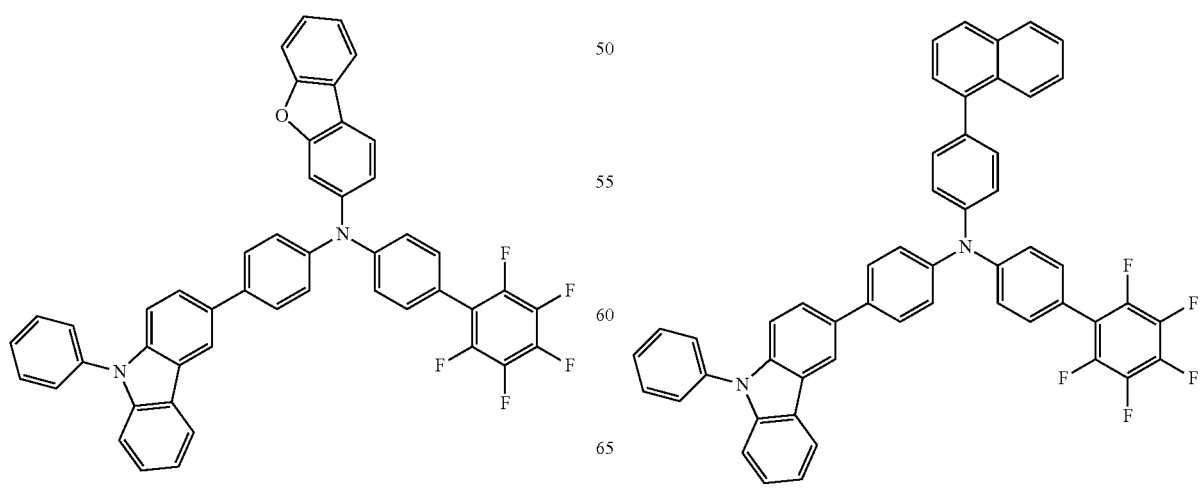
123
126

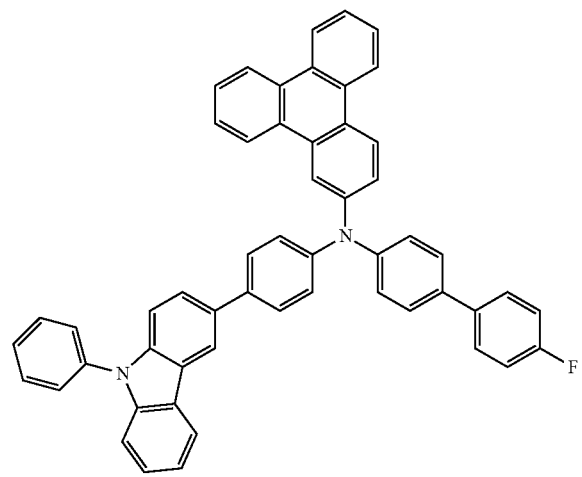
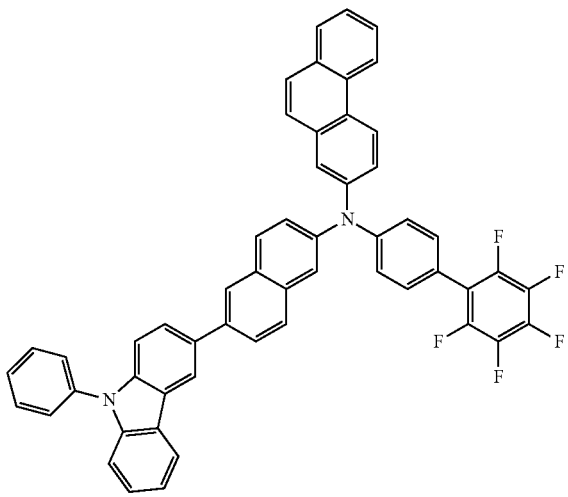

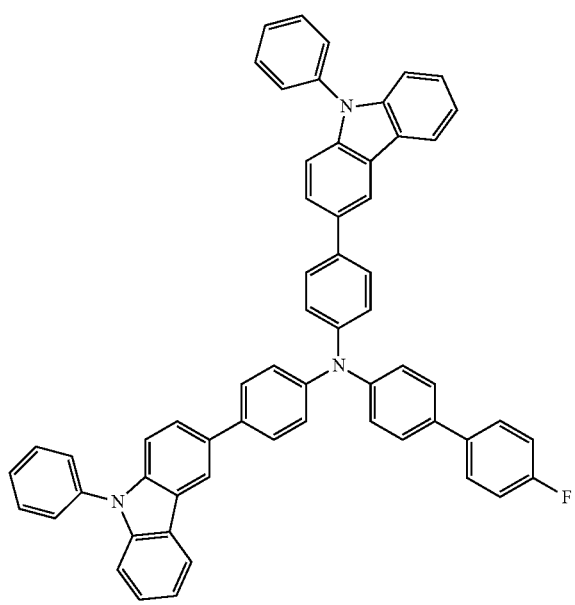
132
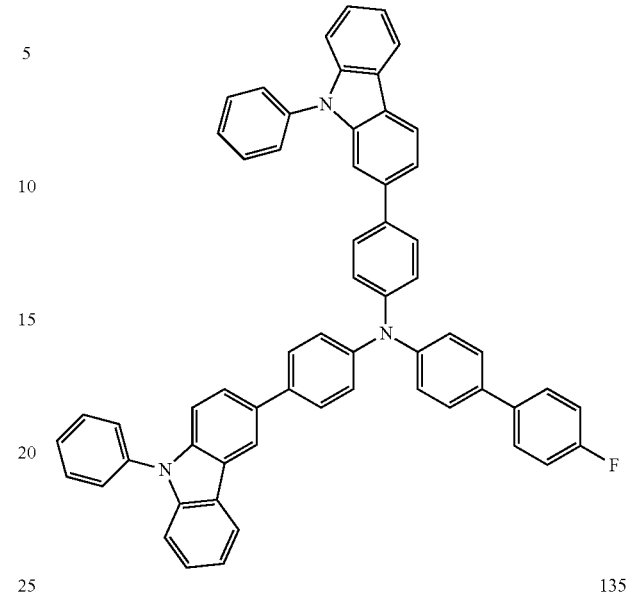
134
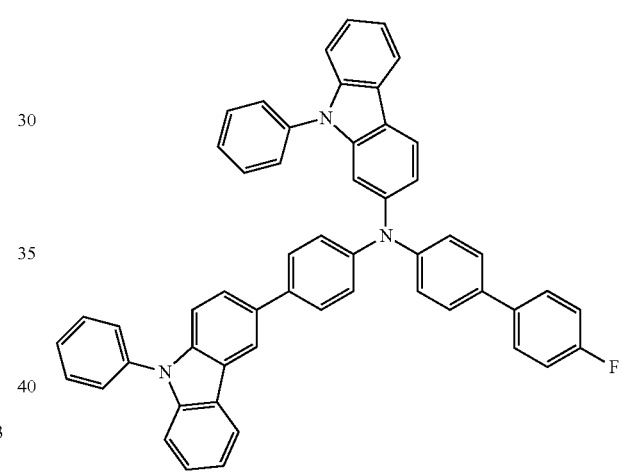
135
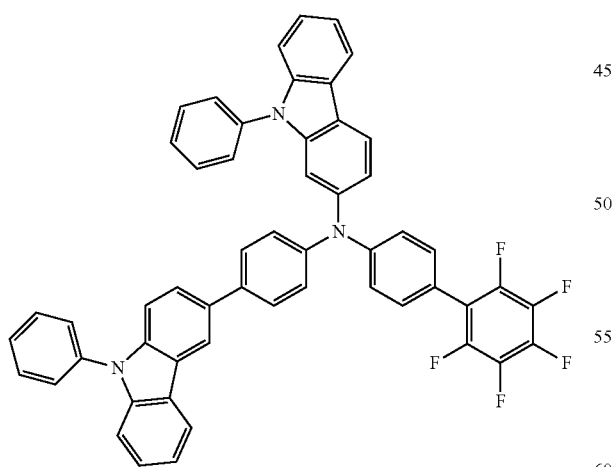
133
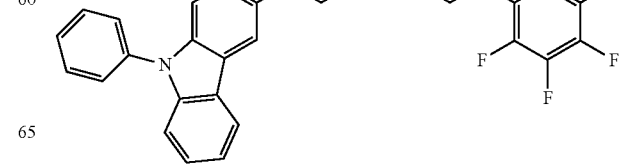
136

-continued
137
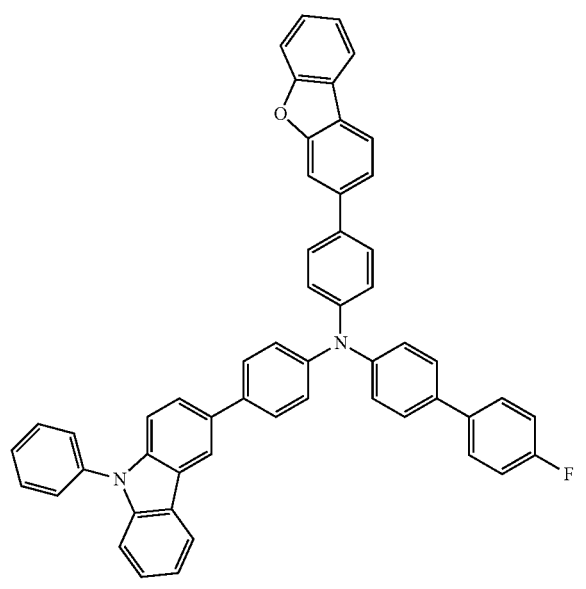
138
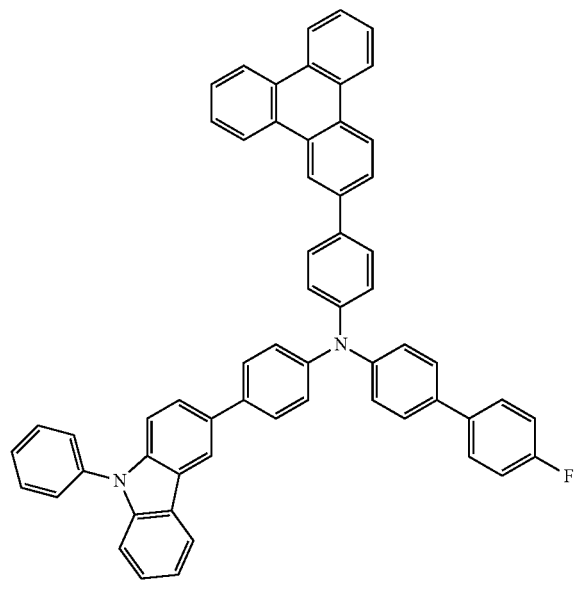
-continued
139
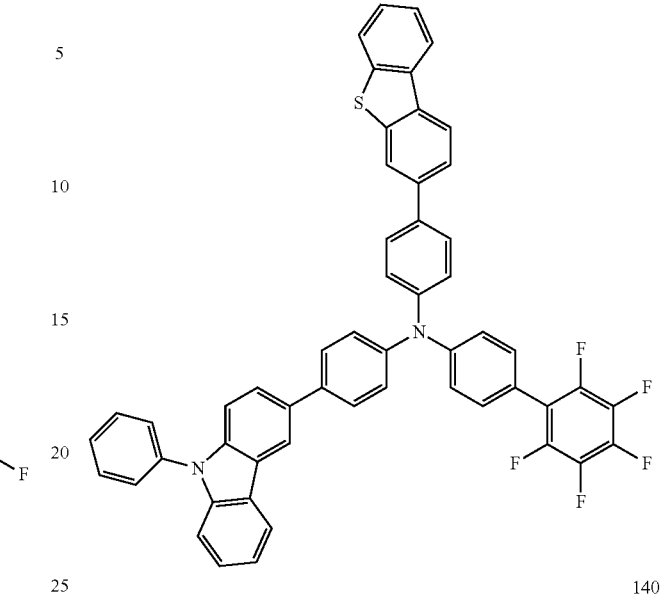
140
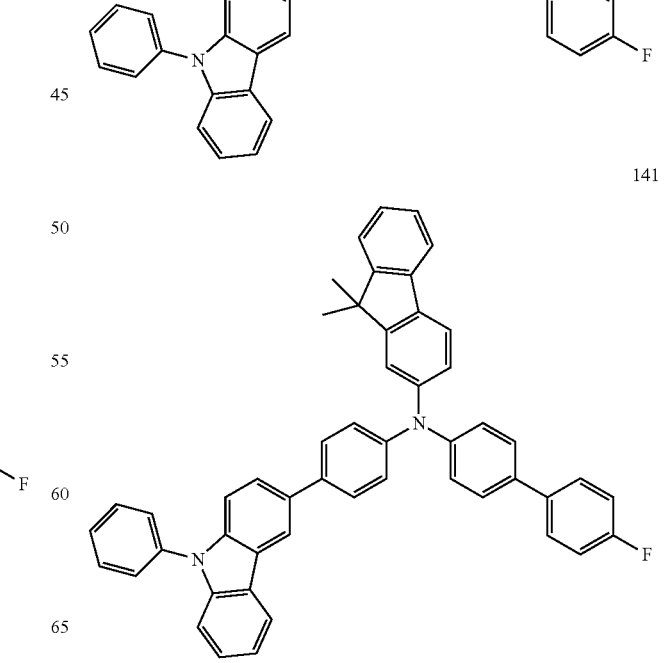
141

142
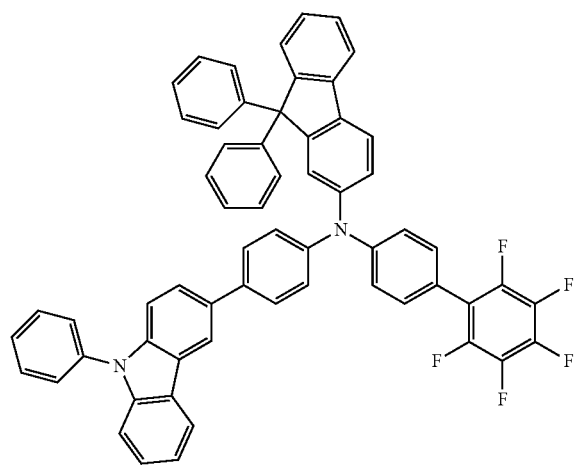
143
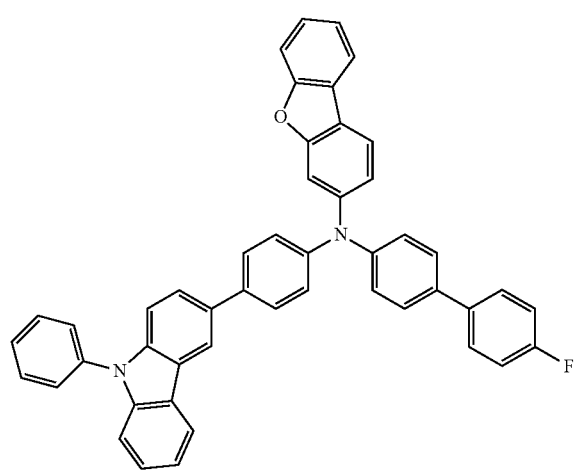
144
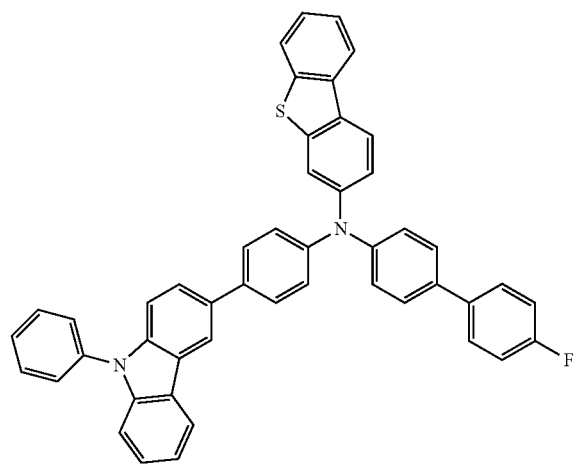
145
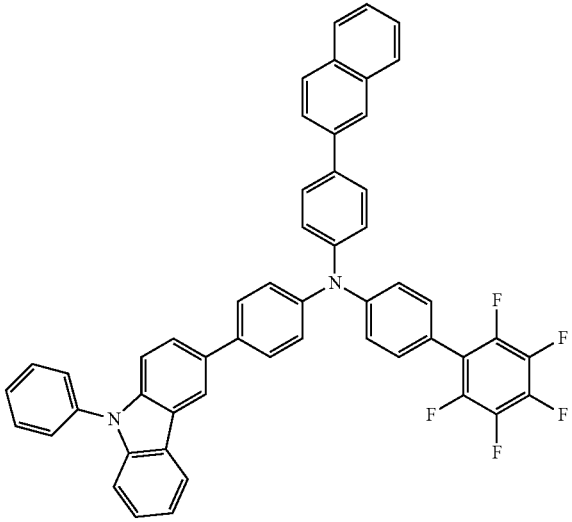
146
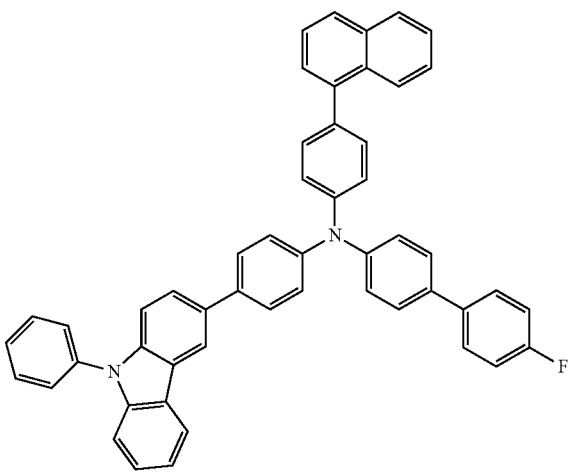
147
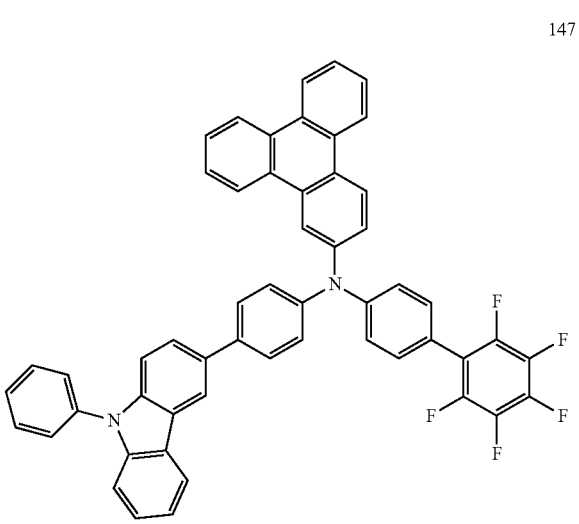

131
-continued
148
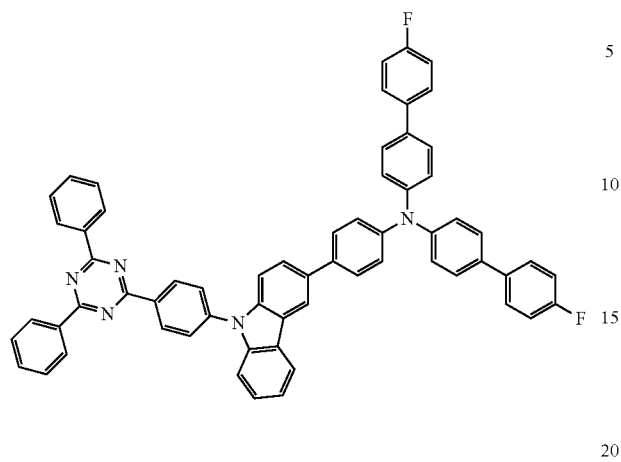
149
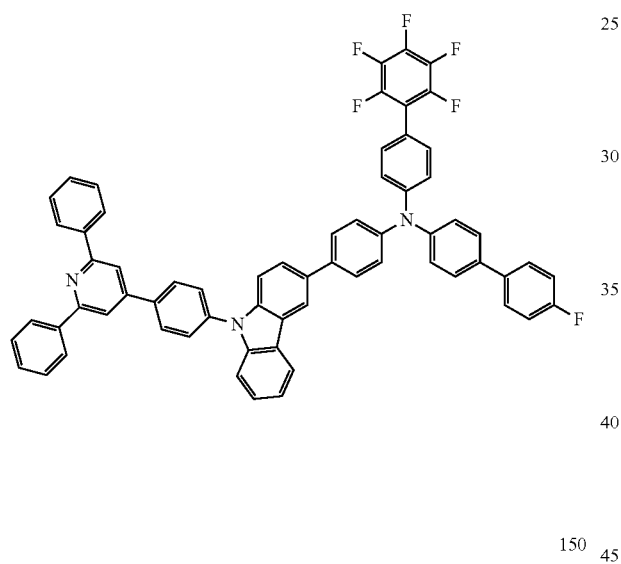
150
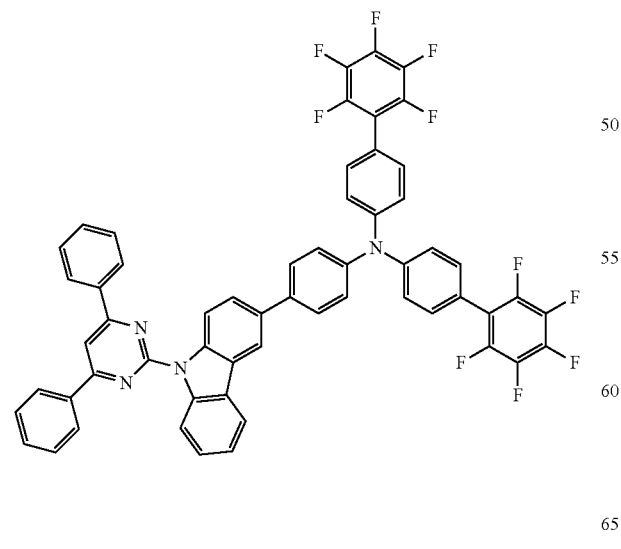
132
-continued
151
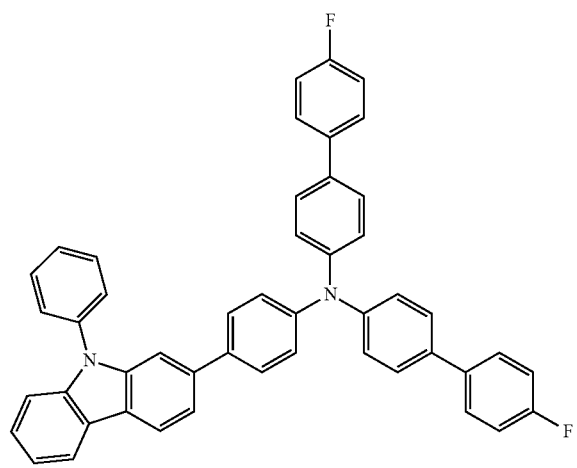
152
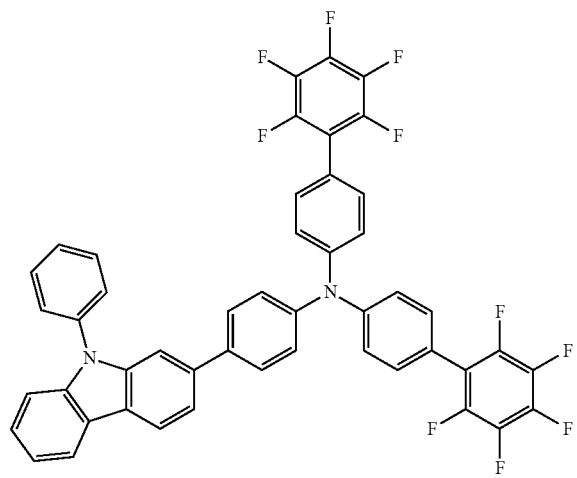
153
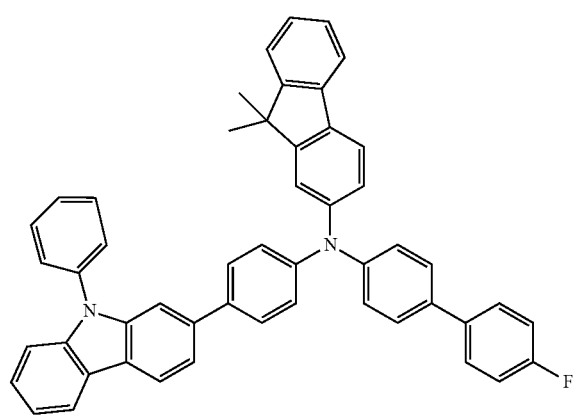

154
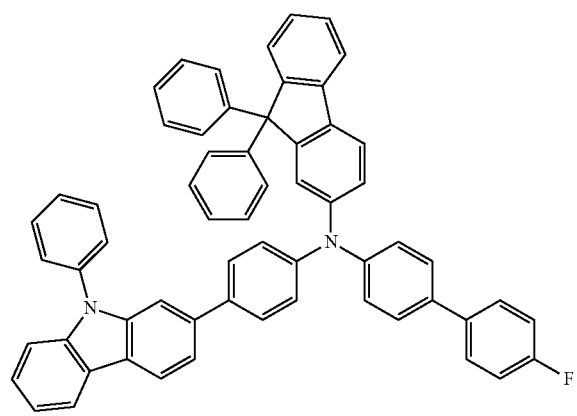
155
156
157
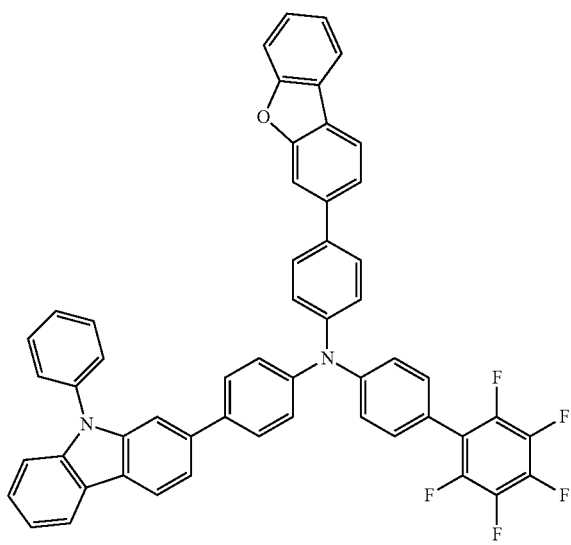
158
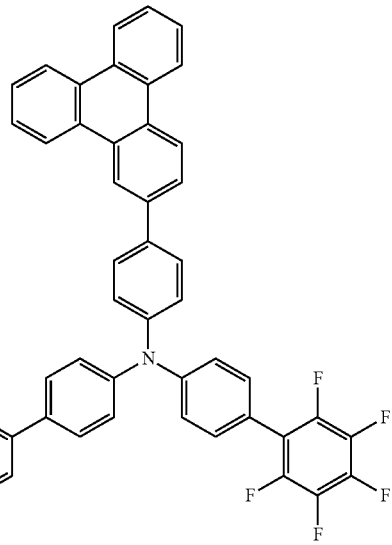

159
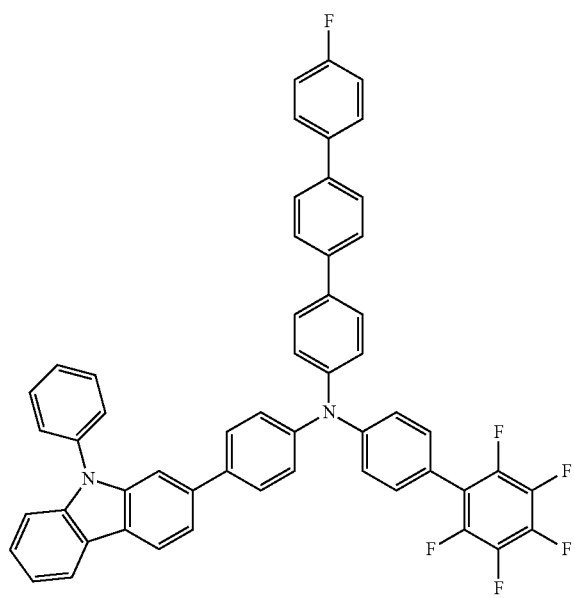
160
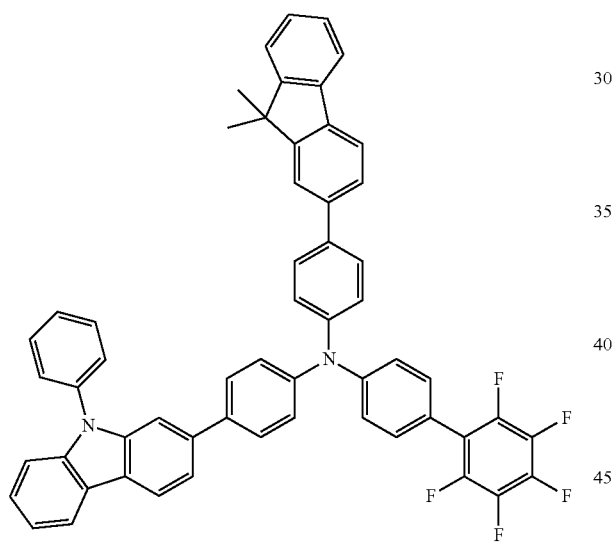
161
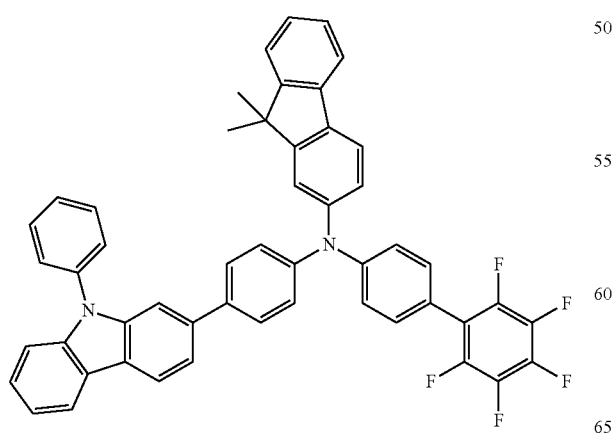
162
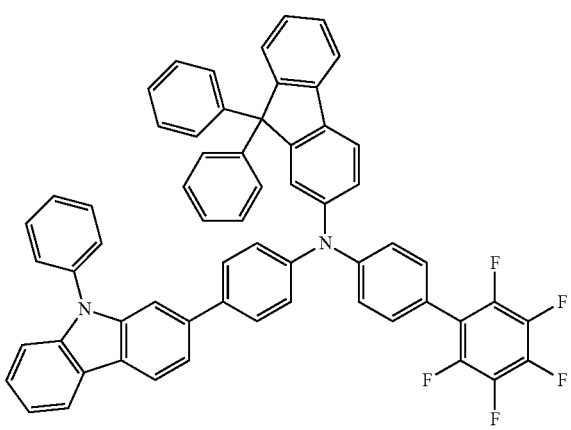
163
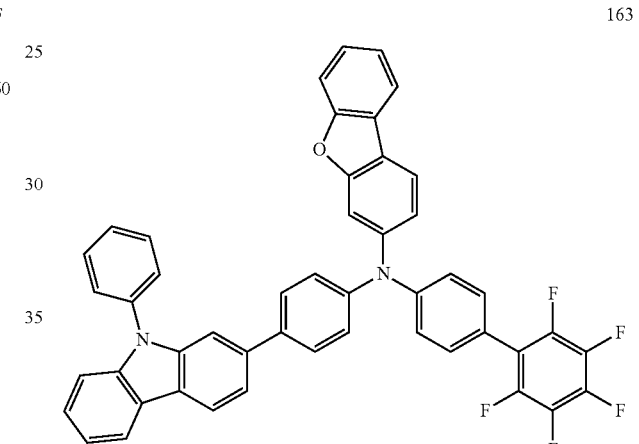
164
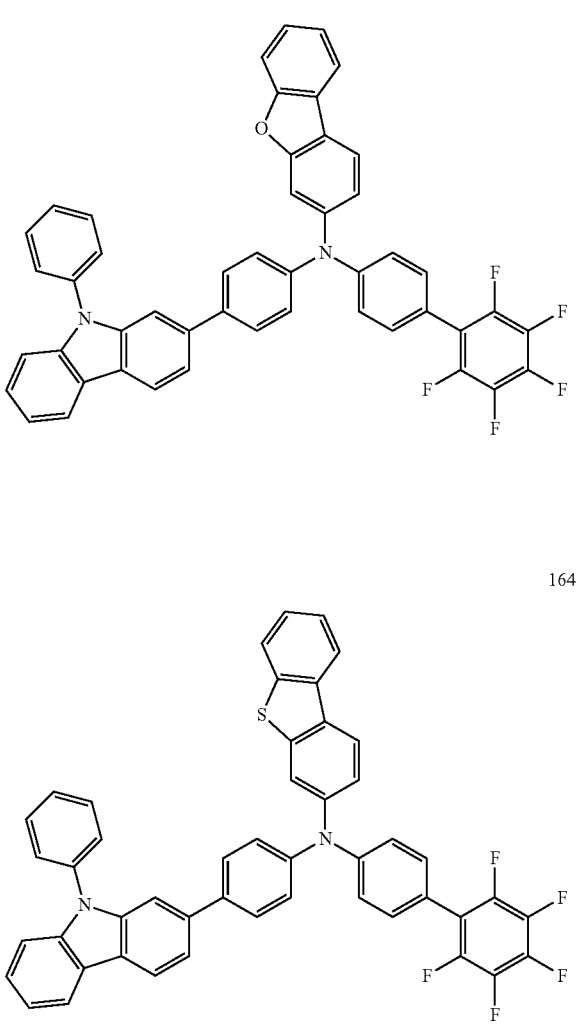

165
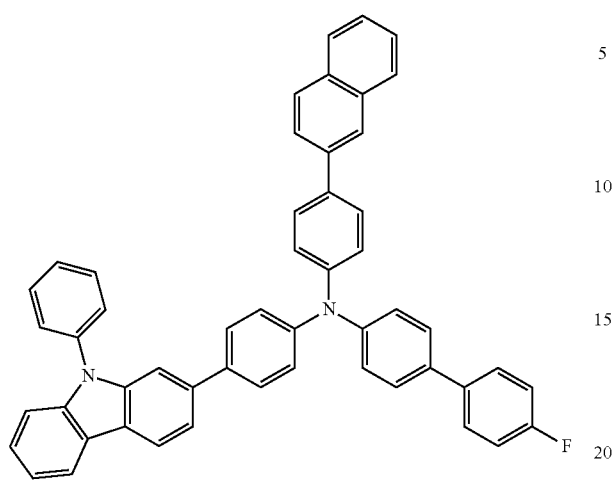
166
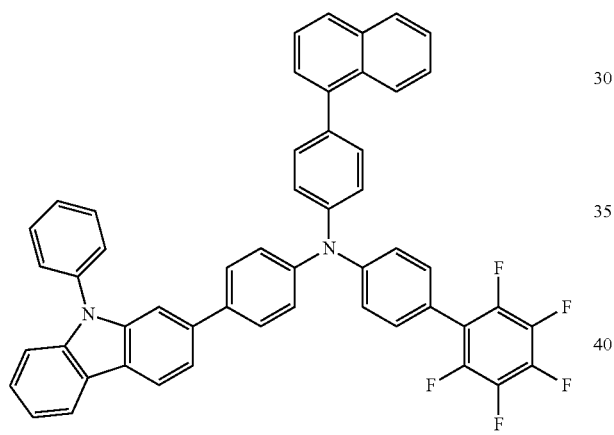
167
168
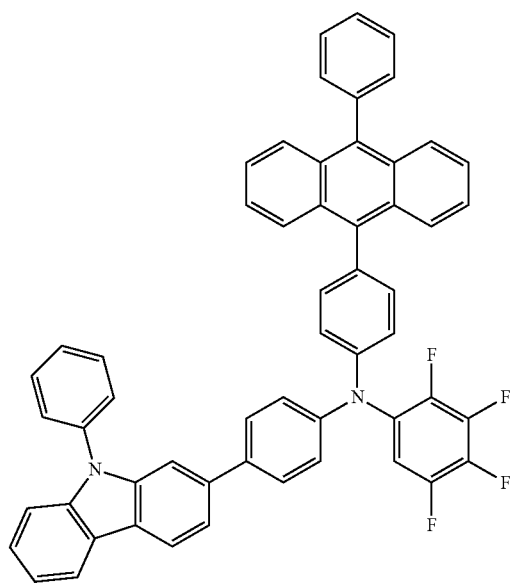
169
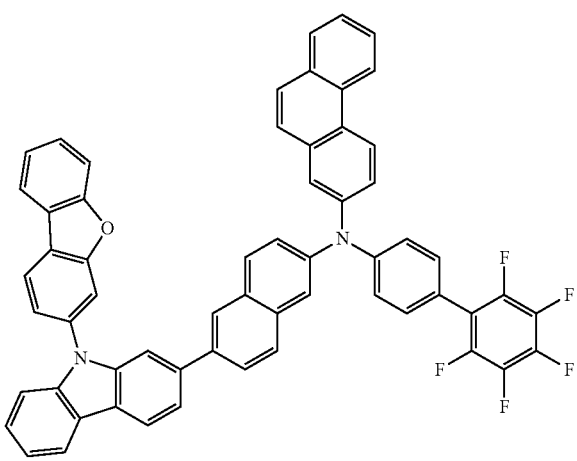
170
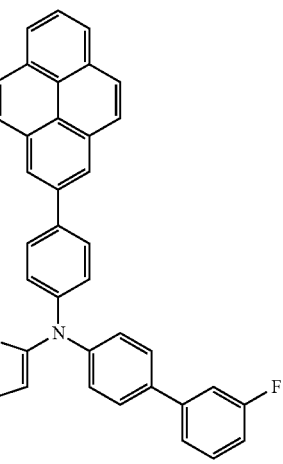
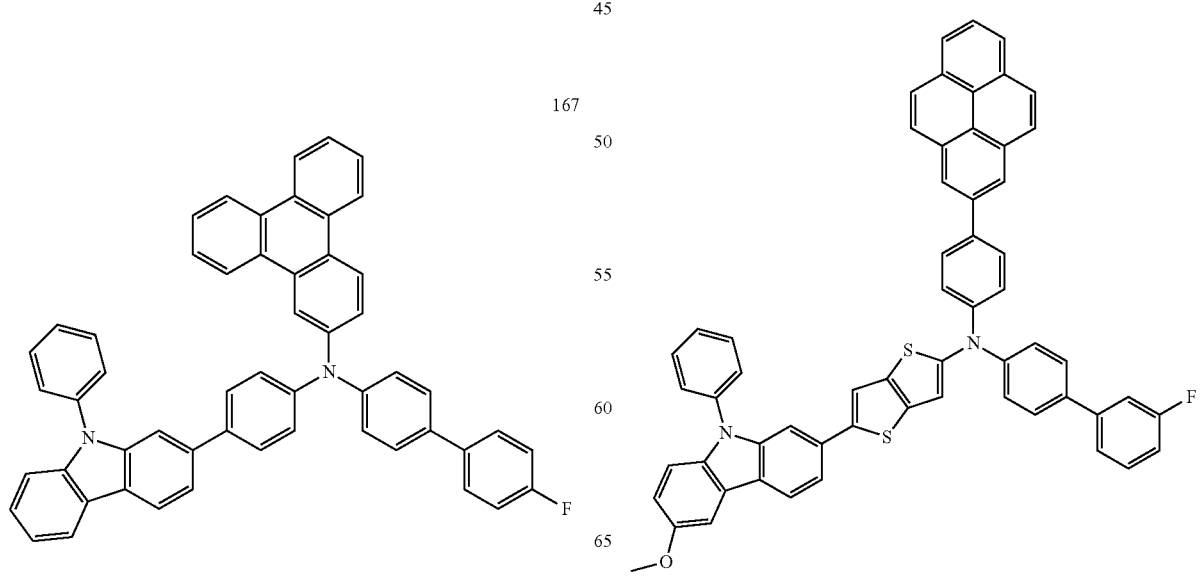

-continued
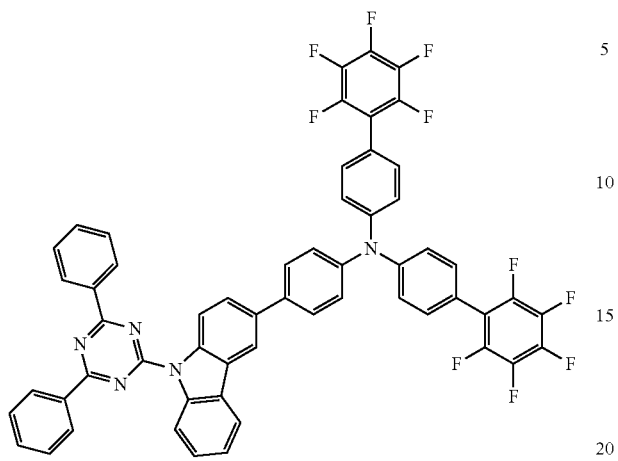
171
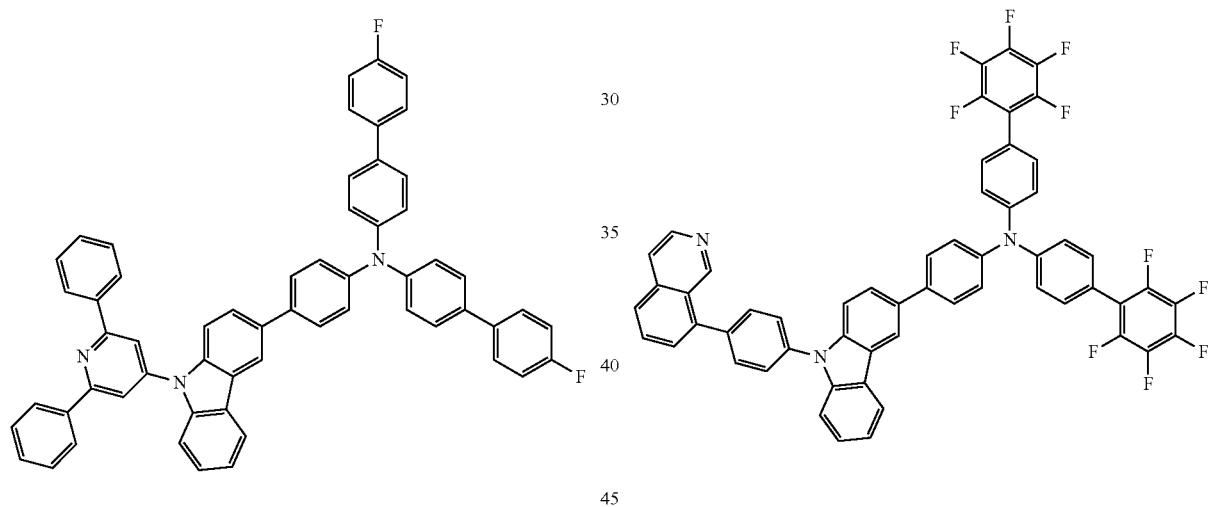
172
173
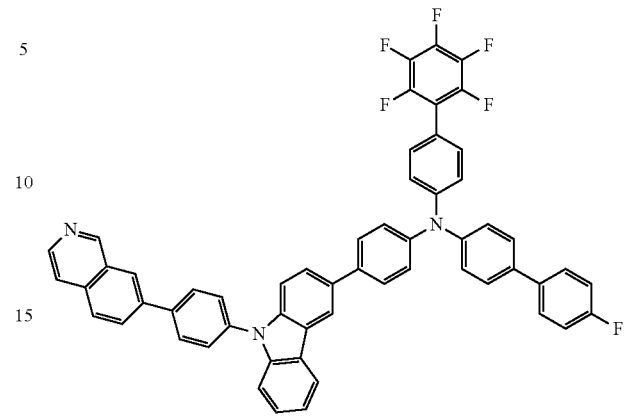
174
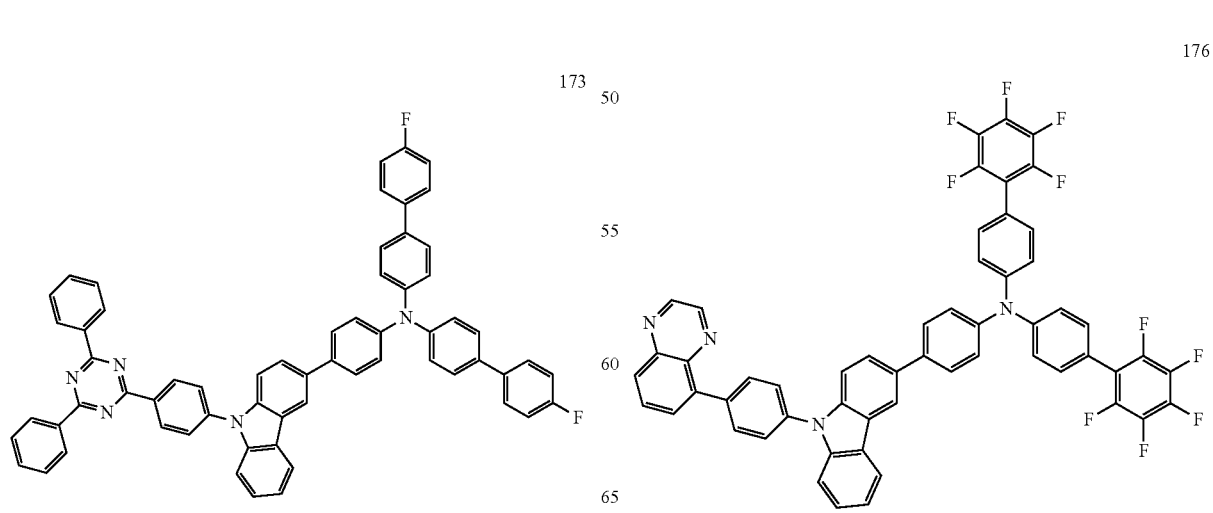
175
176

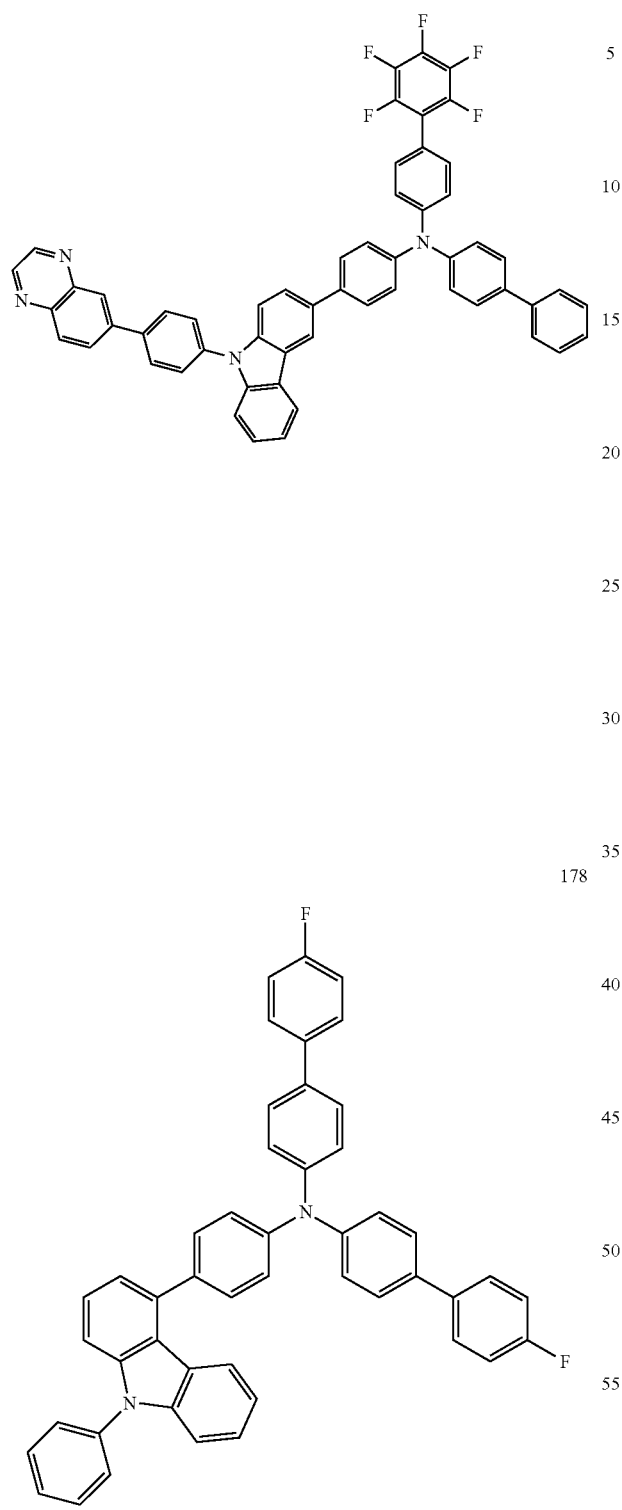

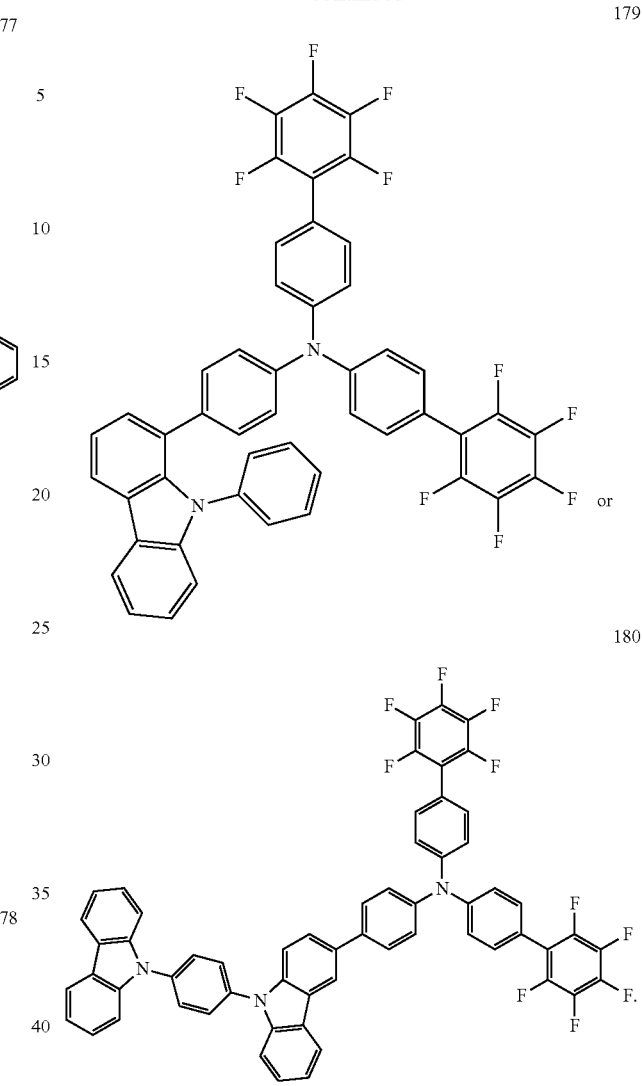

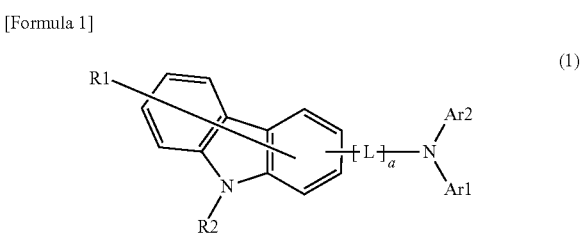

2. A compound represented by the following Formula 1:
[Formula 1]

[Formula 1]

(1)

wherein, wherein each of Ar1 and Ar2 independently represents a substituted or unsubstituted biphenyl group, L is a substituted or unsubstituted phenylene group, R1 is a hydrogen atom, and R2 is a substituted or unsubstituted aryl group, a is an integer satisfying $0 \leq a \leq 3$, and at least one of Ar1 and Ar2 is a substituted biphenyl group substituted with at least one fluorine atom.

3. An organic electroluminescence material comprising the compound as claimed in claim 2.

4. A hole transport material comprising the compound as claimed in claim 2.

5. An organic electroluminescence device comprising at least an emission layer and a hole transport layer disposed between a negative electrode and a positive electrode, wherein the hole transport layer includes the compound as claimed in claim 2.

* * * * *